(12) United States Patent
Cooper et al.

(10) Patent No.: US 9,701,758 B2
(45) Date of Patent: Jul. 11, 2017

(54) ANTI-CD19 SCFV (FMC63) POLYPEPTIDE

(71) Applicant: BOARD OF REGENTS, THE UNIVERSITY OF TEXAS SYSTEM, Austin, TX (US)

(72) Inventors: Laurence J N Cooper, Houston, TX (US); Bipulendu Jena, Houston, TX (US); Sourindra Maiti, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/893,223

(22) PCT Filed: May 23, 2014

(86) PCT No.: PCT/US2014/039365
§ 371 (c)(1),
(2) Date: Nov. 23, 2015

(87) PCT Pub. No.: WO2014/190273
PCT Pub. Date: Nov. 27, 2014

(65) Prior Publication Data
US 2016/0096902 A1 Apr. 7, 2016

Related U.S. Application Data

(60) Provisional application No. 61/827,312, filed on May 24, 2013.

(51) Int. Cl.
| | | |
|---|---|---|
| *A61K 39/395* | (2006.01) | |
| *C07K 16/42* | (2006.01) | |
| *C07K 16/28* | (2006.01) | |
| *C12N 5/0783* | (2010.01) | |
| *C07K 14/705* | (2006.01) | |
| *G01N 33/566* | (2006.01) | |

(52) U.S. Cl.
CPC .... *C07K 16/4208* (2013.01); *C07K 14/70503* (2013.01); *C07K 14/70517* (2013.01); *C07K 16/2803* (2013.01); *C07K 16/4283* (2013.01); *C12N 5/0636* (2013.01); *G01N 33/566* (2013.01); *C07K 2317/622* (2013.01); *C07K 2317/74* (2013.01); *C07K 2317/75* (2013.01); *C07K 2317/76* (2013.01); *C07K 2319/02* (2013.01); *C07K 2319/31* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | |
|---|---|---|
| 6,489,458 B2 | 12/2002 | Hackett et al. |
| 6,986,887 B2 | 1/2006 | Lawman et al. |
| 7,833,706 B2 | 11/2010 | Begovich et al. |
| 7,888,121 B2 | 2/2011 | Urnov et al. |
| 8,945,868 B2 | 2/2015 | Collingwood et al. |
| 8,956,828 B2 | 2/2015 | Bonini et al. |
| 2003/0194704 A1 | 10/2003 | Penn et al. |
| 2006/0286603 A1 | 12/2006 | Kolkman et al. |
| 2007/0032637 A1 | 2/2007 | Yokoyama et al. |
| 2007/0036773 A1 | 2/2007 | Cooper et al. |
| 2007/0283453 A1 | 12/2007 | Rodriguez Cimadevilla et al. |
| 2009/0197309 A1 | 8/2009 | Sycheva et al. |
| 2009/0258363 A1 | 10/2009 | Gregory et al. |
| 2010/0226917 A1* | 9/2010 | Brown .............. A61K 31/4535 424/133.1 |
| 2011/0158957 A1 | 6/2011 | Bonini et al. |
| 2011/0236363 A1 | 9/2011 | Chang et al. |
| 2013/0280220 A1 | 10/2013 | Ahmed et al. |

FOREIGN PATENT DOCUMENTS

| | | |
|---|---|---|
| WO | WO 2016-073629 | 5/1916 |
| WO | WO 2016-073755 | 5/1916 |
| WO | WO 03-089618 | 10/2003 |
| WO | WO 2009-091826 | 7/2009 |
| WO | WO 2010-008564 | 1/2010 |
| WO | WO 2010-108127 | 9/2010 |
| WO | WO 2011-059836 | 5/2011 |
| WO | WO 2012-079000 | 6/2012 |
| WO | WO 2013-040557 | 3/2013 |
| WO | WO 2013-059593 | 4/2013 |
| WO | WO 2013-063419 | 5/2013 |
| WO | WO 2013-074916 | 5/2013 |
| WO | WO 2013-084147 | 6/2013 |
| WO | WO 2014-037807 | 3/2014 |
| WO | WO 2014-100385 | 6/2014 |
| WO | WO 2014-144622 | 9/2014 |
| WO | WO 2014-164554 | 10/2014 |

(Continued)

OTHER PUBLICATIONS

Rudikoff et al., Proc Natl Acad Sci USA 79: 1979-1983 (1982).*
Colman, Research in Immunology 145: 33-36 (1994).*
Kussie et al. J. Immunol. 152: 146-152 (1994).*
Chen et al., EMBO J., 14: 2784-2794 (1995).*
"Human leukocyte antigen", *Wikipedia*, downloaded on Jun. 3, 2016.
Aronovich et al., "The Sleeping Beauty transposon system: a non-viral vector for gene therapy", *Hum. Mol Genet.*, 20:R14-20, 2011.
Beerli and Barbas, "Engineering polydactyl zinc-finger transcription factors", *Nature Biotechnol.*, 20:135-141, 2002.

(Continued)

*Primary Examiner* — Phillip Gambel
(74) *Attorney, Agent, or Firm* — Parker Highlander PLLC

(57) ABSTRACT

Provided are monoclonal antibodies that detect CD 19 CAR-modified immune cells and CAR-modified immune cells irrespective of the tumor associated antigen they target. Methods of using these functional monoclonal antibodies include, but are not limited to, detection, quantification, activation, and selective propagation of CAR-modified immune cells.

6 Claims, 31 Drawing Sheets

(56) References Cited

FOREIGN PATENT DOCUMENTS

| WO | WO 2014-186469 | 11/2014 |
|----|----------------|---------|
| WO | WO 2015-061694 | 4/2015  |
| WO | WO 2015-123642 | 8/2015  |
| WO | WO 2015-164594 | 10/2015 |
| WO | WO 2015-164740 | 10/2015 |

OTHER PUBLICATIONS

Beurdeley et al., "Compact designer TALENs for efficient genome engineering", *Nature Communications*, 4:1762 doi: 10.1038/ncomms2782, 2013.
Bhatnagar et al., "Turmor lysing genetically engineered T cless loaded with multi-modal imaging agents", *Sci Rep*, 4: 4502, 2014.
Boch et al., "Breaking the code of DNA binding specificity of TAL-type III effectors", *Science*, 326: 1509-1512, 2009.
Boissel et al., "megaTALs: a rare-cleaving nuclease architecture for therapeutic genome engineering", *Nucleic Acids Research*, 42(4): 2591-2601, 2014.
Bonas et al., "Genetic and structural characterization of the avirulence gene avrBs3 from *Xanthomonas campestris* pv. *vesicatoria*", *Mol Gen Genet.*, 218: 127-136, 1989.
Borrego et al., "Recognition of human histocompatibility leukocyte antigen (HLA)-E complexed with HLA class I signal sequence-derived peptides by CD94/NKG2 confers protection from natural killer cell-mediated lysis", *J Exp Med.*, 187(5): 813-8, 1998.
Braud et al., "HLA-E binds to natural killer cell receptors CD94/NKG2A, B and C", *Nature*, 391: 795-799, 1998.
Brentjens et al., "CD19-targeted T cells rapidly induce molecular remissions in adults with chemotherapy-refractory acute lymphoblastic leukemia", *Sci. Transl. Med.*, 5:177ra3 8, 2013.
Bukur et al., "The role of classical and non-classical HLA class I antigens in human tumors", *Seminars in Cancer Biology*, 22: 350-358, 2012.
Bullain et al., "Genetically engineered T cells to target EGFRvIII expressing glioblastoma", *Journal of Neuro-Oncology*, 94(3): 373-382, 2009.
Caruso, "CAR-modified T cells capably of distinguishing normal cells from malignant cells", *UT GBS Dissertations and Theses*, dated May 1, 2014, retrieved from digitalcommons.library.tmc.edu/cgi/viewcontent.cgi?article=1497&context=utgsbs_dissertations on Jul. 15, 2015.
Chmielewski et al., "T cell activation by antibody-like immunorecepteros: increase in affinity of the single-chain fragment domain above threshold does not increase T cell activation against antigen-positive target cells but decrease selectivity", *Journal of Immunology*, 173(12): 7647-7653, 2004.
Choi et al., "A high throughput microelectroporation devise to introduce a chimeric antigen receptor to redirect the specificity of human T cells", *Biomed Microdevices*, 12(5): 855-63, 2010.
Choi et al., "Intercerebral delivery of a third generation EGFRvIII-specific chimeric antigen receptor is efficacious against human glioma", *Journal of Clinical Neuroscience*, 21(1): 189-190, 2014.
Choo and Isalan, "Advances in zinc finger engineering", *Curr Opin Struct Biol.*, 10(4): 411-6, 2000.
Cohen et al., "In vivo expression of MHC class I genes depends on the presence of a downstream barrier element", *PLoS ONE*, 4(8): e6748. Doi:10.1371/journal.pone.0006748, 2009. Figure 1.
Collin et al., "Concise review: putting a finger on stem cell biology: zinc finger nuclease-driven targeted genetic editing in human pluripotent stem cells", *Stem Cells* 19: 1021-1033, 2011.
Cooper et al., "Good T cells for bad B cells", *Blood*, 119: 2700-2702, 2012.
Cooper, "T-cell therapy for diffuse pontine glioma", *The Dana Foundation Grant Summary*, 2015.
Davies et al., "Combining CD19 redirection and alloanergization to generate tumor-specific human T cells for allogeneic cell therapy of B-cell malignancies", *Cancer Res.*, 70: 3915-3924, 2010.

Davies et al., "Flexible targeting of ErbB dimers that drive tumorigenesis by using genetically engineered T cells", *Molecular Medicine*, 18(1); 565-576, 2012.
De Oliveira et al., "A CD19/Fc fusion protein for detection of anti-CD19 chimeric antigen receptors", *Journal of Translational Medicine*, 11:23, 2013.
De Oliveira et al., "Modification of hematopoietic stem-progenitor cells with CD19-specific chimeric antigen receptors as a novel approach for cancer immunotherapy", *Hum Gene Ther.*, 24(10): 824-39, 2013.
Deniger et al. "Bispecific T-cells expressing polyclonal repertoire of endogenous gammadelta T-cell receptors and introduced CD19-specific chimeric antigen receptor", *Mol Ther.* Mar. 2013;21(3):638-647.
Deniger, "T-Cell treatments for solid and hematological tumors", *UT GBS Dissertations and Theses*, dated Aug. 2013, retrieved from digitalcommons.library.tmc.edu/cgi/viewcontent.cgi?article=1421&context=utgsbs_dissertations on Dec. 14, 2014.
Ehlers et al., "Alphabeta T cell receptor-positive cells and interferon-gamma, but not inducible nitric oxide synthase, are critical for granuloma necrosis in a mouse model of mycobacteria-induced pulmonary immunopathy", *The Journal of Experimental Medicine*, 194(12):1847-1859, 2001.
Ertl et al., "Considerations for the clinical application of chimeric antigen receptor T cells: observations from a recombinant DNA Advisory Committee Symposium held Jun. 15, 2010", *Cancer Res.*, 71:3175-3181, 2011.
Fehling et al., "MHC class I expression in mice lacking the proteasome subunit LMP-7", *Science*, 265(5176): 1234-7, 1994.
Feng et al., "Scalable generation of universal platelets from human induced pluripotent stem cells", *Stem Cell Reports*, 3(5): 817-831, 2014.
Garbi et al., "Impaired immune responses and altered peptide repertoire in tapasin-deficient mice", *Nature Immunology*, 1(3): 234-8, 2000.
Gascoigne, "Transport and secretion of truncated T cell receptor and chamin occurs in the absence of association with CD3", *The Journal of Biological Chemistry*, 265(16):9296-9301, 1990.
Geurts et al., "Structure-based prediction of insertion-site preferences of transposons into chromosomes", *Nucleic Acids Res.*, 34:2803-2811, 2006.
Grandea et al., "Impaired assembly yet normal trafficking of MHC class I molecules in Tapasin mutant mice", *Immunity*, 13: 231-222, 2000.
Grupp et al., "Chimeric antigen receptor-modified T cells for acute lymphoid leukemia", *The New England Journal of Medicine*, 368(16): 1509-18, 2013.
Guerrero et al., "Th human application of gene therapy to re-program T-cell specificity using chimeric antigen receptors", *Chin J Cancer*, 33(9): 421-433, 2014.
Gupta et al., "Development of an EGFRvIII specific recombinant antibody", *BMC Biotechnology*, 10(1): 72, 2010.
Guschin et al., "A rapid and general assay for monitoring endogenous gene modification", in *Engineered Zinc Finger Proteins*, eds. Mackay and Segal, Ch. 15, pp. 247-256, 2010.
Hackett et al., "A transposon and transposase system for human application", *Mol. Ther.*, 18:674-683, 2010.
Hackett et al., "Efficacy and safety of Sleeping Beauty transposon-mediated gene transfer in preclinical animal studies", *Curr. Gene Ther.*, 11:341-349, 2011.
Haft et al., "A guild of 45 CRISPR-Associated (Cas) protein families and multiple CRISPR/Cas subtypes exist in prokaryotic genomes", *PLoS Comput Biol.*, 1(6): e60, 2005.
Heuer et al., "Repeat domain diversity of avrBs3-like genes in *Ralstonia solanacearum* strains and association with host preferences in the field", *Appl. Environ. Microbiol.*, 73(13): 4379-4384, 2007.
Hockemeyer et al., "A drug-inducible system for direct reprogramming of human somatic cells to pluripotency", *Cell Stem Cell*, 3: 346-353, 2008.
Holmes et al., "Disruption of HLA expression to enable allogeneic cells to escape immune recognition", *Human Gene Therapy*, 22(10): or 15, 2011.

(56) References Cited

OTHER PUBLICATIONS

Huang et al., "Genetically modified T cells targeting interleukin-11 receptor alpha-chain kill human osteosarcoma cells and induce the regression of established osteosarcoma lung metastases", *Cancer Res.*, 72:271-281, 2012.

Huls et al., "Clinical application of sleeping beauty and artificial antigen presenting cells to genetically modify T cells from peripheral and umbilical cord blood", *Journal of Visualized Experiments*, 72: e50070, 2013.

Isalan et al., "A rapid, generally applicable method to engineer zinc fingers illustrated by targeting the HIV-1 promoter", *Nat Biotechnol.*, 19(7): 656-660, 2001.

Ivics et al., "Molecular reconstruction of Sleeping Beauty, a Tc1-like transposon from fish, and its transposition in human cells", *Cell*, 91:501-510, 1997.

Izsvak and Ivics, "Sleeping beauty transposition: biology and applications for molecular therapy", *Mol. Ther.*, 9:147-156, 2004.

Izsvak et al., "Translating Sleeping Beauty transposition into cellular therapies: victories and challenges", *Bioessays*, 32:756-767, 2010.

Jamieson et al., "Drug discovery with engineered zinc-finger proteins", *Nature Reviews Drug Discovery* 2(5): 361-368, 2003.

Jansen et al., "Identification of genes that are associated with DNA repeats in prokaryotes", *Molecular Microbiology*, 43(6): 1565-1575, 2002.

Jaramillo et al., "Abstract 1778: nimotuzumab, ahumanized antiepidermal growth factor receptor antibody, interacts with EGFRvIII", *Cancer Res.*, dated Apr. 15, 2010.

Jena et al., "Chimeric antigen receptor (CAR)-specific monoclonal antibody to detect CD19-specific T cells in clinical trials", *PLoS One*, 8(3): e57838, 2013.

Jena et al., "Redirecting T-cell specificity by introducing a tumor-specific chimeric antigen receptor", *Blood*, 116:1035-1044, 2010.

Jena et al., "Specifically targeting the interface between HER1-HER3 heterodimer on breast cancer to limit off-target effects using chimeric antigen receptor designs with improved T-cell energy balance", *Blood*, 124(21): 2151, 2014.

Jin et al., "The hyperactive Sleeping Beauty transposase SB100X improves the genetic modification of T cells to express a chimeric antigen receptor", *Gene Ther.*, 18:849-856, 2011.

Jutten et al., "Binding of cetuximab to the EGFRvIII deletion mutant and its biological consequences in malignant glioma cells", *Radiotherapy and Oncology*, 92(3): 393-398, 2009.

Kageshita et al., "Down-regulation of HLA class I antigen-processing molecules in malignant melanoma", *American Journal of Pathology*, 154(3): 745-754, 1999.

Kalos et al., "T cells with chimeric antigen receptors have potent antitumor effects and can establish memory in patients with advanced leukemia", *Sci Transl Med.*, 3: 95ra73, 2011.

Kay et al., "A bacterial effector acts as a plant transcription factor and induces a cell size regulator", *Science*, 318(5850): 648-51, 2007. Supporting Material.

Kebriaei et al., "Chimeric antibody receptors (CARs): driving T-cell specificity to enhance anti-tumor immunity", *Frontiers in Bioscience*, 4: 520-531, 2014.

Kebriaei et al., "Infusing CD19-directed T cells to augment disease control in patients undergoing autologous hematopoietic stem-cell transplantation for advanced B-lymphoid malignancies", *Hum. Gene Ther.*, 23:444-450, 2012.

Kochenderfer et al., "B -cell depletion and remissions of malignancy along with cytokine-associated toxicity in a clinical trial of anti-CD19 chimeric-antigen-receptor-transduced T cells", *Blood*, 119:2709-2720, 2012.

Kochenderfer et al., "Eradication of B-lineage cells and regression of lymphoma in a patient treated with autologous T cells genetically engineered to recognize CD19", *Blood*, 116:40994102, 2010.

Kohn et al., "CARs on track in the clinic", *Mol. Ther.*, 19:432-438, 2011.

Kowolik et al., "CD28 costimulation provided through a CD19-specific chimeric antigen receptor enhances in vino persistence and antitumor efficacy of adoptively transferred T cells", *Cancer Res.*, 66(22): 10995-11004, 2006.

Krishnamurthy et al., "Targeting an ancient retrovirus express in melanoma using adoptive T-cell therapy", *Oral presentation of Immunology Graduate Program, The University of Texas Graduate School of Biomedical Sciences*, dated Feb. 24, 2012.

L'Haridon et al., "Transcriptional regulation of the MHC class I HLA-A11 promoter by the zinc finger protein ZFX", *Nucleic Acids Research*, 24(10): 1928-1935, 1996.

LeibundGut-Landmann et al., "Specificity and expression of CIITA, the master regulator of MHC class II genes", *Eur. J. Immunol.*, 34: 1513-1525, 2004.

Lorimer et al., "Recombinant immunotoxins specific for a mutant epidermal growth factor receptor: targeting with a single chain antibody variable domain isolated by phage display", *Proceeding of the National Academy of Sciences U.S.A.*, 93: 14815-14820, 1996.

Maier et al., "High-resulution HLA alleles and haplotypes in the United States population", *Human Immunology*, 68: 779-788, 2007.

Maiti et al., "Sleeping beauty system to redirect T cell specific for human applications", *J Immunother.*, 36(2): 112-23, 2013.

Makarova et al., "A DNA repair system specific for thermophilic archaea and bacteria predicted by genomic context analysis", *Nucleic Acids Research*, 30(2): 482-496, 2002.

Makarova et al., "A putative RNA-interference-based immune system in prokaryotes: computational analysis of the predicted enzymatic machinery, functional analogies with eukaryotic RNAi, and hypothetical mechanisms of action", *Biology Direct*, 1:7, 2006.

Manuri et al., "piggyback transposon/transposase system to generate CD19-specific T cells for the treatment of B-lineage malignancies", *Human Gene Therapy*, 21: 427-437, 2010.

Mateo et al., "Humanization of a mouse monoclonal antibody that blocks the epidermal growth factor receptor: recovery of antagonistic activity", *Immunotechnology*, 3(1): 71-81, 1997.

Mates et al., "Molecular evolution of a novel hyperactive Sleeping Beauty transposase enables robust stable gene transfer in vertebrates", *Nat. Genetics.* 41(6):753-61, 2009.

Moscou and Bogdanove, "A simple cipher governs DNA recognition by TAL effectors", *Science*, 326: 1501, 2009.

Motmans et al., "Enhancing the tumor-specificity of human T cells by the expression of chimeric immunoglobulin/T cell receptor genes", *Immunotechnology* 2(4): 303-304, 1995.

Nakazawa et al., "Optimization of the piggyback transposon system for the sustained genetic modification of human T lymphocytes", *Journal of Immunotherapy*, 32(8): 826-836, 2009.

NCBI, Genbank accession No. AAT73716.1, dated Oct. 20, 2004.
NCBI, Genbank accession No. AAU14166.1, dated Mar. 16, 2005.
NCBI, Genbank accession No. ACC78293.1, dated Apr. 29, 2008.
NCBI, Genbank accession No. CAD61786.1, dated Jan. 24, 2003.
NCBI, Genbank accession No. CBK46760.1, dated May 13, 2010.
NCBI, NCBI reference sequence No. NP_002180.1, dated Apr. 21, 2013.
NCBI, PDB accession No. 1UZ6_F, dated Oct. 18, 2012.

O'Conner et al., "Adoptive T-cell therapy improves treatment of canine non-Hodgkin lymphoma post chemotherapy", *Sci Rep.*, 2: 249, 2012.

Pabo et al., "Design and selection of novel $Cys_2His_2$ zinc finger proteins", *Annu. Rev. Biochem.*, 70: 313-40, 2001.

Parham, "MHC class I molecules and KIRS in human history, health and survival", Nature Reviews Immunology, 5: 201-214, 2005.

PCT International Preliminary Report on Patentability issued in International Application No. PCT/US2012/065506, mailed May 30, 2014.

PCT International Preliminary Report on Patentability issued in International Application No. PCT/US2014/039365, mailed Nov. 24, 2015.

PCT International Preliminary Report on Patentability issued in International Application No. PCT/US2014/038005, mailed Nov. 26, 2015.

PCT International Preliminary Report on Patentability issued in International Application No. PCT/US2014/062191, mailed Apr. 26, 2016.

(56) References Cited

OTHER PUBLICATIONS

PCT International Search Report and Written Opinion issued in International Application No. PCT/US2012/065506, mailed Mar. 4, 2013.
PCT International Search Report and Written Opinion issued in International Application No. PCT/US2014/039365, mailed Oct. 1, 2014.
PCT International Search Report and Written Opinion issued in International Application No. PCT/US2014/038005, mailed Feb. 13, 2015.
PCT International Search Report and Written Opinion issued in International Application No. PCT/US2014/062191, mailed Apr. 22, 2015.
PCT International Search Report and Written Opinion issued in International Application No. PCT/US2015/027511, mailed Jul. 29, 2015.
PCT International Search Report and Written Opinion issued in International Application No. PCT/US2015/027277, mailed Aug. 4, 2015.
PCT International Search Report and Written Opinion issued in International Application No. PCT/ US2015/059072, mailed Jan. 25, 2016.
PCT International Search Report and Written Opinion issued in International Application No. PCT/ US2015/059293, mailed May 3, 2016.
PCT Invitation to Pay Additional Fees issued in International Application No. PCT/US2016/021693, mailed May 19, 2016.
Porter et al., "Chimeric antigen receptor-modified T cells in chronic lymphoid leukemia", *The New England Journal of Medicine*, 365(8): 725-733, 2011.
Provasi et al., "Editing T cell specificity towards leukemia by zinc finger nucleases and lentiviral gene transfer", *Nature Medicine*, 18(5): 807-815, 2012.
Pule et al., "Virus-specific T cells engineered to coexpress tumor-specific receptors: persistence and antitumor activity in individuals with neuroblastoma", *Nat. Med.*, 14:1264-1270, 2008.
Ramos et al., "Chimeric antigen receptor (CAR)-engineered lymphocytes for cancer therapy", *Expert Opinion on Biological Therapy*,11(7): 855-873, 2011.
Riolobos et al., "HLA engineering of human pluripotent stem cells", *Molecular Therapy*, 21(6): 1232-1241, 2013.
Riteau et al., "HLA-G1 co-expression boosts the HLA class I-mediated NK lysis inhibition", *International Immunology*, 13(2): 193-201, 2001.
Rouas-Freiss et al., "The $\alpha_1$ domain of HLA-G1 and HLA-G2 inhibits cytotoxicity induced by natural killer cells: is HLA-G the public ligand for natural killer cell inhibitory receptors?", *Proc. Natl. Acad. Sci. USA*, 94: 5249-5254, 1997.
Rowley et al., "Expression of IL-15RA or an IL-15/IL-15RA fusion on CD8+ T cells modifies adoptively transferred T-cell function in cis", *European Journal of Immunology*, 39(2): 491-506, 2009.
Rushworth et al., "Universal artificial antigen presenting cells to selectively propagate T cells expressing chimeric antigen receptor independently of specifity", *J Immunother.*, 37(4): 204-13, 2014.
Sadelain et al., "The basic principles of chimeric antigen receptor design", *Cancer Discovery*, 3(4): 388-398, 2013.
Schomack et al., "Gene-for-gene-mediated recognition of nuclear-targeted AvrBs3-like bacterial effector proteins", *Journal of Plant Physiology*, 163: 256-272, 2006.
Segal and Barbas, "Customs DNA-binding proteins come of age: polydactyl zinc-finger proteins", *Current Opinion in Biotechnology*, 12: 632-637, 2001.
Shen et al., "Chimeric antigen receptor containing ICOS signaling domain mediates specific and efficient antitumor effect of T cells against EGFRvIII expressing glioma", *Journal of Hematology and Oncology*, 6(1): 33, 2013.
Singh et al., "Manufacture of clinical-grade CD19-specific T cells stably expressing chimeric antigen receptor using Sleeping Beauty system and artificial antigen presenting cells", *PLoS One.*, 8(5): e64138, 2013.
Singh et al., "Redirecting specificity of T-cell populations for CD19 using the Sleeping Beauty system", *Cancer Res.*, 68(8): 2961-2971, 2008.
Singh et al., "Reprogramming CD19-specific T cells with IL-21 signaling can improve adoptive immunotherapy of B -lineage malignancies", *Cancer Res.*, 71(10): 3516-3527, 2011.
Somanchi et al., "Engineering lymph node homing of ex vivo-expanded human natural killer cells via trogocytosis of the chemokine receptor CCR7", *Blood*, 119(22): 5164-5172, 2012.
Tamada et al., "Redirecting gene-modified T cells toward various cancer types using tagged antibodies", *Clinical Cancer Research*, 12(23): 6436-6445, 2012.
Till et al., "Adoptive immunotherapy for indolent non-Hodgkin lymphoma and mantle cell lymphoma using genetically modified autologous CD20-specific T cells", *Blood*, 112:2261-2271, 2008.
Torikai et al., "A foundation for universal T-cell based immunotherapy: T cells engineered to express a CD19-specific chimeric-antigen-receptor and eliminate expression of endogenous TCR", *Blood*, 119(24):5697-5705, 2012.
Torikai et al., "HLA and TCR knockout by zinc finger nucleases: toward "off-the-shelf" allogeneic t-cell therapy for CD19$^+$ malignancies", *Blood* (*ASH Annual Meeting Abstracts*), 116: Abstract 3766, 2010.
Torikai et al., "Toward eliminating HLA class I expression to generate universal cells from allogeneic donors", *Blood*, 122(8): 1341-1349, 2013.
Villard et al., "A functionally essential domain of RFX5 mediates activation of major histocompatibility complex class II promoters by promoting cooperative binding between RFX and NF-Y", *Molecular and Cellular Biology*, 20(10): 3364-3376, 2000.
Williams, "Sleeping beauty vector system moves toward human trials in the United States", *Mol. Ther.*, 16:1515-1516, 2008.
Zheng et al., "Protein L: a novel reagent for the detection of chimeric antigen receptor (CAR) expression by flow cytometry", *Journal of Translational Medicine*, 10:29, 2012.
Zhu et al., "Overexpression of miR-152 leads to reduced expression of human leukocyte antigen-G and increased natural killer cell mediated cytolysis in JEG-3 cells", *Am J Obstet Gynecol.*, 202(6): 592. e1-7, 2010.
Extended European Search Report issued in European Application No. 14801449.1, dated Jan. 31, 2017.

* cited by examiner

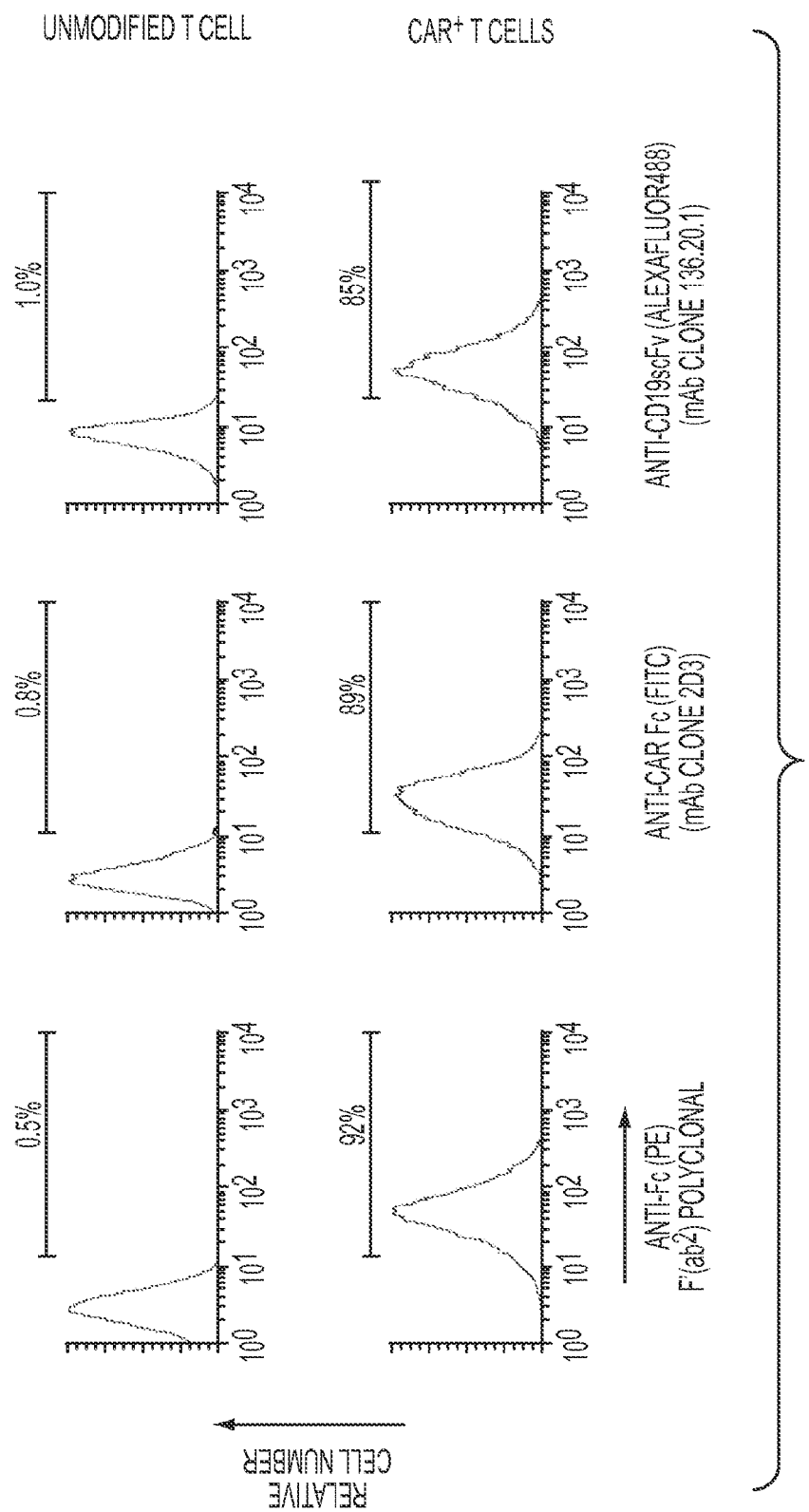

i) CAR⁺ T CELL (HnE) (40X)

ii) CAR-ⁿᵉᵍ T CELL (ANTI-CD19scFv) (40X)

iii) CAR⁺ T CELL (ANTI-CD19scFv) (40X)

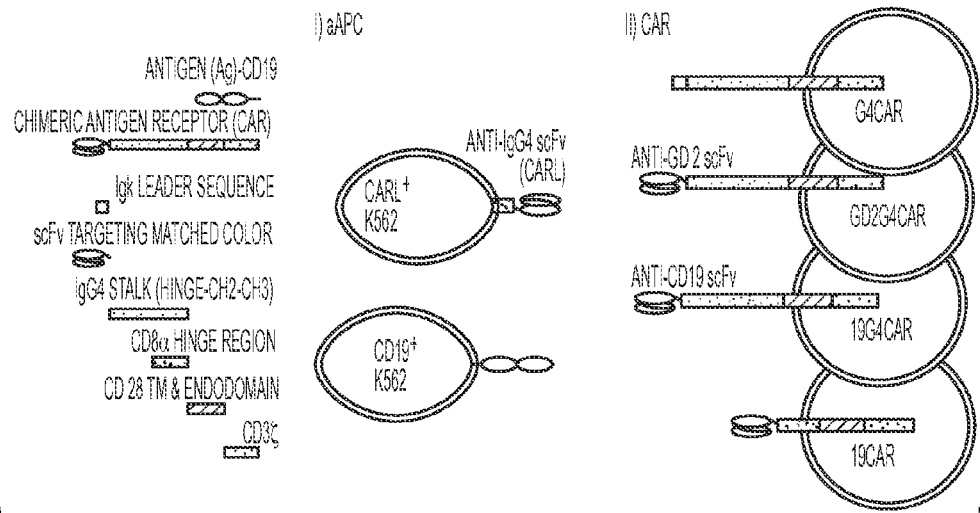
FIG. 14A
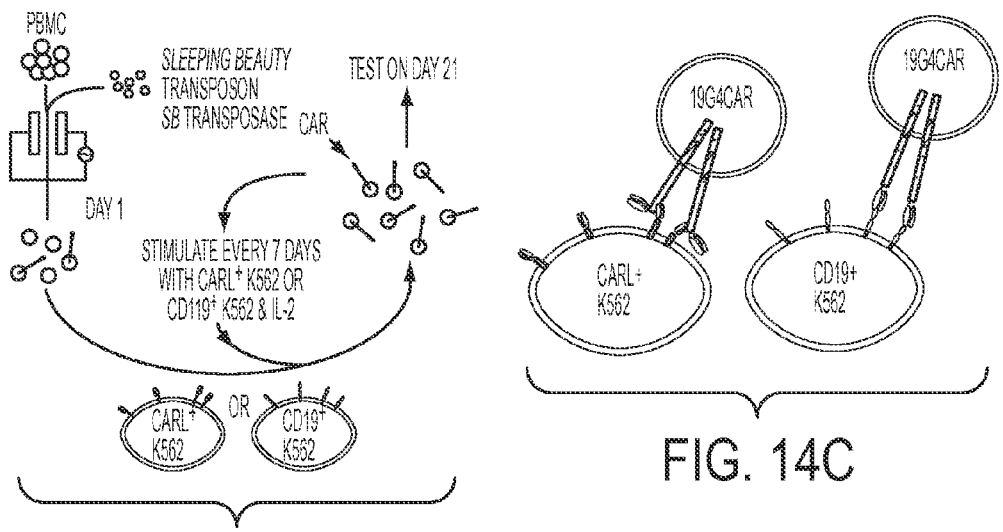
FIG. 14B
FIG. 14C

ANTI-CD19 SCFV (FMC63) POLYPEPTIDE

This application is a national phase application under 35 U.S.C. §371 of International Application No. PCT/US2014/039365, filed May 23, 2014, which claims the benefit of U.S. Provisional Patent Application No. 61/827,312 filed May 24, 2013. The entire text of each of the above referenced applications is incorporated herein by reference.

The invention was made with government support under Grant Nos. CA16672, CA124782, CA120956, CA141303, CA116127, and CA148600 awarded by the National Institutes of Health. The government has certain rights in the invention.

INCORPORATION OF SEQUENCE LISTING

The sequence listing that is contained in the file named "UTFC.P1221WO_ST25.txt", which is 23 KB (as measured in Microsoft Windows®) and was created on May 23, 2014, is filed herewith by electronic submission and is incorporated by reference herein.

BACKGROUND OF THE INVENTION

1. Field of the Invention

The present invention relates generally to the fields of medicine, molecular biology, immunology, and gene therapy. More particularly, it concerns CD19 chimeric-antigen receptor (CAR)-targeting and universal CAR-targeting monoclonal antibodies and methods of using the same.

2. Description of Related Art

Genetically modified T cells engineered to express a tumor-specific chimeric antigen receptor (CAR) have been infused initially with modest (Till et al., 2008; Pule et al., 2008; Morgan et al., 2010) and recently significant anti-tumor effects (Kochenderfer et al., 2010; Kalos et al., 2011; Brentjens et al., 2011; Kochenderfer et al., 2012; O'Connor et al., 2012). The prototypical CAR uses an extracellular domain to directly dock to a cell surface molecule, which is usually a tumor-associated antigen (TAA). The specificity of a CAR is typically derived from a scFv region assembled from the antigen-binding region of a TAA-specific monoclonal antibody (mAb). The components of a second generation CD19-specific CAR currently in use in clinical trials, designated CD19RCD28, are shown in FIG. 1A. The scFv from mouse mAb clone FMC63 (Nicholson et al., 1997) is fused in frame to an extracellular scaffold (e.g., human immunoglobulin hinge and Fc regions or hinge and constant regions from human CD8α) to promote oligomerization after binding TAA, which contributes to CAR-dependent activation via one or more signaling motifs in the endodomain.

Investigators measure the persistence of adoptively transferred T cells in vivo to assess the therapeutic potential of CAR+ T cells (Kalos et al., 2011; June et al., 2009). The most common approach to assessing survival of infused CAR+ T cells is quantitative PCR using CAR-specific primers (Kochenderfer et al., 2010; Morgan et al., 2006). However, this technique does not allow retrieval of genetically modified T cells from the recipient for multi-parameter analyses. What is needed, and is provided herein, is a mAb to specifically detect and isolate CD19-specific CAR+ genetically modified T cells. In addition to informing on persistence, a CAR-specific mAb can be used for in-process testing during manufacture to assess expression of the transgene, such as after electro-transfer of Sleeping Beauty (SB) or piggyBac DNA plasmids coding for CD19RCD28 (Singh et al., 2008; Manuri et al., 2009; Hackett et al., 2010; Singh et al., 2011).

Furthermore, two different reagents for the detection of CAR-modified T cells are known. Brentjens et al. (2013) describes the use of a biotinylated goat anti-mouse IgG (Fab')$_2$ (Jackson ImmunoReseach) for detection of CAR-modified T cells. As the sensitivity of this polyclonal antibody is low, in the setting of low lymphocyte numbers in patient samples, detection of CAR-modified T cells was accomplished only after non-specific expansion of T cells using Dynabeads. This prevents a direct assessment of circulating CAR-modified T cell in vivo after infusion. Zheng et al. (2012) describes the use of Protein L for detection of CAR-modified T cells by flow cytometry. This reagent has restricted use in terms of detection and sensitivity in a multi-parameter flow cytometry assay. Its use in other assay formats has not been shown. Importantly, both of these reagents are used for detection purposes only and their functionality has not been shown. Thus, there remains a need for reagents that specifically target CAR expressing cells for analysis and manipulation of the cell populations.

SUMMARY OF THE INVENTION

Embodiments of the invention provide monoclonal antibodies that specifically bind to a CAR polypeptide. For example, in some aspects, an antibody of the embodiments specifically binds to a constant domain of a CAR polypeptide. In alternative aspects, the antibody specifically binds to the antigen recognition domain of a CAR polypeptide (e.g., a CD-19-binding CAR polypeptide).

In a first embodiment an antibody is provided that binds specifically to a CD19-targeted CAR polypeptide (e.g., the polypeptide of SEQ ID NO: 17). In some aspects, an isolated and/or recombinant antibody binds to a CD19-specific scFv CAR polypeptide and competes for binding of the polypeptide with the 136.20.1 monoclonal antibody. In certain aspects, the antibody comprises all or part of the heavy chain variable region and/or the light chain variable region of the 136.20.1 monoclonal antibody. Thus, in some aspects, the antibody comprises an amino acid sequence that corresponds to a first, second, and/or third complementarity determining region (CDR) from the light variable and/or heavy variable chain of the 136.20.1 monoclonal antibody of the present embodiment. In one aspect, the antibody may be the 136.20.1 antibody.

In certain aspects, the isolated antibody comprises CDR sequences at least 80%, 85%, 90%, 91%, 92%, 93%, 94%, 95%, 96%, 97%, 98%, or 99% identical to the CDRs of the 136.20.1 monoclonal antibody heavy and light chain amino acid sequences (e.g., between 80% and 99% identical). In further aspects, an antibody comprises CDRs identical to the 136.20.1 CDRs, except for one, two or three amino acid substitutions, deletions, or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of a 136.20.1 monoclonal antibody. Thus is some specific aspects, an antibody of the embodiment comprises a first $V_H$, a second $V_H$, a third $V_H$, a first $V_L$, a second $V_L$, and a third $V_L$ CDR sequence at least 80% identical to the corresponding CDR sequence of monoclonal antibody 136.20.1, which are represented by SEQ ID NOs: 2, 3, 4, 6, 7, and 8, respectively. In some aspects, the isolated antibody comprises CDR sequences that are identical to the CDR sequences of monoclonal antibody 136.20.1.

In another aspect, the isolated antibody comprises a $V_H$ domain at least about 80%, 85%, 90%, 91%, 92%, 93%, 94%, 95%, 96%, 97%, 98%, or 99% identical to the $V_H$ domain of 136.20.1 (SEQ ID NO: 1) and/or a $V_L$ domain at least about 80%, 85%, 90%, 91%, 92%, 93%, 94%, 95%, 96%, 97%, 98%, or 99% identical to the $V_L$ domain of 136.20.1 (SEQ ID NO: 5). In other aspects, the isolated antibody comprises a $V_H$ domain between 80% and 99% identical to the $V_H$ domain of 136.20.1 (SEQ ID NO: 1) or a $V_L$ domain between 80% and 99% identical to the $V_L$ domain of 136.20.1 (SEQ ID NO: 5). In a further aspect, the isolated antibody comprises $V_H$ and $V_L$ domains identical to those of monoclonal antibody 136.20.1.

In a further embodiment, there is provided a recombinant polypeptide comprising an antibody $V_H$ domain comprising CDRs 1-3 of the $V_H$ domain of 136.20.1 (SEQ ID NOs: 2, 3 and 4). In another embodiment, there is provided a recombinant polypeptide comprising an antibody $V_L$ domain comprising CDRs 1-3 of the $V_L$ domain of 136.20.1 (SEQ ID NOs: 6, 7 and 8). In still further embodiments, there is provided an isolated polynucleotide molecule comprising nucleic acid sequence encoding an antibody or a polypeptide comprising an antibody $V_H$ or $V_L$ domain disclosed herein.

In yet further embodiments, there is provided a method for selecting a cell comprising a specific CAR polypeptide comprising contacting the cell with an antibody specifically binds to the antigen recognition domain of the CAR polypeptide and selecting a cell comprising the specific CAR based on binding of the antibody. For example, the antibody may be contacted with the cell to inhibit the effector activity of the cell (e.g., to block in vitro or in vivo activity). In further aspects, the antibody may be conjugated to a toxin for use in selectively inhibiting or killing a cell comprising a specific CAR polypeptide. In certain aspects, the specific CAR polypeptide can be a CD-19-binding CAR polypeptide. Thus, in some aspects, the antibody can be an antibody that binding the antigen recognition domain of a CD-19-binding CAR polypeptide, such as one of the specific antibodies disclosed herein.

In further embodiments, a method is provided for purifying or enriching cells comprising a specific CAR polypeptide. In some aspects, the antibody comprises a tag, such as a reporter, and the method comprises selecting cells comprising a specific CAR polypeptide (e.g., by fluorescence-activated cell sorting (FACS) and/or paramagnetic beads). In further aspect, an antibody may be bound to a support. The support may be, without limitation, a bead, a surface, a column, or an antigen presenting cell (APC) (e.g., an aAPC or an activating and propagating cell (AAPC)). In some aspects, a method for purifying, enriching or stimulating proliferation of cells comprises use of cells that express a specific CAR, such as CD19-specific scFv CAR. In some aspects, a method of the embodiments is further defined as a method for preventing or modifying the ability of a specific CAR (e.g., a CD-19-binding CAR) to activate a T cell by contacting the cell with an antibody that binds to the antigen recognition domain of the CAR. In a further aspect, a method is further defined as a method for controlling toxicity of a cell (e.g., controlling toxicity of a CAR T-cell therapy in a human subject).

Thus, in a further embodiment, there is provided a cell culture system comprising mammalian T-cells expressing a specific CAR and an antibody in accordance with the embodiments. In yet another embodiment, there is provided a kit comprising an antibody or cell of the embodiments and at least a first agent for increasing proliferation of mammalian T cells expressing a specific CAR (e.g., a cytokine or inactivated aAPCs). In still a further embodiment there is provided a recombinant cell expressing an antibody that specifically binds to the antigen recognition domain of a CAR. In some aspects, the antibody is a membrane-bound antibody. In still further aspects, the antibody is a scFv antibody. For example, in some specific embodiments cell (e.g., an APC) comprises a membrane-bound antibody comprising one, two, three, four or more of: (i) a GM-CSF leader peptide (e.g., amino acids 1-22 of SEQ ID NO: 22); (ii) the scFv coding sequence for an antibody that specifically binds to the antigen recognition domain of a CAR (e.g., a CD-19-bding CAR); (iii) a CD8α linker sequence (e.g., amino acids 136-182 of SEQ ID NO: 23); (iv) a CD28 transmembrane domain (e.g., amino acids 56-123 of SEQ ID NO: 24); and/or (v) a CD3ξ intracellular domain (e.g., amino acids 48-163 of SEQ ID NO: 25).

In yet a further embodiment, the present invention provides an isolated or recombinant monoclonal antibody that specifically binds to the constant domain of a CAR polypeptide. For example, the antibody can compete for binding of the polypeptide with the 2D3 monoclonal antibody. In certain aspects, the antibody may comprise all or part of the heavy chain variable region and/or the light chain variable region of the 2D3 monoclonal antibody. In a further aspect, the antibody may comprise an amino acid sequence that corresponds to a first, second, and/or third complementarity determining region (CDR) from the light variable and/or heavy variable chain of the 2D3 monoclonal antibody of the present embodiment. In one aspect, the antibody may be the 2D3 antibody. In still further aspects, an antibody of the embodiments (e.g., a 2D3 monoclonal antibody) binds to a polypeptide comprising the sequence of SEQ ID NO: 18.

Thus, in certain aspects, the isolated antibody comprises CDR sequences at least 80%, 85%, 90%, 91%, 92%, 93%, 94%, 95%, 96%, 97%, 98%, or 99% identical to the CDRs of the 2D3 monoclonal antibody heavy and light chain amino acid sequences. In further aspects, an antibody comprises CDRs identical to the 2D3 CDRs, except for one, two or three amino acid substitutions, deletions, or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of a 2D3 monoclonal antibody. Thus, is some specific aspects, an antibody of the embodiment comprises a first $V_H$, a second $V_H$, a third $V_H$, a first $V_L$, a second $V_L$, and a third $V_L$ CDR sequence at least 80% identical to the corresponding CDR sequence of monoclonal antibody 2D3, which are represented by SEQ ID NOs: 10, 11, 12, 14, 15, and 16, respectively. In certain aspects, the antibody comprises CDR sequences that are identical to the CDR sequences of monoclonal antibody 2D3. In certain aspects, such an antibody is a humanized or de-immunized antibody comprising the foregoing CDRs on a human IgG (e.g., IgG1 or IgG2) backbone.

In another aspect, the isolated antibody comprises a $V_H$ domain at least about 80%, 85%, 90%, 91%, 92%, 93%, 94%, 95%, 96%, 97%, 98%, or 99% identical to the $V_H$ domain of 2D3 (SEQ ID NO: 9) and a $V_L$ domain at least about 80%, 85%, 90%, 91%, 92%, 93%, 94%, 95%, 96%, 97%, 98%, or 99% identical to the $V_L$ domain of 2D3 (SEQ ID NO: 13). In certain aspects, the isolated antibody comprises a $V_H$ domain between 80% and 99% identical to the $V_H$ domain of 2D3 (SEQ ID NO: 9) or a $V_L$ domain between 80% and 99% identical to the $V_L$ domain of 2D3 (SEQ ID NO: 13). In some aspects, the isolated antibody comprises $V_H$ and $V_L$ domains identical to those of monoclonal antibody 2D3.

In a further embodiment, there is provided a recombinant polypeptide comprising an antibody $V_H$ domain comprising CDRs 1-3 of the $V_H$ domain of 2D3 (SEQ ID NOs: 10, 11 and 12) or a recombinant polypeptide comprising an antibody $V_L$ domain comprising CDRs 1-3 of the $V_L$ domain of 2D3 (SEQ ID NOs: 14, 15 and 16). In still further embodiments, there is provided an isolated polynucleotide molecule comprising nucleic acid sequence encoding an antibody or a polypeptide comprising an antibody $V_H$ or $V_L$ domain disclosed herein.

In yet further embodiments, there is provided a method for selecting a cell comprising a CAR polypeptide comprising contacting the cell with an antibody (e.g., such as those disclosed herein) that binds to the constant domain of a CAR polypeptide and selecting a cell comprising the CAR based on binding of the antibody. In certain aspects, the antibody may be conjugated to a toxin for use in selectively inhibiting or killing a cell comprising a CAR. Thus, in some aspect, a method is provided for inhibiting or killing a CAR-expressing cell in vivo. In some aspects, a method of the embodiments is further defined as a method for preventing or modifying the ability of a CAR to activate a T cell by contacting the cell with an antibody that binds to the constant domain of the CAR. In a further aspect, a method is further defined as a method for controlling toxicity of a cell (e.g., controlling toxicity of a CAR T-cell therapy in a human subject).

In still a further embodiment there is provided a recombinant cell expressing an antibody that binds to the constant domain of a CAR. In some aspects, the antibody is a membrane-bound antibody. In still further aspects, the antibody is a scFv antibody. For example, in some specific embodiments cell (e.g., an APC) comprises a membrane-bound antibody comprising one, two, three, four or more of: (i) a GM-CSF leader peptide (e.g., amino acids 1-22 of SEQ ID NO: 22); (ii) the scFv coding sequence for an antibody that binds to the constant domain of a CAR (e.g., a 2D3 scFv coding sequence); (iii) a CD8α linker sequence (e.g., amino acids 136-182 of SEQ ID NO: 23); (iv) a CD28 transmembrane domain (e.g., amino acids 56-123 of SEQ ID NO: 24); and/or (v) a CD3 intracellular domain (e.g., amino acids 48-163 of SEQ ID NO: 25).

In certain aspects, a method for purifying or enriching cells comprising CAR using an antibody of the embodiments is provided. In one aspect, the antibody comprises a tag, such as a reporter, and the method comprises selecting cells comprising CAR (e.g., by FACS). In further aspects, the antibody may be bound to a support. The support may be, without limitation, a bead, a surface, a column, or an aAPC or AAPC. In some aspect, purifying or enriching cells comprising CAR comprises stimulating proliferation of the cells. Thus, in a further embodiment, there is provided a cell culture system comprising mammalian T-cells expressing a CAR and an antibody in accordance with the embodiments. In a further embodiment, there is provided a kit comprising an antibody of the embodiments and at least a first agent for increasing proliferation of mammalian T cells expressing a CAR. In one aspect, the kit may comprise inactivated aAPCs.

In still further aspects, CAR-binding antibody of the embodiments (e.g., a CAR constant domain-binding or CAR antigen recognition domain-binding antibody) is a humanized or de-immunized antibody comprising the foregoing CDRs on a human IgG (e.g., IgG1 or IgG2) backbone. In one aspect, the antibody may be recombinant. In further aspects, an antibody of the embodiments may be an IgG (e.g., IgG1, IgG2, IgG3 or IgG4), IgM, IgA, or an antigen binding fragment thereof. The antibody may be, for example, a Fab', a F(ab')2 a F(ab')3, a monovalent scFv, a bivalent scFv, or a single domain antibody. In some aspects, the antibody may be a human, humanized, or de-immunized antibody. In still further aspects, the antibody may be conjugated to an imaging agent, a chemotherapeutic agent, a toxin, a reporter, or a radionuclide.

In further embodiments, a host cell is provided that comprises one or more polynucleotide molecule(s) of the embodiments and/or that produces a monoclonal antibody or recombinant polypeptide of the embodiments. In some aspects, the host cell is a mammalian cell, a yeast cell, a bacterial cell, a ciliate cell, or an insect cell. In certain aspects, the host cell is a hybridoma cell. In certain aspects, the host cell is an artificial antigen presenting cell.

In still further embodiments, there is provided a method of manufacturing an antibody of the present invention comprising expressing one or more polynucleotide molecule(s) encoding a $V_L$ or $V_H$ chain of an antibody disclosed herein in a cell and purifying the antibody from the cell.

Certain embodiments of the invention are directed to an antibody or recombinant polypeptide composition comprising an isolated and/or recombinant antibody or polypeptide that specifically binds CAR or CD19-specific scFv CAR. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein or a combination of such sequences.

In still further aspects, an antibody or polypeptide of the embodiments comprises one or more amino acid segments of the any of the amino acid sequences disclosed herein. For example, the antibody or polypeptide can comprise 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 amino acids in length, including all values and ranges there between, that are at least 80, 85, 90, 95, 96, 97, 98, 99, or 100% identical to any of the amino acid sequences disclosed herein. In certain aspects the amino segment(s) are selected from one of the amino acid sequences of a CAR or CD19-specific scFv CAR binding antibody as provided in Tables 2 and 3.

In yet further aspects, an antibody or polypeptide of the embodiments comprises an amino acid segment that is at least 80, 85, 90, 95, 96, 97, 98, 99, or 100% identical (or any range derivable therein) to a V, VJ, VDJ, D, DJ, J or CDR domain of a CAR or CD19-specific scFv CAR antibody (as provided in Tables 2 and 3). For example, a polypeptide may comprise 1, 2 or 3 amino acid segment that are at least 80, 85, 90, 95, 96, 97, 98, 99, or 100% identical (or any range derivable therein) to CDRs 1, 2, and/or 3 a CAR or CD19-specific scFv CAR antibody as provided in Tables 2 and 3.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising," respectively.

As used herein in the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-C. Detection of CD19-specific CAR on the surface of genetically modified cells. (A) CAR$^+$ T cells were electroporated with SB system and propagated on aAPC. Upper row: Unmodified T cells as back ground control; Bottom row: CD19RCD28$^+$ T cells (labeled as CAR$^+$ T cells) detected by flow cytometry using clone no. 136.20.1, a commercially-available antibody (clone H10104, Invitrogen) that binds to the CAR hinge/Fc scaffold, and the inventor's own scaffold-specific mAb (clone 2D3). (B) Jurkat cells genetically modified to express CD19RCD28 were detected by clone no. 136.20.1 conjugated to ALEXA FLUOR® 488 dye and ALEXA FLUOR® 647 dye similar to commercial antibody (clone H10104). (C) Multi-parameter flow cytometry analysis of T cells that do and do not express CD19RCD28 as detected by clone no. 136.20.1. Sequential staining was performed, first with clone no. 136.20.1 and then other antibodies.

Sensitivity of clone no. 136.20.1 to detect CD19-specific CAR$^+$ T cells in PBMC. CD19-specific T cells expressing CD19RCD28 were serially diluted in PBMC (1:10 to 1:10, 000). (A) The upper panel shows background level signal in PBMC control. (B) Middle panel shows staining of CAR$^+$ T cells in undiluted sample. (C) Bottom panel shows lowest detection level (1:1,000) of CAR$^+$ T cells in PBMC. Data acquisition by FACSCALIBER™ cell analysis platform and plots were analyzed using FLOWJO® software. Shown in picture are representative flow cytometry data obtained from two independent experiments.

FIG. 5. Localization of CD19RCD28 CAR on the surface of genetically modified T cells. (A) Genetically-modified CAR$^+$ T cells (expressing CD19RCD28) and unmodified control T cells were fixed using paraformaldehyde, stained with ALEXA FLUOR® 647 dye-conjugated clone no. 136.20.1 mAb and then spread on glass slides using cytospin. Confocal images were acquisitioned by confocal microscope (60× magnification; Leica Microsystems). Upper panels (i and ii) show surface distribution of CAR molecules and bottom panels (iii and iv) show no staining in unmodified control T cells. Nuclear staining was by DAPI (pseudo-color green). The bar (1 µM) on images provides scale. (B) TEM images showing staining of gold-labeled nanoparticles conjugated to clone no. 136.20.1 mAb. Upper row: Unmodified control T cells (i) 120 nm thin section; 15 k magnification stained with uranyl acetate, (ii) 120 nm thin section; 75 k magnification, and (iii) 120 nm thin section; 200 k magnification. No gold particles were appreciated in these CAR$^{neg}$ T cells. Bottom row: CAR$^+$ T cells with enforced expression of CD19RCD28 (iv) 120 nm thin section stained with uranyl acetate; 20 k magnification, (v) 120 nm thin section; 200 k magnification, and (vi) 80 nm thin section 200K magnification. Arrow heads on plates v and vi indicate surface distribution of gold-labeled nanoparticles attached to CAR molecules. The bar indicates scale.

Figure 6A:
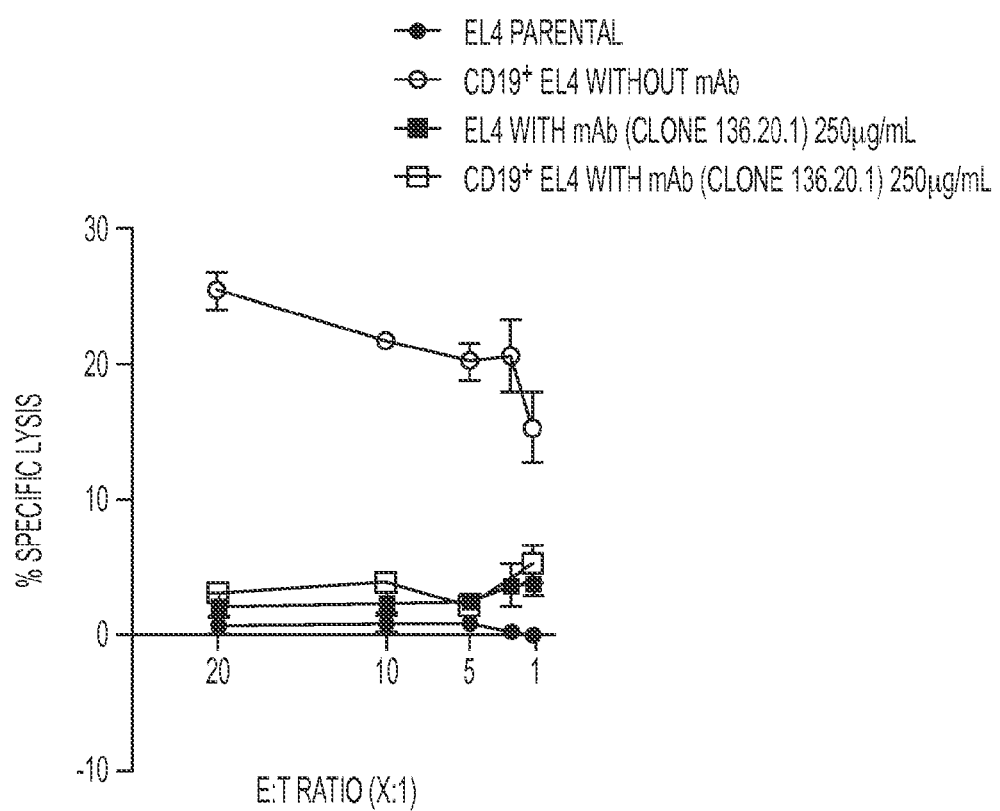
Figure 6B:
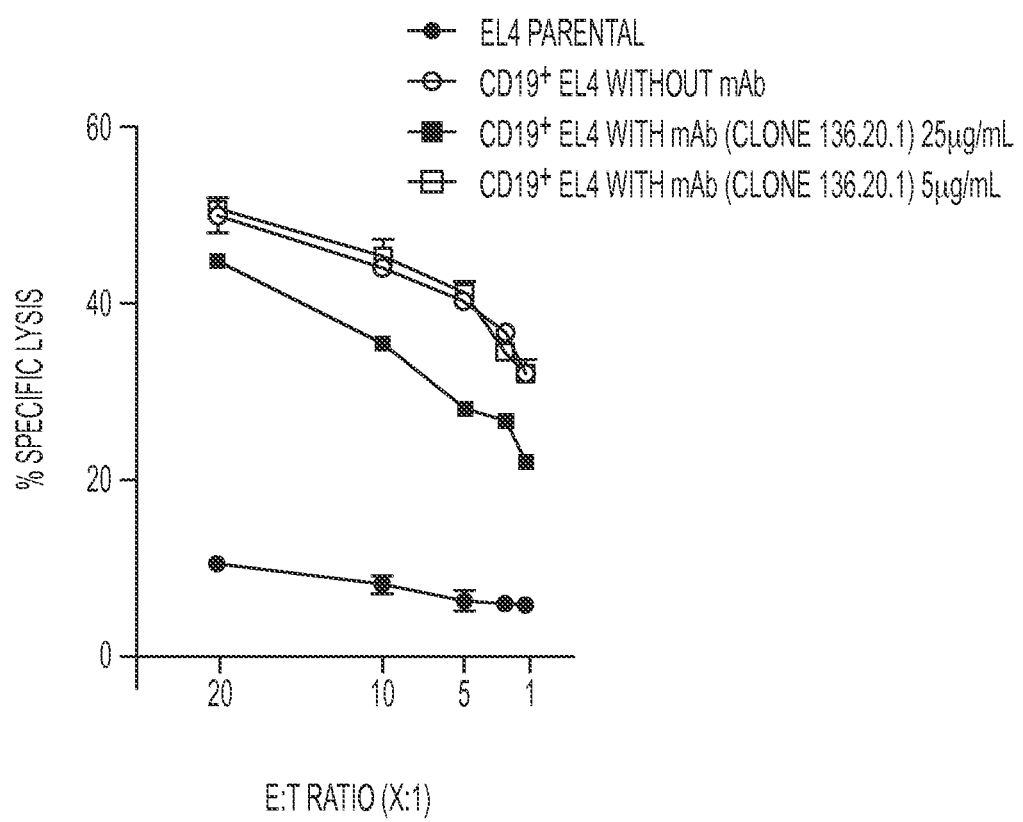
Figure 6C:
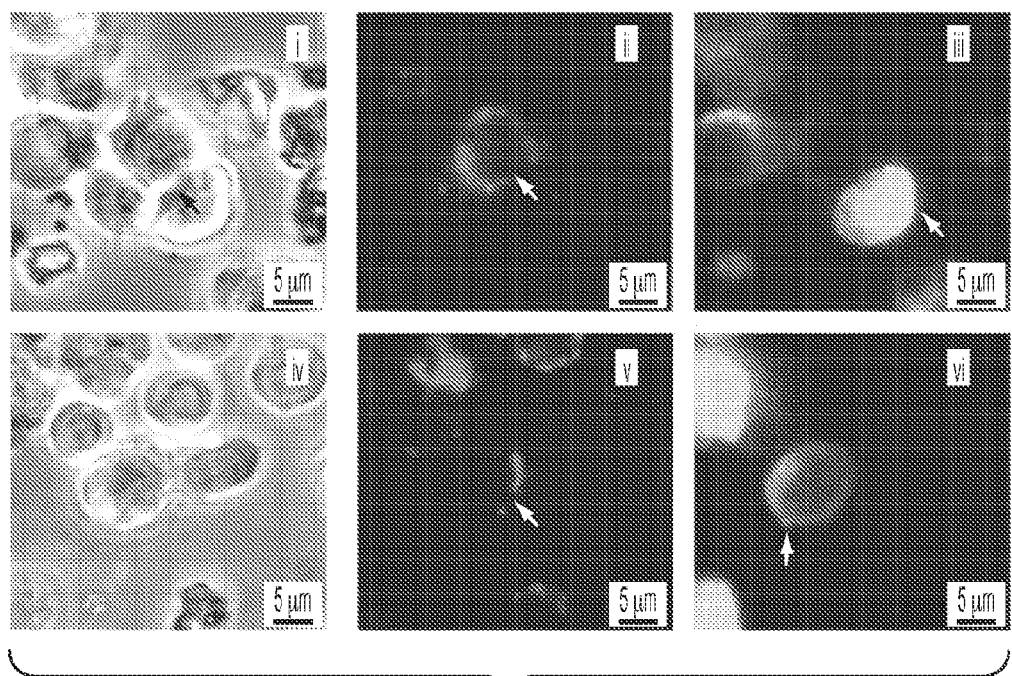

FIGS. 6A-C. Clone no. 136.20.1 inhibits CAR$^+$ T-cell effector function. (A) Data from CRA shows inhibition of tumor cell lysis in CD19$^+$ EL4 cells when CD19-specific CAR$^+$ T cells were blocked with clone no. 136.20.1 (B) Dose response curve showing clone no. 136.20.1-mediated inhibition of lysis of CD19$^+$ EL4 target cells. (C) Images obtained from VTLM showing CD19-specific CAR$^+$ T cells co-cultured with CD19$^+$ Daudiβ$_2$m expressing eGFP and stained with either clone no. 136.20.1 conjugated to ALEXA FLUOR® 647 dye or Fc mAb that recognizes CAR scaffold conjugated to PE. Images show two separate focal planes (at 2 and 90 minutes, respectively). Upper panels (i-iii) reveal coculture of Daudiβ$_2$m target cells with CAR$^+$ T cells in the presence of Fc-specific antibody. Lower panels (iv-vi) reveal coculture of Daudiβ$_2$m target cells with CAR$^+$ T cells in the presence of clone no. 136.20.1. Panels i-iv show phase contrast images of CAR$^+$ T cells along with Daudiβ$_2$m. Panels ii-v show formation of immunological synapse (yellow arrow heads) when CD19-specific CAR$^+$ T cells attack tumor cells. Panel iii shows killing of CD19$^+$ tumor cell by CD19-specific CAR$^+$ T cells as observed by formation of green fluorescence blub. Panel vi shows intact Daudiβ$_2$m cells when the CAR$^+$ T cells were blocked by clone no. 136.20.1 and no killing was observed even when effector T cells engaged the tumor cells for more than 6 hours. Shown are data from 3 independent experiments.

Figure 7:
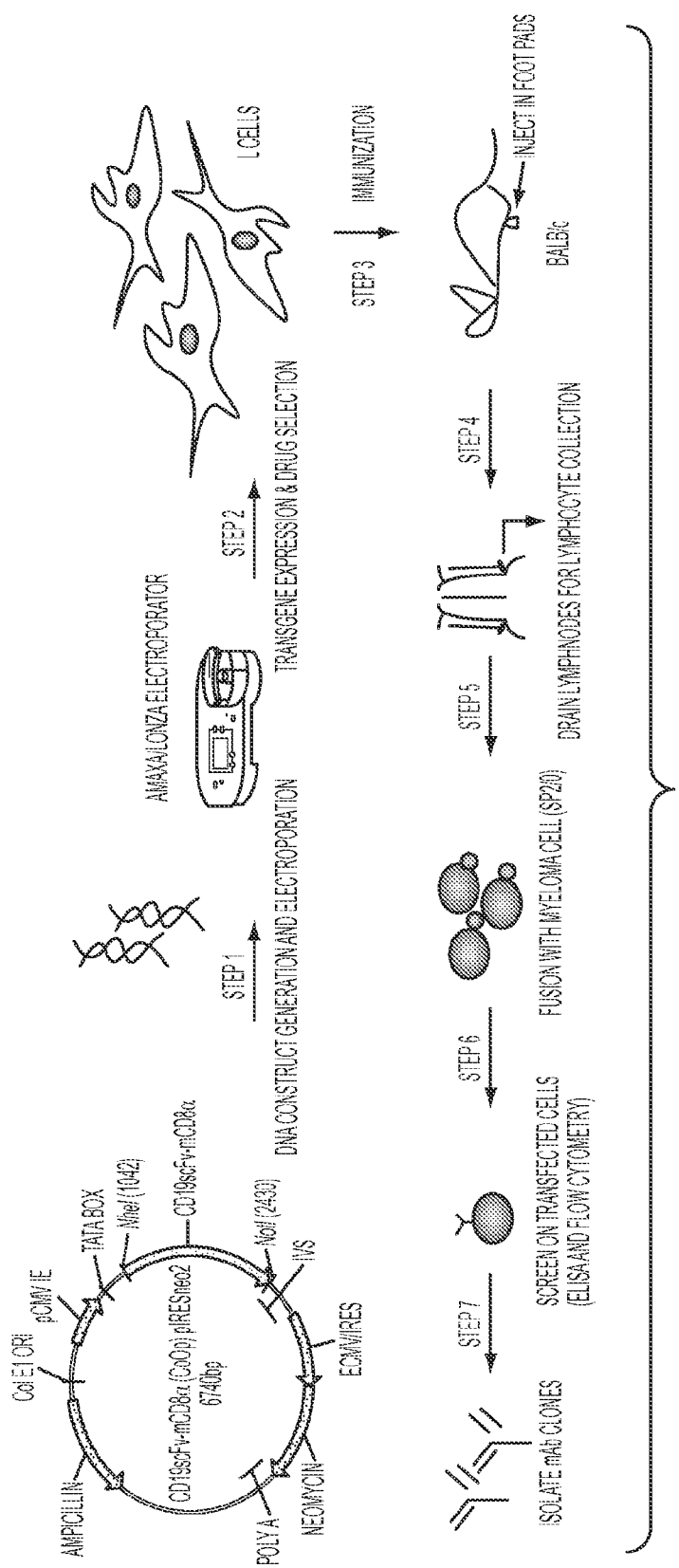
Figure 8A:
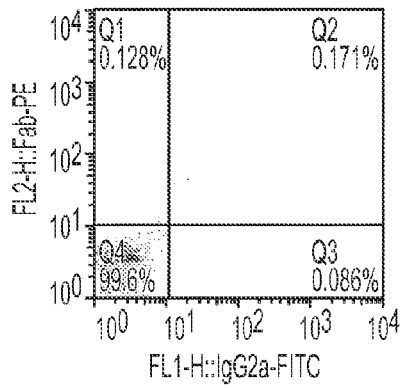
Figure 8B:
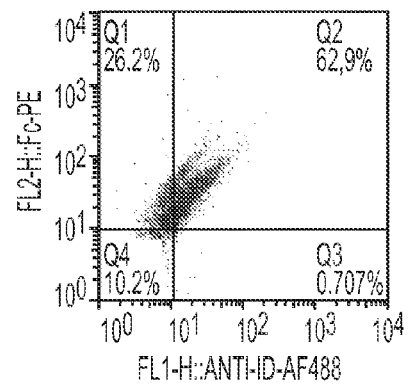
Figure 8C:
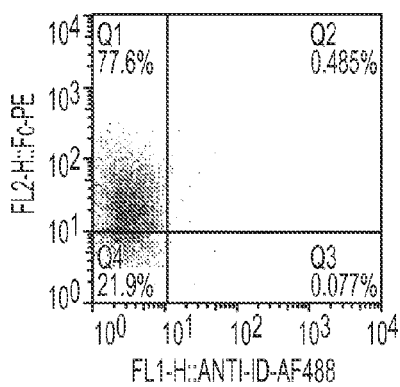
Figure 8D:
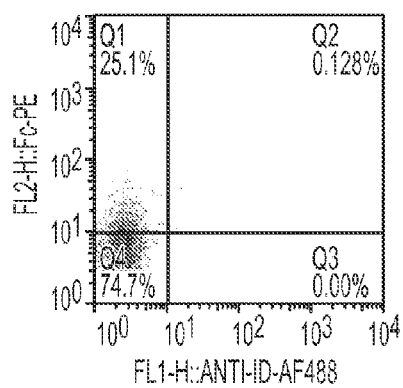
Figure 8E:
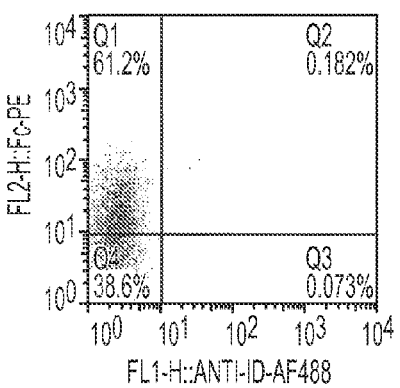
Figure 8F:
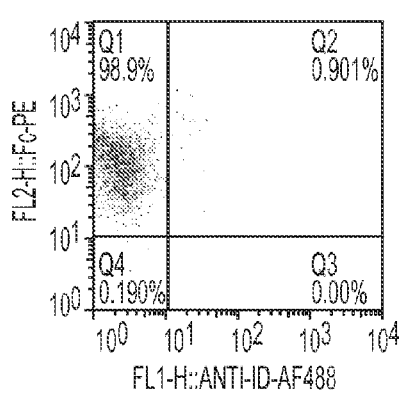

FIG. 7. Schematic describes the steps for generating clone no. 136.20.1 mAb by L-cell immunization. DNA plasmid encoding the scFv immunogen was introduced into L cells by an electroporator device (Lonza). L cells stably expressed the transgenes under G418 drug selection. BALB/c mice were immunized in the foot pad and draining lymph nodes were harvested to collect lymphocytes. Candidate hybridoma clones were isolated and expanded for isolation of mAb that could detect CD19-specific CAR that employs scFv region derived from FMC63.

FIG. 8. Specificity of anti-CD19scFv mAb (clone no. 136.20.1) towards CD19-specific CAR$^+$ T cells. A panel of CAR$^+$ T cells were collected and stained with a commercial Fc-specific antibody (goat Fab$_2$ anti-human Fc gamma-PE) followed by staining with anti-CD19scFv mAb-ALEXA FLUOR® 488 dye. Shown are (A) Isotype control, (B) CD19RCD28 CAR$^+$ T cells, (C) CD123-specific T cells (expressing CD123RCD28mZ-CAR), (D) CD33-specific T cells (expressing CD33RCD28z/Neo-CAR), (E) ROR1-specific T cells (expressing ROR1RCD137mz-CAR), and (F) HERV-K-specific T cells (expressing HERV-K-CD28z CAR). All cells were co-stained with Fc-specific antibody as well as clone no. 136.20.1. Only T cells expressing the CD19RCD28 CAR co-stained with both Fc-specific antibody and clone no. 136.20.1.

Figure 9:
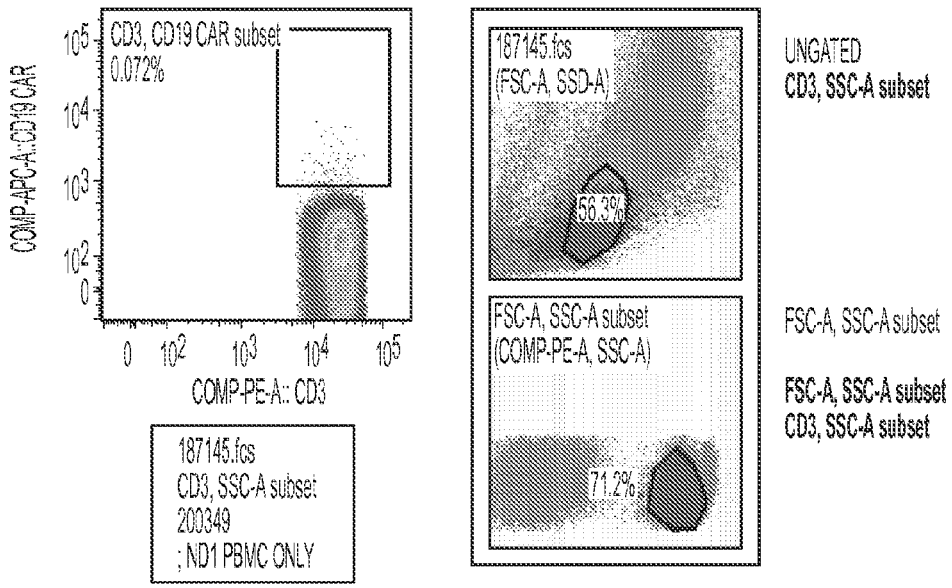
Figure 9:
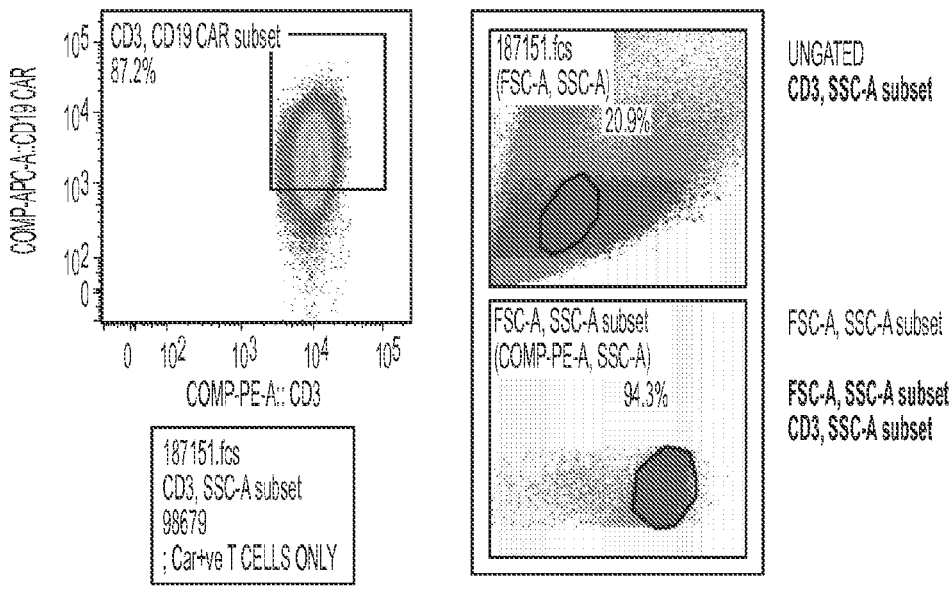
Figure 9:
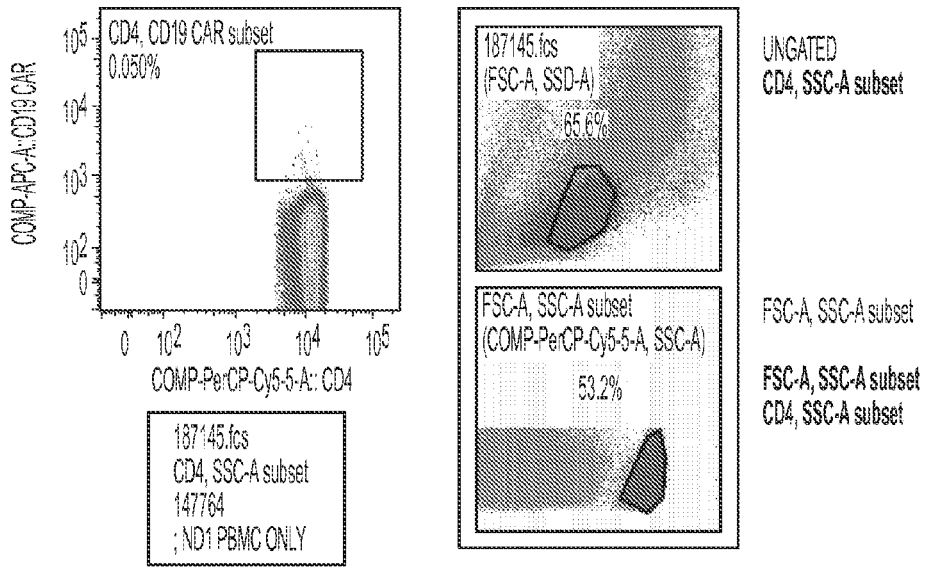
Figure 9:
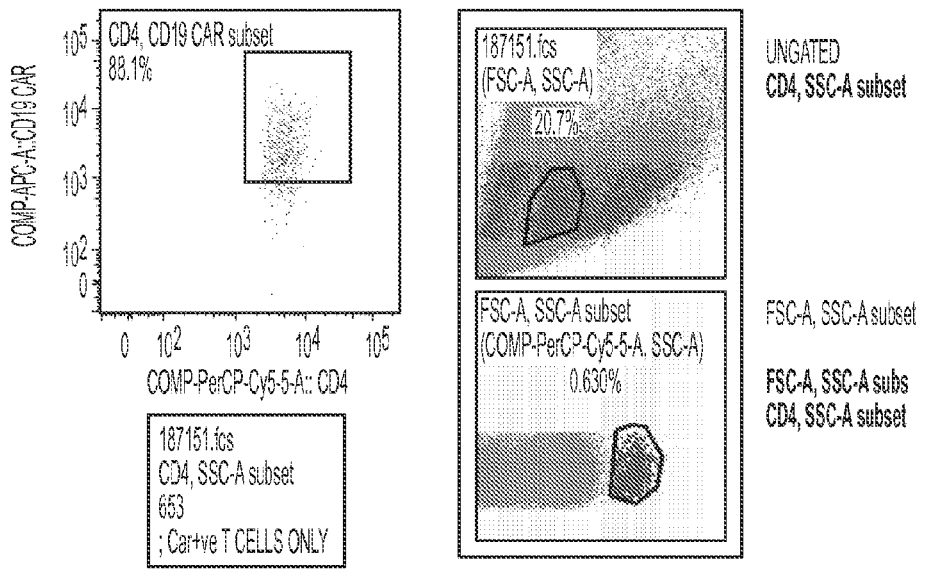
Figure 9:
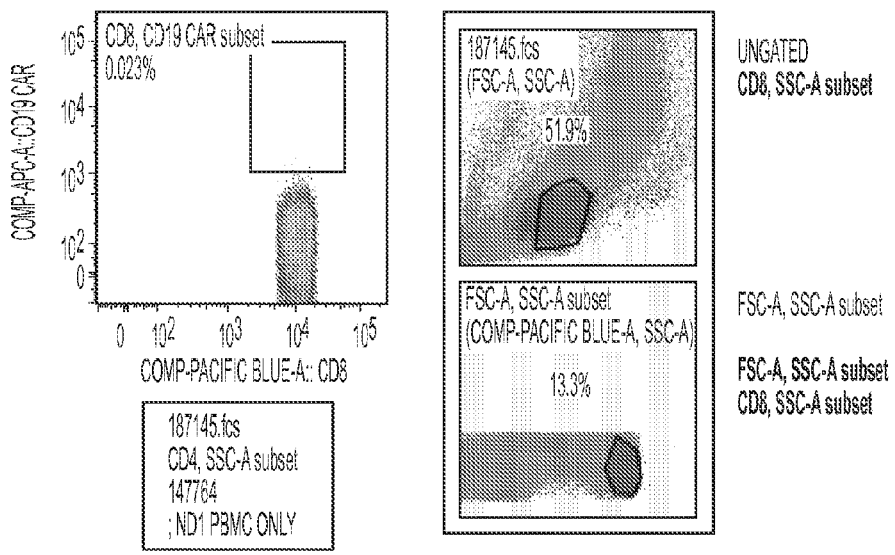
Figure 9:
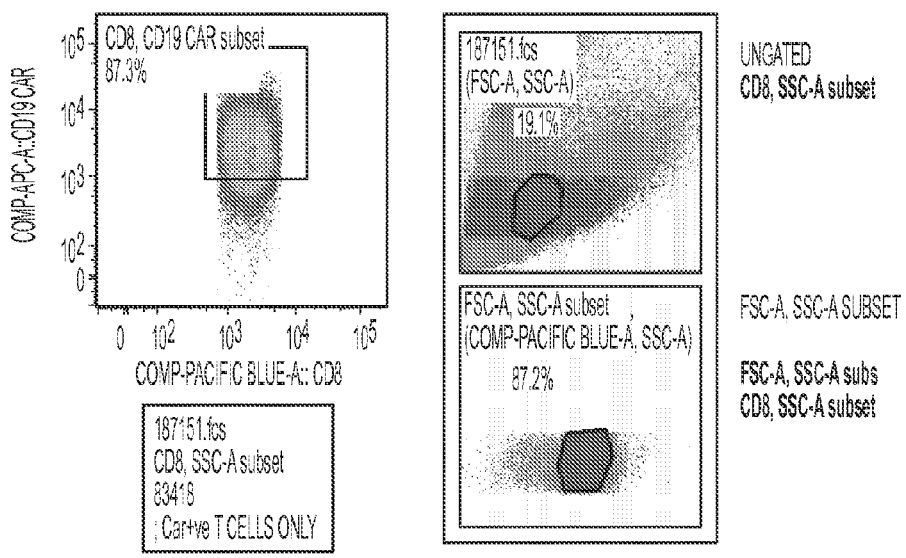
Figure 9:
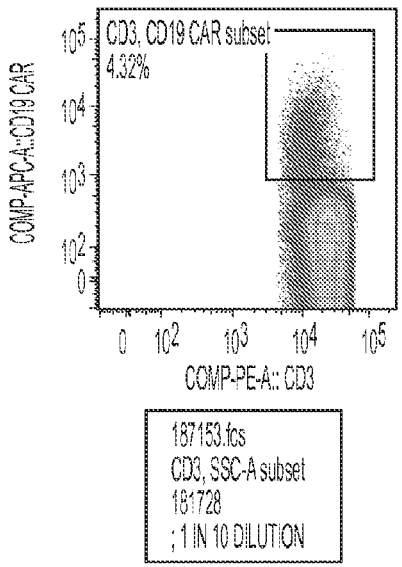
Figure 9:
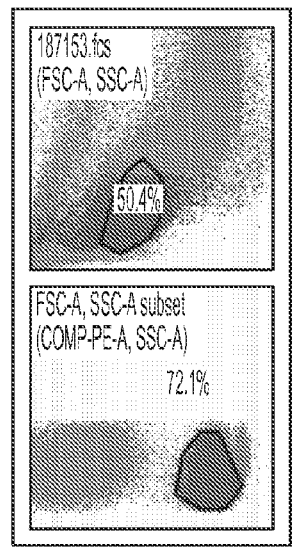
Figure 9:
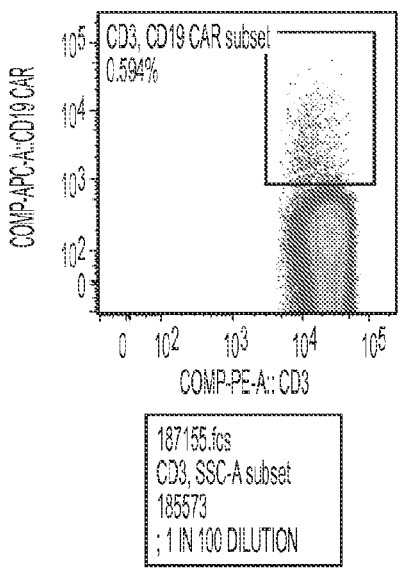
Figure 9:
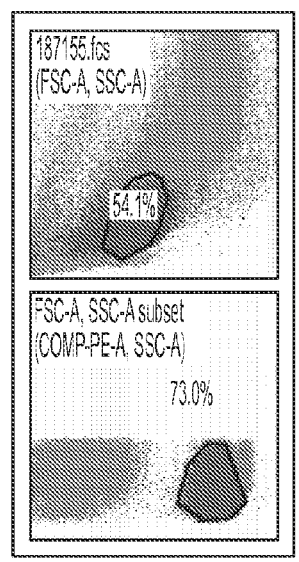
Figure 9:
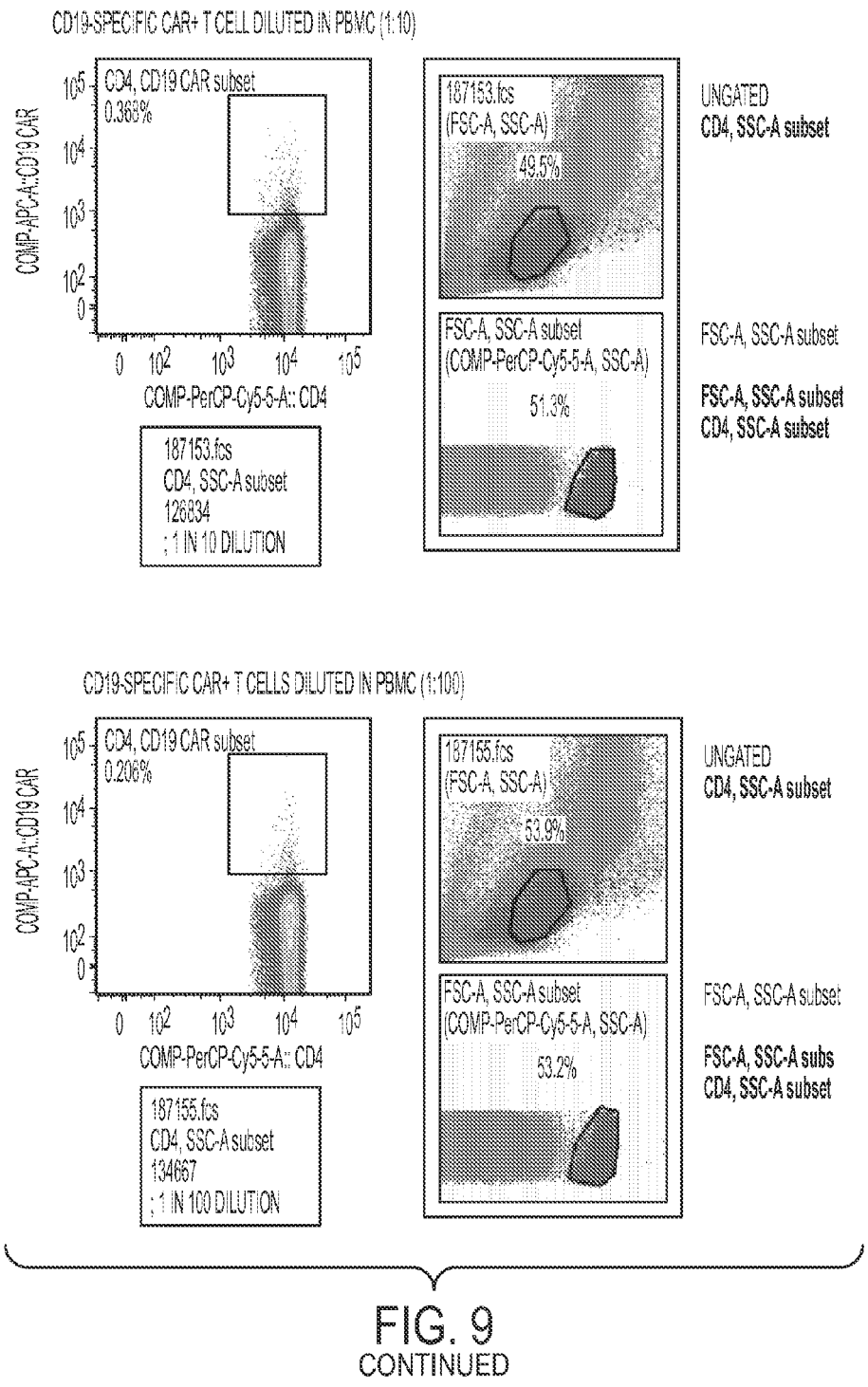
Figure 9:
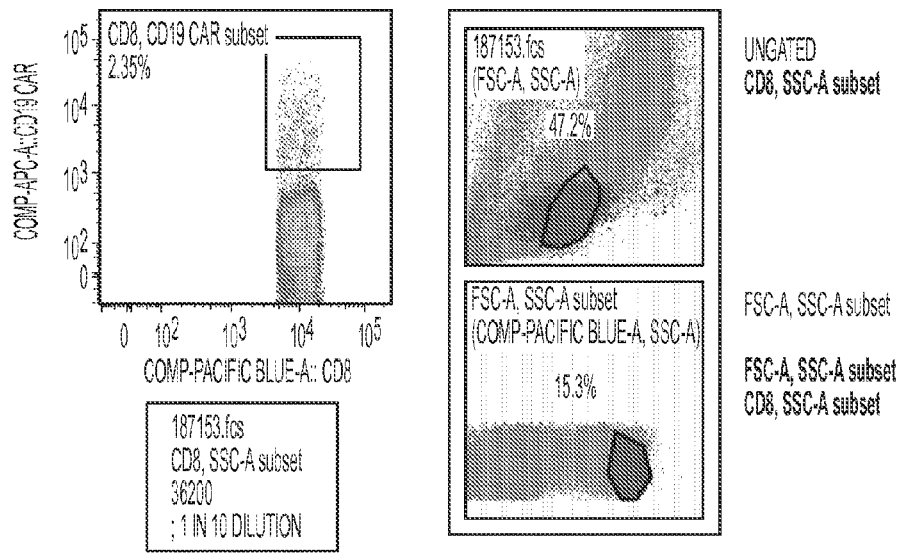
Figure 9:
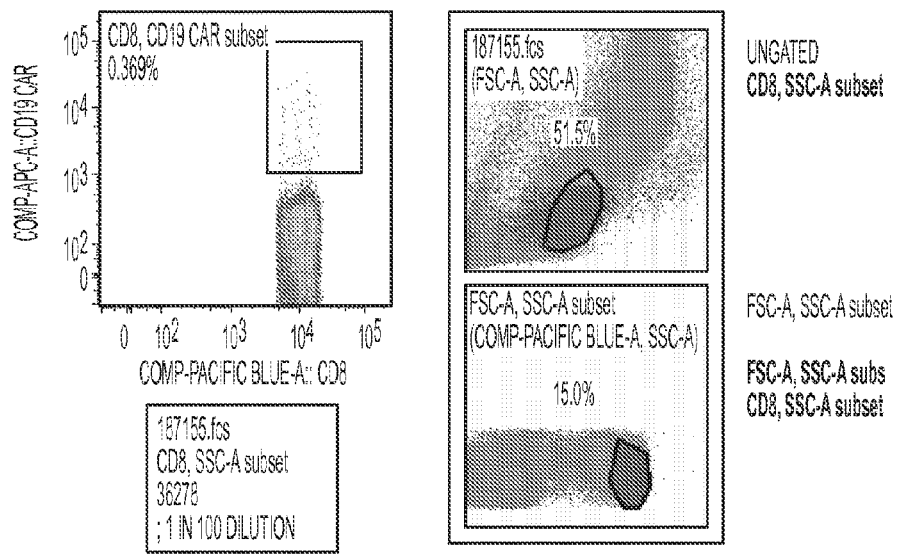
Figure 9:
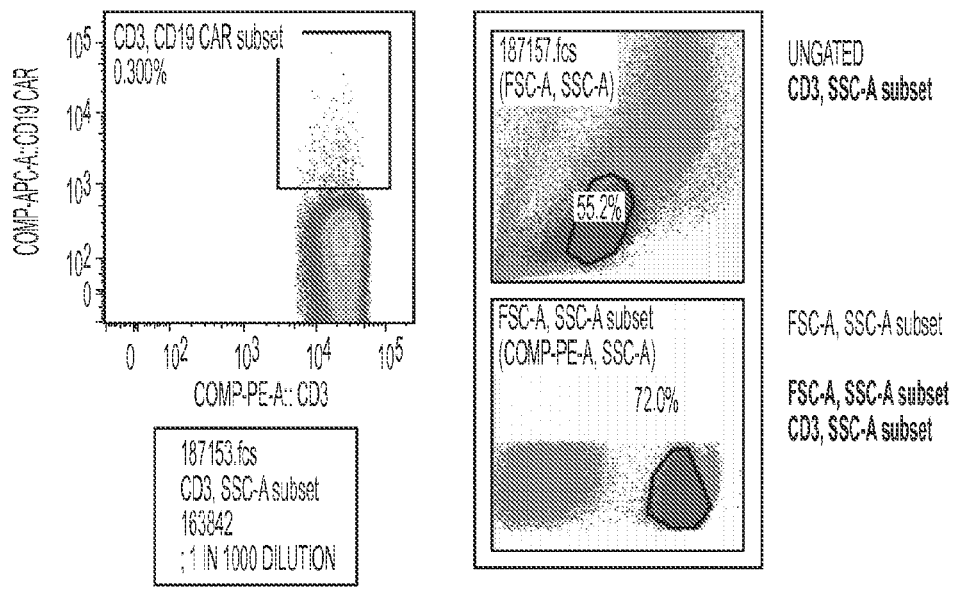
Figure 9:
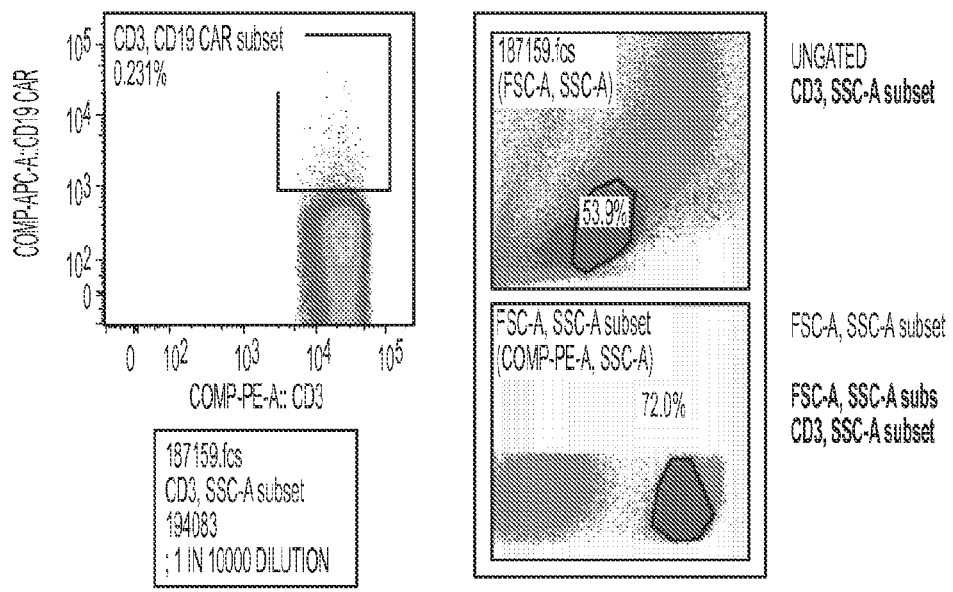
Figure 9:
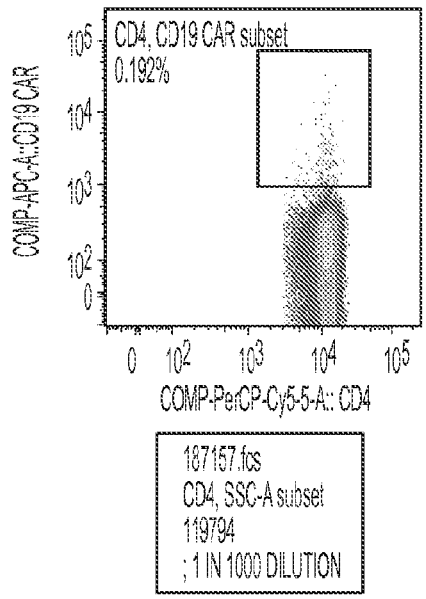
Figure 9:
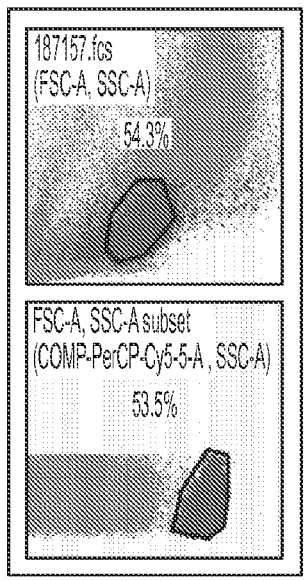
Figure 9:
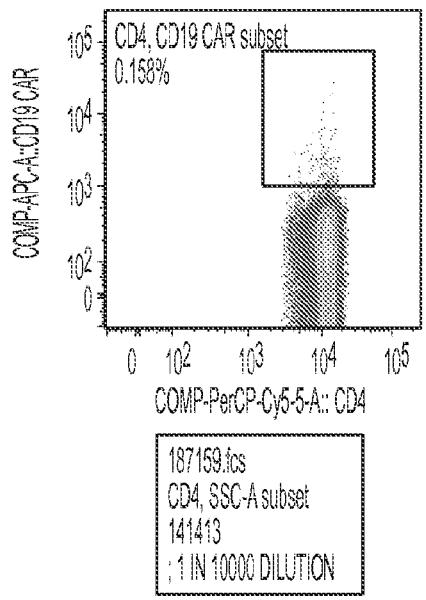
Figure 9:
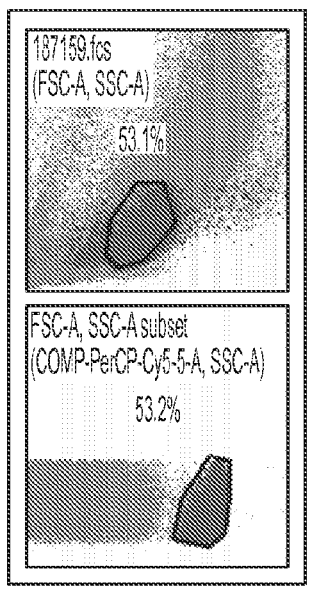
Figure 9:
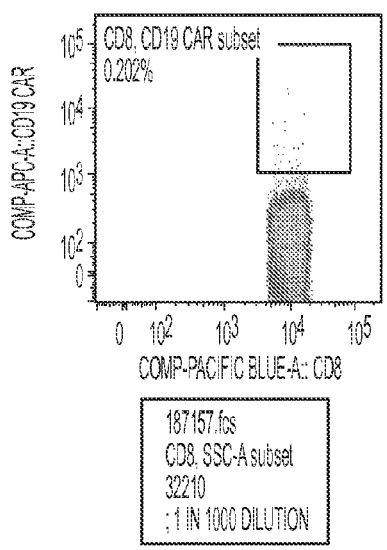
Figure 9:
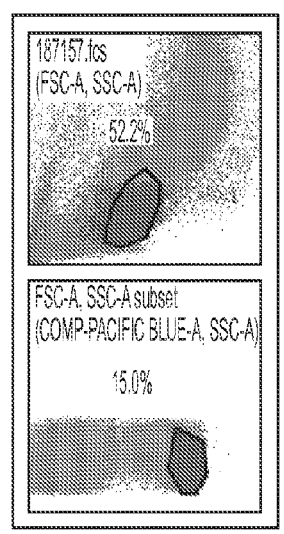
Figure 9:
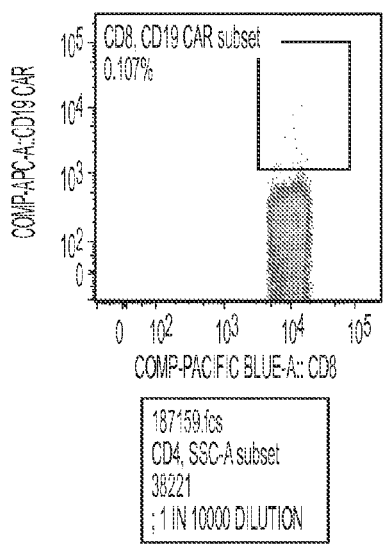
Figure 9:
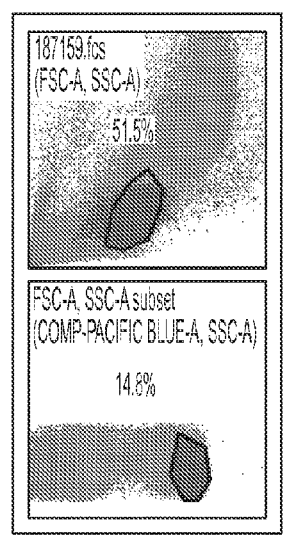

FIG. 9. Flow cytometry detection sensitivity of CD19-specific CAR$^+$ T cells mixed with PBMC from healthy volunteers. Shown are plots obtained from entire dilution range (1:10-1:10,000) of CAR$^+$ T cells mixed with PBMC. Cells after mixing, were gated on live Aqua stain (Life Tech) lymphocytes (primary gate), followed by positive gating on CD3$^+$, CD4$^+$, CD8$^+$ T cells (panels i, ii and iii, respectively) (secondary gate), and then identified as co-staining with ALEXA FLUOR® 647 dye-conjugated clone no. 136.20.1 mAb (tertiary gate). On left panel are CAR$^+$ T cells within specific lymphocyte population. Right panel shows back-gating within original lymphocyte population.

Figure 10:
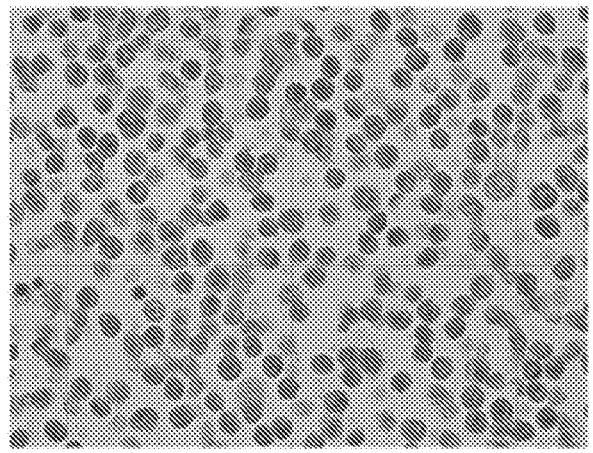
Figure 10:
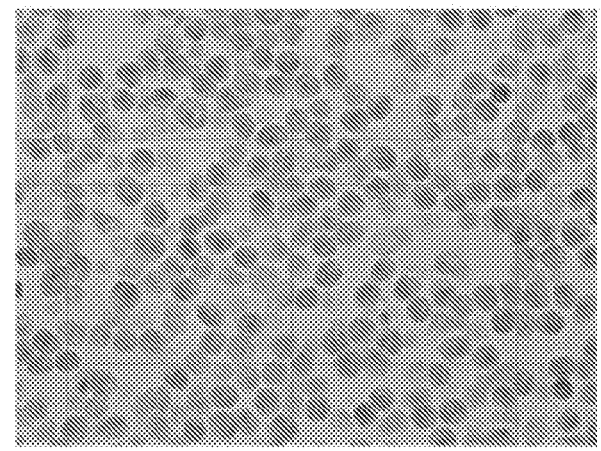
Figure 10:
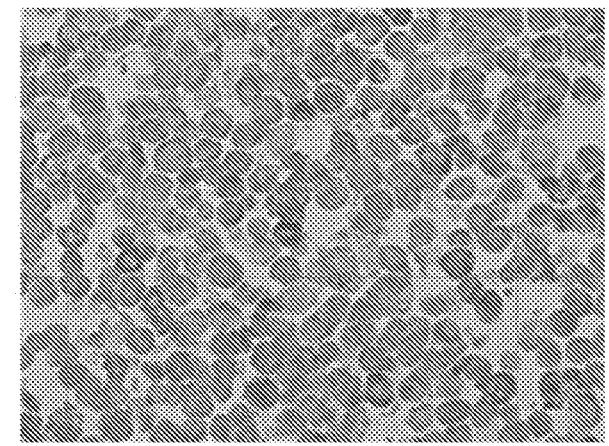

FIG. 10. Immunohistochemical staining of a panel of T cells (CAR modified and unmodified control) in formaldehyde fixed and paraffin embedded sections. (A) H&E staining of CAR$^+$ T cells. (B) Absence of specific staining was observed in sections of CAR$^{neg}$ control T cells stained with clone no. 136.20.1 mAb, HRP-conjugated detection antibody, and counter stained with hematoxylene. (C) CD19-specific CAR$^+$ T cells expressing CD19RCD28 stained with clone no. 136.20.1 mAb and peroxidase-labeled secondary antibodies. Deposition of DAB on T cells indicating localization of CAR protein on the cell surface (arrow).

Figure 11:
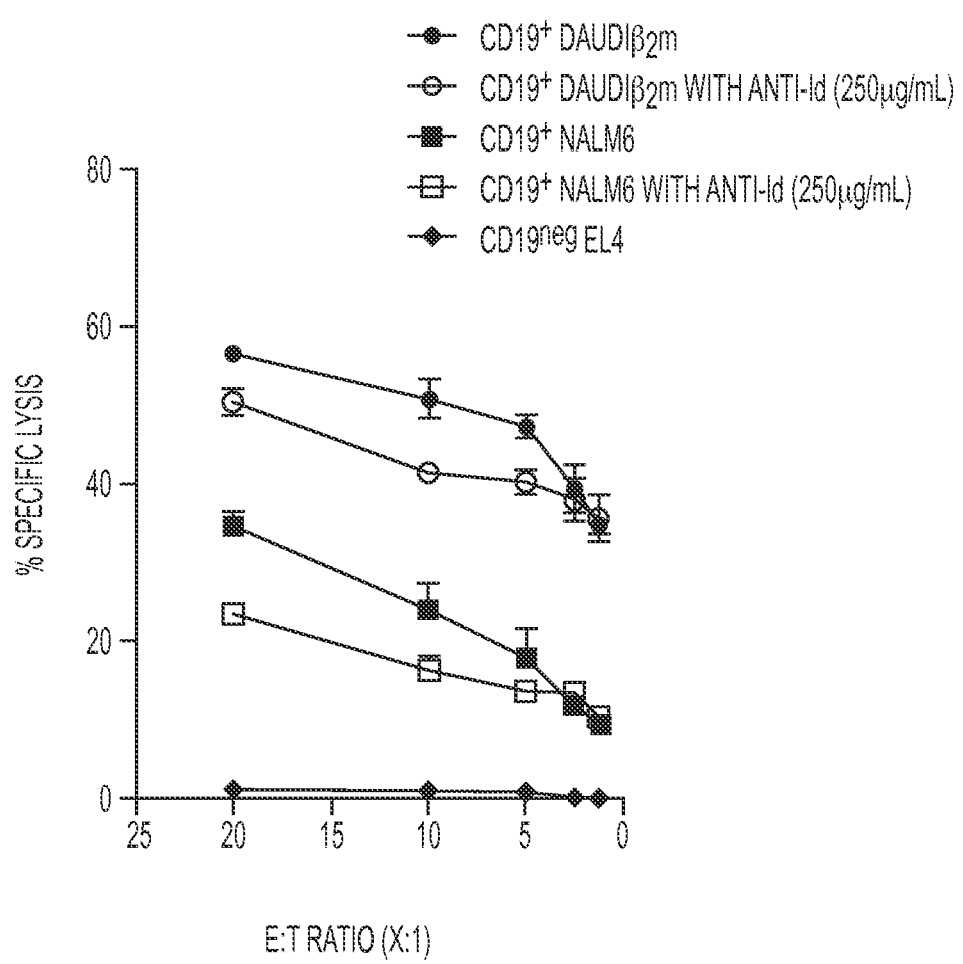

FIG. 11. Inhibition of specific lysis mediated by CD19-specific CAR$^+$ T effector cells in a CRA. CD19-specific CAR$^+$ T cells were incubated with clone no. 136.20.1 mAb at 250 µg/mL and then washed to remove unbound antibody. The effector cells were then co-cultured with $^{51}$Cr-labeled CD19$^+$ tumor targets (NALM-6 and Daudiβ$_2$m). Percentage specific lysis were calculated for effector cells bound by clone no. 136.20.1 and effector cell only at different Effector:Target (E:T) ratios.

Figure 12B:
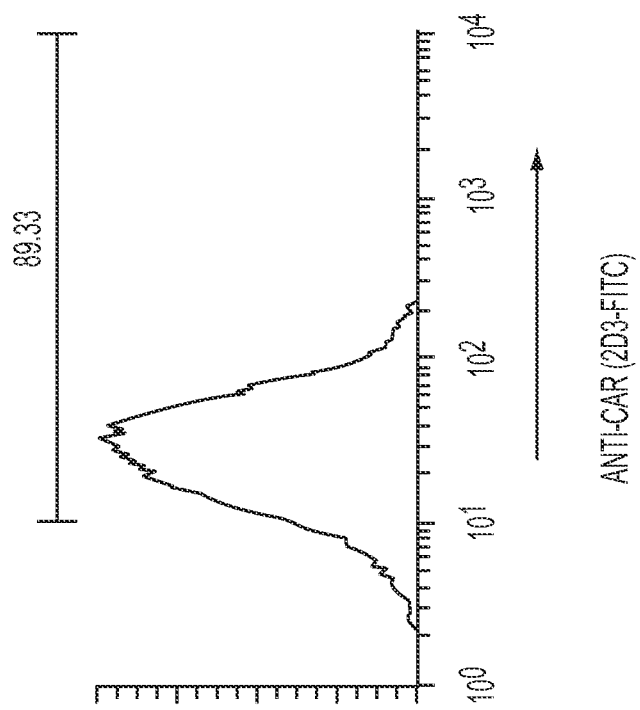
Figure 12A:
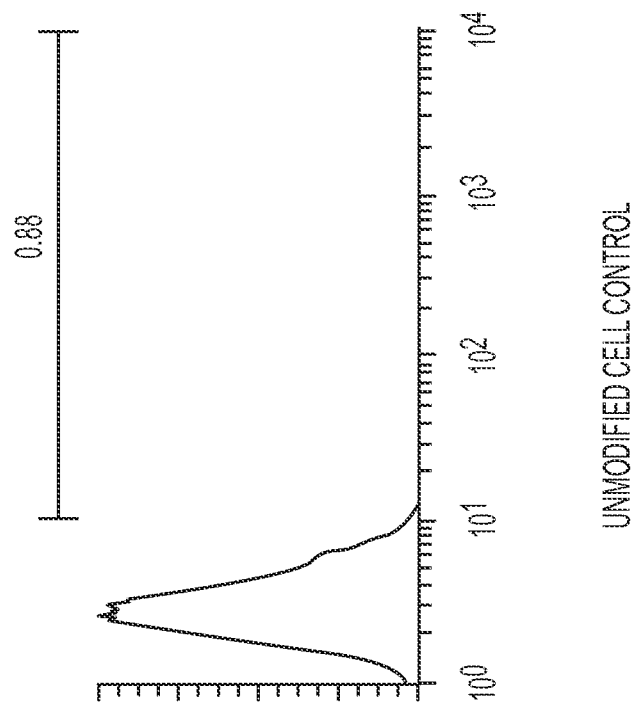

FIG. 12. FACS plots showing detection CAR modified T cells by all CAR mAb (2D3-FITC). T cells were genetically modified to express a CD19-specific CAR that contains an IgG$_4$ Fc domain and expanded ex vivo on clone 4.0 (K562-artificial antigen presenting cells). Shown in picture are detection of CAR-modified T cells by 2D3 along with ex vivo expanded unmodified control T cells.

Figure 13A:
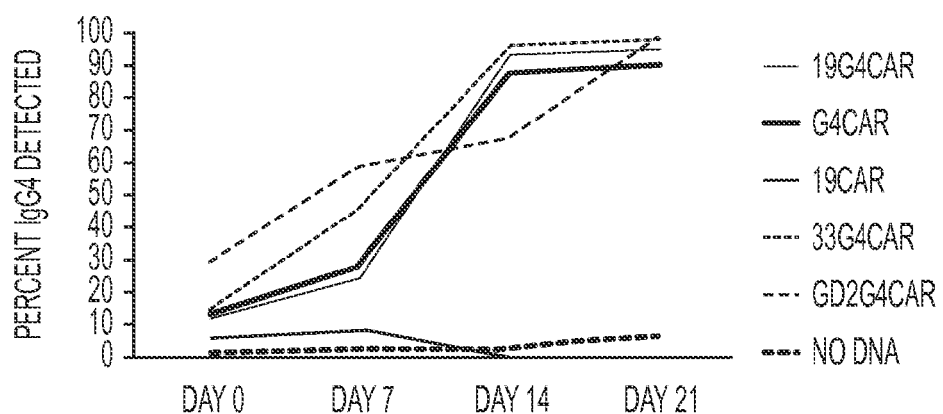
Figure 13B:
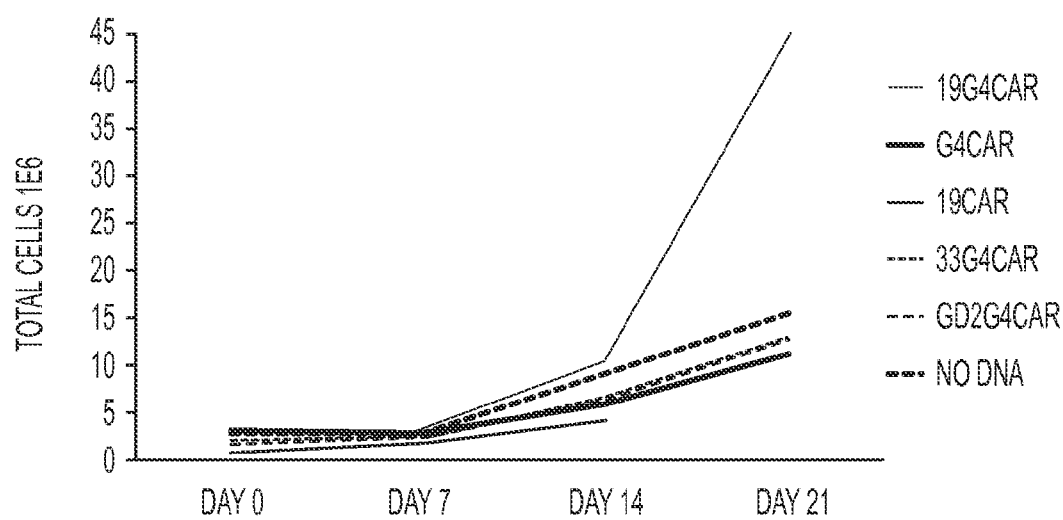

FIG. 13. Proof-of-principle showing all-CAR mAb (2D3) can impart proliferative signal upon CAR modified T cells through CD3-zeta via ITAM motif. A panel of CAR$^+$ T cells targeting variety of tumor associated antigens viz., CD19, CD33, GD2 were made on a CAR backbone that contains an IgG$_4$ immunoglobulin constant region. scFv derived from 2D3 were expressed on artificial antigen presenting cells (K562), which were then irradiated and used in co-culture with PBMC-derived T cells. (A) Shown in the image are ex vivo expansion of genetically-modified T cells over a period of 21 days. All CAR$^+$ T cells, irrespective of antigen specificity, selectively proliferated in culture over time. Unmodified control T cells lacking IgG$_4$ Fc domain received no proliferative signal and died out in the same time. (B) Shown in image are total T cell counts, of CAR modified T cells over 21 day co-culture period as described.

FIG. 14. Study design to compare ability of chimeric antigen receptor (CAR) ligand (CARL) versus CD19 TAA on K562 cells for the selective propagation of CAR$^+$ T cells (CART). A) Artificial antigen presenting cells (aAPC) demonstrated in I) were derived from parental K562 cells following transgene transfer, stable integration, and clonal selection. Each aAPC clone expresses either CARL, a scFv derived from 2D3 mAb that binds IgG4 exodomain of CAR, or truncated human CD19. II) CART used to evaluate specificity towards CARL or CD19 are shown. SB-derived DNA plasmids coding for a panel of CARs were individually electro-transferred into PBMC and recursively stimulated with CD19+ K562 or CARL+ K562 in the presence of soluble recombinant human IL-2. Each CAR follows a modular design. 19G4CAR contains the IgG4 scaffold and targets CD19 through the same scFv as 19CAR which lacks IgG4 scaffold and instead uses CD8α hinge and extracellular domain. GD2G4CAR contains the IgG4 scaffold and targets GD2. G4CAR contains the IgG4 scaffold, but has no scFv. All CARs employ of a 2nd generation design containing CD28 and CD3ζ signaling endodomains. B) On Day 0, synchronous electroporation of PBMC was undertaken with DNA plasmid coding for SB transposase (SB11) and SB DNA plasmids coding for CAR species. To achieve outgrowth of T cells stably expressing CARs, the genetically modified cells were co-cultured, beginning on Day 1, upon γ-irradiated CD19+ or CARL+K562 in the presence of 50 IU/mL IL-2. Cytokine was added with stimulation or during media change. Restimulation of CAR with aAPC occurred every 7 days until Day 21. C) Diagram of docking between CARL+K562 cells and 19G4CAR+ T cells as compared with CD19+ K562 cells with 19G4CAR+ T cells.

FIG. 15. Characterization of aAPC and CAR+ T cells. A) CD19 and CARL as SB transposons were integrated into parental K562 cells using SB11 transposase and clonally expanded for homogeneous expression of CD19 or CARL. Dot plots depict the expression of CD19 and CARL on parental K562 and derived clones. The stable expression of CARL is shown using antibody that detects mouse Fab. B) The expression level of CAR species as determined by flow cytometry is shown on Days 1 and 21 of co-culture with aAPC. Expression of chimeric IgG4 revealed CAR expression in all constructs except 19CAR which was determined using an antibody against human Fc. The percentage of cells in each flow plot quadrant is provided as an inset. C) The effect of aAPC design on abundance of CAR expression was assessed on Day 21 by measuring mean fluorescent intensity (MFI) of IgG4 signal by flow cytometry. The experiments are designated [CAR & aAPC] with unmodified mock electroporated T cells (No DNA plasmid) used as a control. Each experimental group contained 4 or 5 separate donor derived PBMC. Statistical comparison was undertaken by One-way ANOVA followed by unpaired t-tests between each experiment ($*=p<0.05$).

FIG. 16. Comparison of CAR+ T cells propagated on CD19+ or CARL+ aAPC. A) Total inferred T-cell number and B) CAR (IgG4) expression for each CART was measured every 7 days for 5 donors. Top panel: 19CAR+ or G4CAR+ T cells were numerically expanded on either CD19+ or CARL+ aAPC. Bottom panel: 19G4CAR+ T cells were propagated on either CD19+ or CARL+ aAPC. C) After 21 days of co-culture on CD19+ or CARL+ aAPC, 19G4CAR+ T cells from 5 donors were assessed for expression of markers associated with memory (top panel) or T cell co-receptors (bottom panel). D) Specific killing by electroporated/propagated T cells expressing 19CAR, G4CAR, and 19G4CAR, by CRA at a ratio of 5 effectors to 1 target cell. The tumor targets were EL-4 (murine thymoma—GD2+, CD19neg), NALM-6 (human B cell ALL—GD2neg, CD19+), and K562 (a human CML—GD2neg, CD19neg). Up to 5 donors were tested in 4 independent experiments. ns—No significance, $*=p<0.05$, $***=p<0.001$.

Figure 17A:
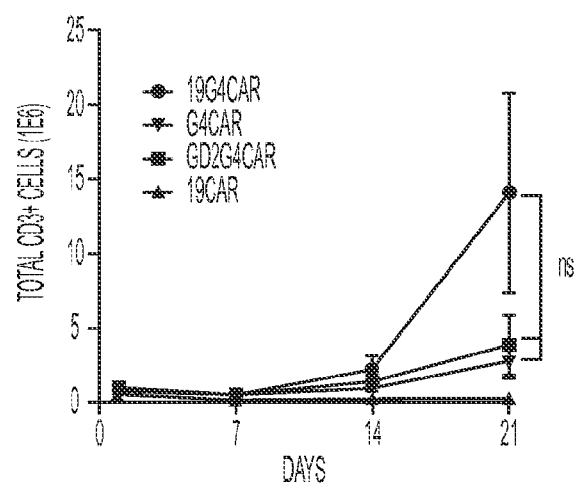
Figure 17B:
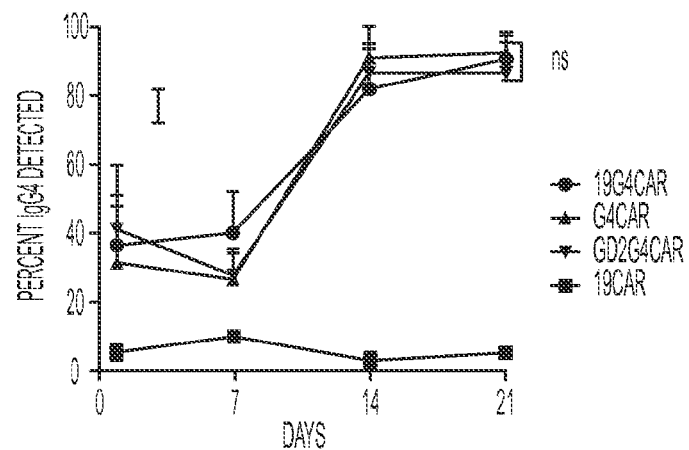

FIG. 17. Numeric expansion of CAR+ T cells using CARL+ aAPC. A) Total inferred T-cell number and B) CAR (IgG4) expression for each CART was measured every 7 days from 4 to 5 donors for 21 days of co-culture on aAPC. The differences between Day 21 total T-cell number and percent CAR expression was assessed using One-way ANOVA. C) The specific killing by panel of T cells expressing GD2G4CAR, 19G4CAR, and G4CAR, were tested using CRA at a ratio of 5 effectors to 1 target cell. The targets were EL-4 (GD2+, CD19$^{neg}$), NALM-6 (GD2$^{neg}$, CD19+), and parental K562 (GD2$^{neg}$, CD19$^{neg}$). Two-way ANOVA followed by unpaired t-tests was performed for 4 to 5 donors tested in 4 independent tests on Day 21 of co-culture on aAPC. ns—No significance, $*=p<0.05$.

Figure 18:
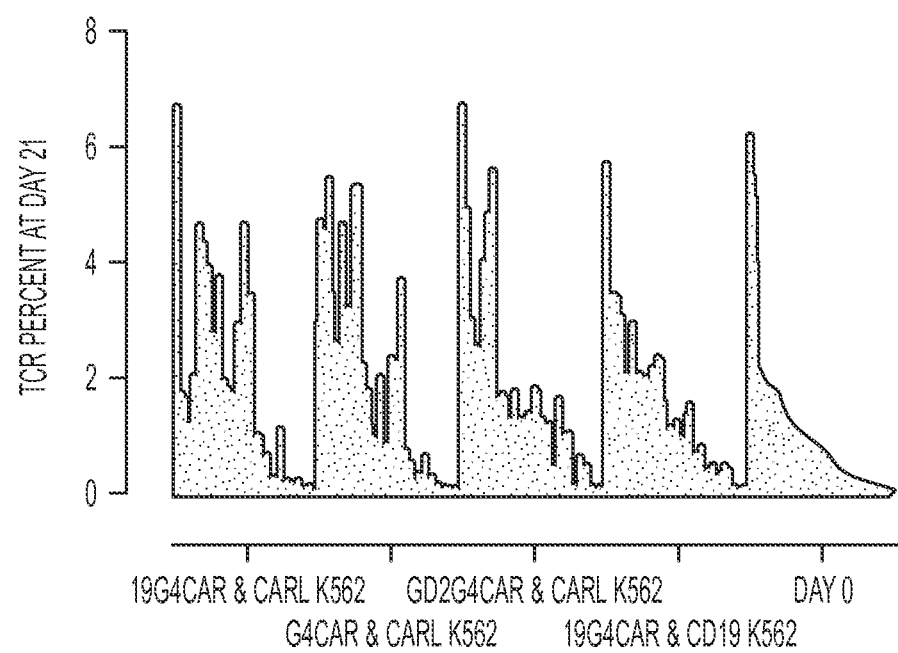
Figure 19A:
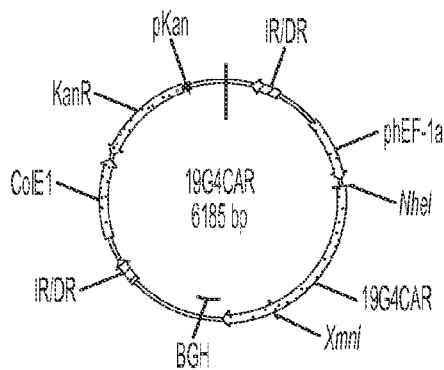
Figure 19B:
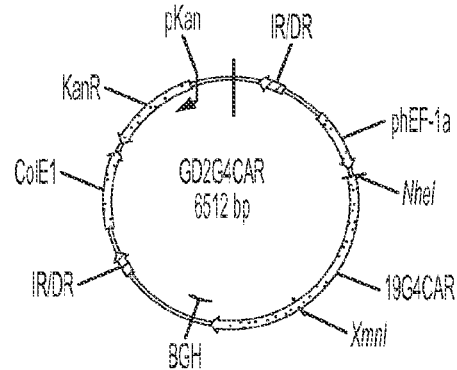
Figure 19C:
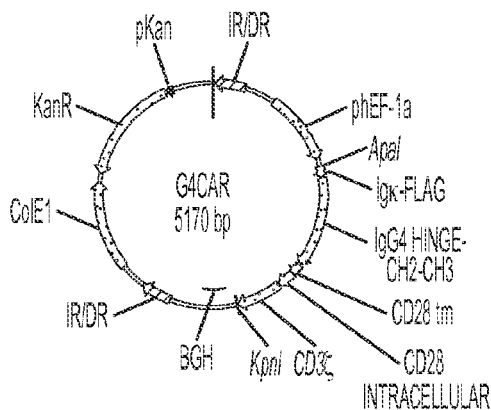
Figure 19D:
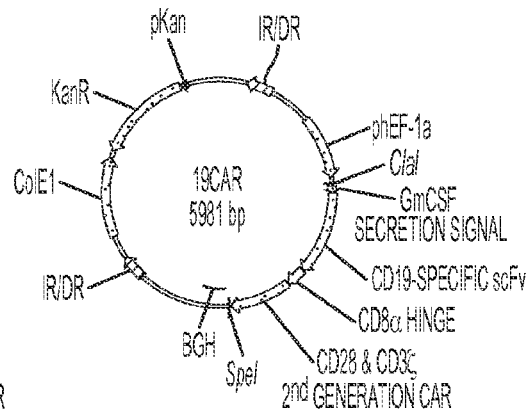
Figure 19E:
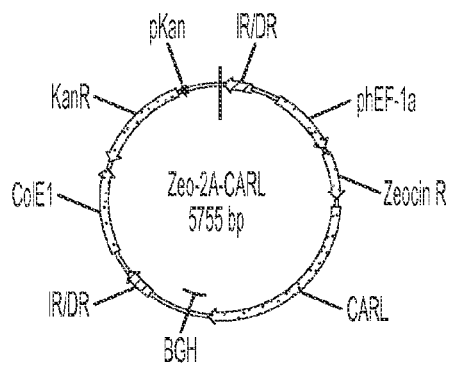
Figure 19F:
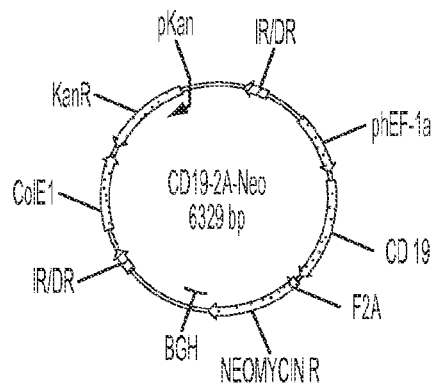

FIG. 18. Comparison of TCR repertoire changes induced by CAR-mediated expansion on aAPC. A) TCR repertoire was measured for 111 TCR α, β, γ, and δ alleles using DTEA. 24 TCR abundance was organized from the most to the least frequently occurring transcripts based on sorted CD3+CD56$^{neg}$ cells from Day 0. The set is visually represented next to TCR repertoire expressed by T cells at Day 21 of co-culture on CARL+ K562 cells and CD19+ K562 cells. Analysis was performed on 2 donors and a representative plot of one donor is shown.

FIG. 19. Vector maps for expression of transgenes. Each DNA plasmid expresses a transgene of interest under promoter human Elongation Factor 1 alpha (phEF-1α), using the beta hemoglobin poly-adenylation signal (BGH) to terminate transcription. The indirect repeats/direct repeats (IR/DR) allow for transgene transposition into the genome using SB11. All plasmids were propagated in bacteria using the origin of replication ColE1 and Kanamycin resistance (KanR) under the promoter pKan. A) 19G4CAR demonstrates the original plasmid design used in these studies and shows NheI and XmnI restriction enzyme (RE) sites used to generate B) GD2G4CAR from PCR-directed truncation of CD19-specific scFv on 19G4CAR which led to the generation of C) G4CAR and final ligation using ApaI and KpnI REs. D) 19CAR was designed without an IgG4 exodomain, instead expressing the CD8α hinge and exodomain. E) Zeo-2ACARL, expressing CARL, and F) CD19-2A-Neo, expressing truncated human CD19 (tCD19), were designed to express CARL or CD19 on aAPC under drug selection conditions.

DESCRIPTION OF ILLUSTRATIVE EMBODIMENTS

Therapeutics that employ CAR-expressing cells for targeting or specific antigens (e.g., tumor-associated antigens) are currently being investigated for the treatment of a variety of disease from cancers to infectious disease. However, the complexity of these agents requires specialized tools for the purification, propagation and control of CAR-expressing cells, which were previously not available. Embodiments of the present invention provide antibodies that specifically bind to CAR T-cells and can be used to selectively purify, propagate or target CAR T-cells. For example, in one aspect, antibodies are provided that specifically bind to a region of the heavy chain constant domain shared by a wide array of CAR T-cells. For example, the 2D3 monoclonal antibody specifically binds to CAR expressing T-cell and can be used to analyze, isolate or propagate these cells. Likewise, specific anti-idiotype (anti-Id) mAbs are provided with specificity for CD19-specific CARs. The mouse mAb (clone no. 136.20.1) recognizes CD19-specific CARs derived from anti-human CD19 mAb (clone FMC63). The specificity of this mAb for CD19-specific CAR id demonstrated using (i) flow cytometry, (ii) western blotting, (iii) transmission electron microscopy (TEM), and (iv) immunocytochemistry. Furthermore, the binding of this anti-Id mAb to the scFv region of CD19RCD28 was demonstrated using a panel of CAR$^+$ T cells and inhibition of CD19-dependent cytolysis as observed by chromium release assay (CRA) and video time lapse microscopy (VTLM).

Previously, CARs expressed on the T-cell surface were detected by antibodies directed against epitope tags or spacer domains incorporated in the extracellular domain. However, such tags would preferably not be employed in therapeutic CAR T-cells. Other commercially-available antibodies detecting Fc regions can, in some case, detect CARs, but cross-reactivity against immunoglobulin, especially when genetically modified T cells are to be assayed from patient-derived PBMC remains an obstacle. Likewise, alternative CAR designs that are non-immunogenic and avoid using a $CH_2$—$CH_3$ or employ scaffolding domains that are smaller than the Fc region, may improve the therapeutic potential of genetically modified T cells, but render Fc-binding antibodies useless as reagents. Thus, reagents that can directly bind to and detect the scFv region of the CAR, such as the mAbs provided here, represent the most effective reagents for manipulation of CAR T-cell populations. Indeed, the anti-idiotype mAb developed for detection of CD19-specific CAR$^+$ T cells provides a methodology to generate reagents to detect CARs targeting TAAs alternative to CD19.

Thus, the mAbs that binds to the scFv derived CAR T cells provided herein can serve as new and effective systems for T-cell manipulation. Antibodies specific for CAR T-cells (or in some cases CD-19 targeted CAR T-cells particularly) can be used to analyze and characterize CAR reagents. Perhaps even more importantly the CAR-binding agents provided herein can be used to specifically select, purify or propagate CAR T-cells. For example, antibodies of the embodiments can be used as part of a system for selectively growing CAR cells, such as by expressing the antibodies (or portions thereof) in aAPCs. In the case of antibodies that bind CARs in general, the antibodies can be used to generate lines of aAPCs as standardized reagents for expansion of CAR T-cell populations, a significant advantage over the systems previously available that must the individualized for particular CAR therapeutics. Likewise, the antibodies can be used to isolate and target CAR cells in vivo to monitor therapy and, if needed, target and inhibit CAR-expressing cells in a subject. These reagents will likely be instrumental in developing and implementing gene therapy trials infusing CD-19 CAR$^+$ T cells as well as CAR$^+$ T cells in general (i.e., CARs containing a generic human Fc gamma chain derived scaffold in its polypeptide chain).

I. CHIMERIC ANTIGEN RECEPTORS

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3ζ a transmembrane domain and endodomain. The specificity of other CAR designs may be derived from ligands of receptors (e.g., peptides) or from Dectins. In particular embodiments, one can target malignant B cells by redirecting the specificity of T cells by using a CAR specific for the B-lineage molecule, CD19. In certain cases, CARs comprise domains for additional co-stimulatory signaling, such as CD3ζ, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, cytokines, and cytokine receptors.

As used herein, the term "antigen" is a molecule capable of being bound by an antibody or T-cell receptor. An antigen is additionally capable of inducing a humoral immune response and/or cellular immune response leading to the production of B and/or T lymphocytes.

The present invention involves antibodies that have specificity towards antigen-specific and universal chimeric antigen receptor (CAR) polypeptides, including a CAR that has been humanized to reduce immunogenicity (hCAR). In certain embodiments, the CAR may recognize an epitope comprised of the overlapping sequence between one or more antigens.

In certain aspects, the invention includes a method of making and/or expanding the antigen-specific redirected TCR$^{neg}$ cells that comprises transfecting TCR$^{neg}$ cells with an expression vector containing a DNA construct encoding the hCAR, then stimulating the cells with an antibody to the receptor to cause the cells to proliferate.

II. ANTIBODIES OF THE EMBODIMENTS

In certain embodiments, an antibody or a fragment thereof that binds to at least a portion of CD19scFv-specific CAR protein and interferes with the killing of CD19$^+$ target cells and its associated use in treatment of diseases is contemplated. In other embodiments, an antibody or a fragment thereof that binds to at least the $CH_2$—$CH_3$ hinge of CAR protein (all-CAR) is provided. As used herein, the term "antibody" is intended to refer broadly to any immunologic binding agent, such as IgG, IgM, IgA, IgD, and IgE as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-CD19-specific CAR or all-CAR antibody is a monoclonal antibody or a humanized antibody. By known means and as described herein, polyclonal or monoclonal antibodies, antibody fragments, and binding domains and CDRs (including engineered forms of any of the foregoing) may be created that are specific to CD19-specific CAR or all-CAR protein, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen in order to produce antibodies specific for CD19scFv-specific CAR or all-CAR protein. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a CD19scFv-specific CAR or all-CAR antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

III. CHIMERIC ANTIGEN RECEPTORS

Embodiments of the present invention involve nucleic acids, including nucleic acids encoding an antigen-specific chimeric antigen receptor (CAR) polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprised of the shared space between one or more antigens. Pattern recognition receptors, such as Dectin-1, may be used to derive specificity to a carbohydrate antigen. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor. A complementarity determining region (CDR) is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor contains three CDRs (CDR1, CDR2, and CDR3). Since the antigen receptors are typically composed of two polypeptide chains, there are six CDRs for each antigen receptor that can come into contact with the antigen—each heavy and light chain contains three CDRs. Because most sequence variation associated with immunoglobulins and T-cell receptors are found in the CDRs, these regions are sometimes referred to as hypervariable domains. Among these, CDR3 shows the greatest variability as it is encoded by a recombination of the VJ (VDJ in the case of heavy chain and TCR αβ chain) regions.

It is contemplated that the human CAR nucleic acids are human genes to enhance cellular immunotherapy for human patients. In a specific embodiment, the invention includes a full length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into what has been referred to by Winters as a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8α.

The intracellular signaling domain of the chimeric receptor of the invention is responsible for activation of at least one of the normal effector functions of the immune cell in which the chimeric receptor has been placed. The term "effector function" refers to a specialized function of a differentiated cell. Effector function of a T cell, for example, may be cytolytic activity or helper activity including the secretion of cytokines. Effector function in a naive, memory, or memory-type T cell includes antigen-dependent proliferation. Thus the term "intracellular signaling domain" refers to the portion of a protein that transduces the effector function signal and directs the cell to perform a specialized function. While usually the entire intracellular signaling domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular signaling domain is thus meant to include any truncated portion of the intracellular signaling domain sufficient to transduce the effector function signal. Examples include the zeta chain of the T-cell receptor or any of its homologs (e.g., eta, delta, gamma, or epsilon), MB1 chain, B29, Fc RIII, Fc RI, and combinations of signaling molecules, such as CD3ζ and CD28, CD27, 4-1BB, DAP-10, OX40, and combinations thereof, as well as other similar molecules and fragments. Intracellular signaling portions of other members of the families of activating proteins can be used, such as FcγRIII and FcεRI. See Gross et al. (1992), Stancovski et al. (1993), Moritz et al. (1994), Hwu et al. (1995), Weijtens et al. (1996), and Hekele et al. (1996) for disclosures of cTCR's using these alternative transmembrane and intracellular domains. In a preferred embodiment, the human CD3ζ intracellular domain was taken for activation.

The antigen-specific extracellular domain and the intracellular signaling-domain may be linked by a transmembrane domain, such as the human $IgG_4Fc$ hinge and Fc regions. Alternatives include the human CD4 transmembrane domain, the human CD28 transmembrane domain, the transmembrane human CD3ζ domain, or a cysteine mutated human CD3ζ domain, or other transmembrane domains from other human transmembrane signaling proteins, such as CD16 and CD8 and erythropoietin receptor.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, and 4-1BB (CD137). In addition to a primary signal initiated by CD3 ζ, an additional signal provided by a human costimulatory receptor inserted in a human CAR is important for full activation of T cells and could help improve in vivo persistence and the therapeutic success of the adoptive immunotherapy.

In particular embodiments, the invention concerns isolated nucleic acid segments and expression cassettes incorporating DNA sequences that encode the CAR. Vectors of the present invention are designed, primarily, to deliver desired genes to immune cells, preferably T cells under the control of regulated eukaryotic promoters, for example, MNDU3 promoter, CMV promoter, EF1alpha promoter, or Ubiquitin promoter. Also, the vectors may contain a selectable marker, if for no other reason, to facilitate their manipulation in vitro. In other embodiments, the CAR can be expressed from mRNA in vitro transcribed from a DNA template.

Chimeric antigen receptor molecules are recombinant and are distinguished by their ability to both bind antigen and transduce activation signals via immunoreceptor activation motifs (ITAM's) present in their cytoplasmic tails. Receptor constructs utilizing an antigen-binding moiety (for example, generated from single chain antibodies (scFv)) afford the additional advantage of being "universal" in that they bind native antigen on the target cell surface in an HLA-independent fashion. For example, several laboratories have reported on scFv constructs fused to sequences coding for the intracellular portion of the CD3 complex's zeta chain ($\zeta$), the Fc receptor gamma chain, and sky tyrosine kinase (Eshhar et al., 1993; Fitzer-Attas et al., 1998). Re-directed T cell effector mechanisms including tumor recognition and lysis by CTL have been documented in several murine and human antigen-scFv: $\zeta$ systems (Eshhar, 1997; Altenschmidt et al., 1997; Brocker et al., 1998).

To date non-human antigen binding regions are typically used in constructing a chimeric antigen receptor. A potential problem with using non-human antigen binding regions, such as murine monoclonal antibodies, is the lack of human effector functionality and inability to penetrate into tumor masses. In other words, such antibodies may be unable to mediate complement-dependent lysis or lyse human target cells through antibody-dependent cellular toxicity or Fc-receptor mediated phagocytosis to destroy cells expressing CAR. Furthermore, non-human monoclonal antibodies can be recognized by the human host as a foreign protein, and therefore, repeated injections of such foreign antibodies can lead to the induction of immune responses leading to harmful hypersensitivity reactions. For murine-based monoclonal antibodies, this is often referred to as a Human Anti-Mouse Antibody (HAMA) response. Therefore, the use of human antibodies is more preferred because they do not elicit as strong a HAMA response as murine antibodies. Similarly, the use of human sequences in the CAR can avoid immune-mediated recognition and therefore elimination by endogenous T cells that reside in the recipient and recognize processed antigen in the context of HLA.

In some embodiments, the chimeric antigen receptor comprises: a) an intracellular signaling domain, b) a transmembrane domain, and c) an extracellular domain comprising an antigen binding region.

In specific embodiments, intracellular receptor signaling domains in the CAR include those of the T cell antigen receptor complex, such as the zeta chain of CD3, also Fc$\gamma$ RIII costimulatory signaling domains, CD28, CD27, DAP10, CD137, OX40, CD2, alone or in a series with CD3zeta, for example. In specific embodiments, the intracellular domain (which may be referred to as the cytoplasmic domain) comprises part or all of one or more of TCR zeta chain, CD28, CD27, OX40/CD134, 4-1BB/CD137, Fc$\epsilon$RI$\gamma$, ICOS/CD278, IL-2Rbeta/CD122, IL-2Ralpha/CD132, DAP10, DAP12, and CD40. In some embodiments, one employs any part of the endogenous T cell receptor complex in the intracellular domain. One or multiple cytoplasmic domains may be employed, as so-called third generation CARs have at least two or three signaling domains fused together for additive or synergistic effect, for example.

In certain embodiments of the chimeric antigen receptor, the antigen-specific portion of the receptor (which may be referred to as an extracellular domain comprising an antigen binding region) comprises a tumor associated antigen or a pathogen-specific antigen binding domain including carbohydrate antigen recognized by pattern-recognition receptors, such as Dectin-1. A tumor associated antigen may be of any kind so long as it is expressed on the cell surface of tumor cells. Exemplary embodiments of tumor associated antigens include CD19, CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, and so forth. In certain embodiments, the CAR can be co-expressed with a membrane-bound cytokine to improve persistence when there is a low amount of tumor-associated antigen. For example, CAR can be co-expressed with membrane-bound IL-15.

In certain embodiments intracellular tumor associated antigens may be targeted, such as HA-1, survivin, WT1, and p53. This can be achieved by a CAR expressed on a universal T cell that recognizes the processed peptide described from the intracellular tumor associated antigen in the context of HLA. In addition, the universal T cell may be genetically modified to express a T-cell receptor pairing that recognizes the intracellular processed tumor associated antigen in the context of HLA.

The pathogen may be of any kind, but in specific embodiments the pathogen is a fungus, bacteria, or virus, for example. Exemplary viral pathogens include those of the families of Adenoviridae, Epstein-Barr virus (EBV), Cytomegalovirus (CMV), Respiratory Syncytial Virus (RSV), JC virus, BK virus, HSV, HHV family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and *Stachybotrys*. Exemplary pathogenic bacteria include *Streptococcus, Pseudomonas, Shigella, Campylobacter, Staphylococcus, Helicobacter, E. coli, Rickettsia, Bacillus, Bordetella, Chlamydia, Spirochetes*, and *Salmonella*. In one embodiment the pathogen receptor Dectin-1 can be used to generate a CAR that recognizes the carbohydrate structure on the cell wall of fungi. T cells genetically modified to express the CAR based on the specificity of Dectin-1 can recognize *Aspergillus* and target hyphal growth. In another embodiment, CARs can be made based on an antibody recognizing viral determinants (e.g., the glycoproteins from CMV and Ebola) to interrupt viral infections and pathology.

In some embodiments, the pathogenic antigen is an *Aspergillus* carbohydrate antigen for which the extracellular domain in the CAR recognizes patterns of carbohydrates of the fungal cell wall, such as via Dectin-1.

It is contemplated that the chimeric construct can be introduced into the subject's own T cells as naked DNA or in a suitable vector. Methods of stably transfecting T cells by electroporation using naked DNA are known in the art. See, e.g., U.S. Pat. No. 6,410,319. Naked DNA generally refers to the DNA encoding a chimeric receptor of the present invention contained in a plasmid expression vector in proper orientation for expression. Advantageously, the use of naked DNA reduces the time required to produce T cells expressing the chimeric receptor of the present invention.

Alternatively, a viral vector (e.g., a retroviral vector, adenoviral vector, adeno-associated viral vector, or lentiviral vector) can be used to introduce the chimeric construct into T cells. Suitable vectors for use in accordance with the method of the present invention are non-replicating in the subject's T cells. A large number of vectors are known that are based on viruses, where the copy number of the virus maintained in the cell is low enough to maintain the viability of the cell. Illustrative vectors include the pFB-neo vectors (STRATAGENE®) disclosed herein as well as vectors based on HIV, SV40, EBV, HSV, or BPV.

Once it is established that the transfected or transduced T cell is capable of expressing the chimeric receptor as a surface membrane protein with the desired regulation and at a desired level, it can be determined whether the chimeric receptor is functional in the host cell to provide for the desired signal induction. Subsequently, the transduced T cells are reintroduced or administered to the subject to activate anti-tumor responses in the subject. To facilitate administration, the transduced T cells according to the invention can be made into a pharmaceutical composition or made into an implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed that does not ineffectuate the cells expressing the chimeric receptor. Thus, desirably the transduced T cells can be made into a pharmaceutical composition containing a balanced salt solution, preferably Hanks' balanced salt solution, or normal saline.

IV. ARTIFICIAL ANTIGEN PRESENTING CELLS

In some cases, aAPCs are useful in preparing CAR-based therapeutic compositions and cell therapy products. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009). As further detailed herein, in some aspects, aAPCs are provided, which comprise an antibody of the embodiments expressed on the surface. For instance, in some aspects, the antibody can be provided in additional to or instead of the antigen that is recognized by the CAR in order to mediate CAR T-cell expansion.

Thus, aAPCs, the cells can express an antibody and/or an antigen of interest. In addition to antibody or antigen of interest, the aAPC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2 (see Kim et al., 2004, Nature, Vol. 22(4), pp. 403-410). Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

Cells selected to become aAPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become aAPCs also lack the ability to express at least one endogenous counterpart (e.g., endogenous MEW Class I or Class II molecule and/or endogenous assisting molecules as described above) to the exogenous MEW Class I or Class II molecule and assisting molecule components that are introduced into the cells. Furthermore, aAPCs preferably retain the deficiencies and poikilothermic properties that were possessed by the cells prior to their modification to generate the aAPCs. Exemplary aAPCs either constitute or are derived from a transporter associated with antigen processing (TAP)-deficient cell line, such as an insect cell line. An exemplary poikilothermic insect cells line is a *Drosophila* cell line, such as a Schneider 2 cell line (see, e.g. Schneider, J. Embryol. Exp. Morph. 1972 Vol 27, pp. 353-365). Illustrative methods for the preparation, growth, and culture of Schneider 2 cells, are provided in U.S. Pat. Nos. 6,225,042, 6,355,479, and 6,362,001.

In one embodiment, aAPCs are also subjected to a freeze-thaw cycle. In an exemplary freeze-thaw cycle, the aAPCs may be frozen by contacting a suitable receptacle containing the aAPCs with an appropriate amount of liquid nitrogen, solid carbon dioxide (i.e., dry ice), or similar low-temperature material, such that freezing occurs rapidly. The frozen aAPCs are then thawed, either by removal of the aAPCs from the low-temperature material and exposure to ambient room temperature conditions, or by a facilitated thawing process in which a lukewarm water bath or warm hand is employed to facilitate a shorter thawing time. Additionally, aAPCs may be frozen and stored for an extended period of time prior to thawing. Frozen aAPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing aAPCs that undergo the freeze-thaw cycle, or are essentially removed, such as by transfer of aAPCs to media that is essentially devoid of such preservatives.

In other preferred embodiments, xenogenic nucleic acid and nucleic acid endogenous to the aAPCs, may be inactivated by crosslinking, so that essentially no cell growth, replication or expression of nucleic acid occurs after the inactivation. In one embodiment, aAPCs are inactivated at a point subsequent to the expression of exogenous MHC and assisting molecules, presentation of such molecules on the surface of the aAPCs, and loading of presented MHC molecules with selected peptide or peptides. Accordingly, such inactivated and selected peptide loaded aAPCs, while rendered essentially incapable of proliferating or replicating, retain selected peptide presentation function. Preferably, the crosslinking also yields aAPCS that are essentially free of contaminating microorganisms, such as bacteria and viruses, without substantially decreasing the antigen-presenting cell function of the aAPCs. Thus crosslinking maintains the important APC functions of aAPCs while helping to alleviate concerns about safety of a cell therapy product developed using the aAPCs. For methods related to crosslinking and aAPCs, see for example, U.S. Patent Application Publication No. 20090017000, which is incorporated herein by reference.

V. KITS OF THE INVENTION

Any of the compositions described herein may be comprised in a kit. In some embodiments, CAR-binding antibodies are provided in the kit, which also may include reagents suitable for expanding the cells, such as media, aAPCs, growth factors, antigens, other antibodies (e.g., for sorting or characterizing CAR T-cells) and/or plasmids encoding CARs or transposase.

In a non-limiting example, a CAR-binding antibody, a chimeric receptor expression construct (or reagents to generate a chimeric receptor expression construct), reagents for transfection of the expression construct, and/or one or more instruments to obtain allogeneic cells for transfection of the expression construct (such an instrument may be a syringe, pipette, forceps, and/or any such medically approved apparatus) are provided in a kit. In some aspects, the kit comprises reagents or apparatuses for electroporation of cells.

The kits may comprise one or more suitably aliquoted compositions of the present invention or reagents to generate compositions of the invention. The components of the kits may be packaged either in aqueous media or in lyophilized form. The container means of the kits may include at least one vial, test tube, flask, bottle, syringe, or other container means, into which a component may be placed, and preferably, suitably aliquoted. Where there is more than one component in the kit, the kit also will generally contain a second, third, or other additional container into which the additional components may be separately placed. However, various combinations of components may be comprised in a vial. The kits of the present invention also will typically include a means for containing the chimeric receptor construct and any other reagent containers in close confinement for commercial sale. Such containers may include injection or blow molded plastic containers into which the desired vials are retained, for example.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—CD19 CAR-Targeting Monoclonal Antibody—Methods

Ethics Statement.

All experimental procedures pertaining to the use of animals were performed according to the U.T. MD Anderson Cancer Center Institutional Animal Care and Use Committee (IACUC) guidelines and were carried out by the MD Anderson Hybridoma core lab (IACUC approval no. 11-071-2533). All efforts were made to reduce suffering to the animals caused by any experimental procedure. Isoflurane (2-5%) were used as anesthesia whenever required. Details of animal care, anesthesia use and sample collection are provided in separate paragraph. For the peripheral blood mononuclear cells (PBMC) used in the study, blood samples were obtained from healthy volunteers under the protocol title "Acquisition of peripheral blood from healthy volunteers" that aimed to investigate the immunobiology of lymphocytes such as T cells in general and genetically modified T cells in particular (approval obtained from U.T. MD Anderson Cancer Center Institutional Review Board protocol no. LAB07-0296). Healthy volunteers donated blood only after written consent was obtained and the study objectives were explained.

Cells.

Cell lines were obtained from American Type Culture Collection (ATCC) unless otherwise stated. L cells, (a mouse adherent fibroblast cell line derived from C3H/An strain; ATCC no. CRL-2648), Jurkat cells (ATCC no. CRL-1990), NS0 cells (Sigma Aldrich no. 85110503), NALM-6 pre-B ALL cell (DSMZ no. ACC 128), EL4 murine lymphoma T cell line (ATCC no. TIB-39), CD19$^+$ EL4 (genetically modified to express truncated human CD19) (Torikai et al., 2012), and Daudi cells co-expressing EGFP and $\beta_2$-microglobulin (Daudi $\beta_2$m; Rabinovich et al. 2008), were all cultured in complete media (CM) defined as RPMI 1640 (Hyclone) supplemented with heat inactivated 10% fetal bovine serum (FBS) (Hyclone) and 2 mM L-Glutamine (Gibco-Invitrogen). Genetically modified cells were selected in various cytocidal concentrations of neomycin sulfate G418 (Invivogen) at 0.8 mg/mL for NS0 cells, 0.9 mg/mL for L cells, and 1 mg/mL for Jurkat cells (Singh et al., 2008). K562 were transduced with lentivirus to co-express CD64, CD86, CD137L and a membrane-bound IL-15 (mIL-15) to generate artificial antigen presenting cells (aAPC clone no. 4) (O'Connor et al., 2012; Singh et al., 2008; Manuri et al., 2009; Singh et al., 2011; Maiti et al., 2013). Primary human T cells from PBMC were genetically modified to express CD19RCD28 CAR using the Sleeping Beauty (SB) transposon/transposase system and propagated ex vivo in a CAR-dependent manner on CD19$^+$ aAPC (K562, clone no. 4) in CM supplemented with soluble recombinant IL-2 (Novartis/Chiron) at 50 IU/mL and IL-21 at 30 ng/mL (Peprotech) (Singh et al., 2011; Huls et al., 2012).

Cell Surface Expression of CD19-Specific scFv.

Figure 1A:
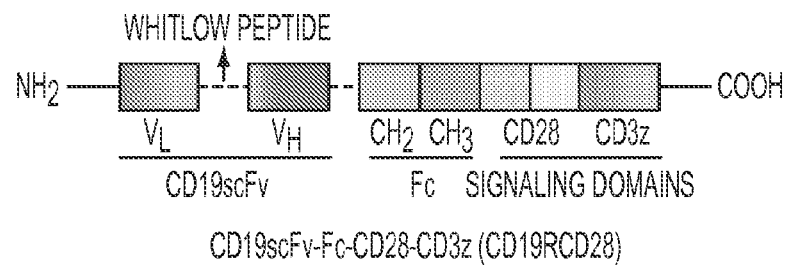
FIG. 1. Schematic of DNA plasmids used for electroporation and expression of transgenes. (A) Constructs showing components of CD19-specific CAR (CD19RCD28). The scFv is derived from mAb clone FMC63 that binds human CD19 and was generated by fusing the $V_L$ and $V_H$ regions via a "Whitlow" linker peptide. The scFv was attached to modified human IgG$_4$ hinge and CH$_2$—CH$_3$ regions that was fused to the CD28 (transmembrane and cytoplasmic) and CD3ζ (cytoplasmic) domains (Kowolik et al., 2006). (B) DNA plasmid designed CD19scFv-mCD8α used to express the transgene on L cells for immunization and screening. The CD19-specific scFv was generated as described, mCD8α EC and TM represents mouse CD8α extracellular and transmembrane domains. (C) Map of destination vector pIRESneo2 (Clontech) where the cDNA for the fusion protein CD19scFv-mCD8α is cloned into NheI and NotI restriction enzyme sites. Expression cassette shows ColE1, colicin E1 (origin of replication); pCMV IE, human cytomegalovirus promoter/enhancer; ECMV IRES, encephalomyocarditis virus internal ribosome entry site which permits translation of two open reading frames from one messenger RNA, and poly A (polyadenylation) signal of the bovine growth hormone. Plasmid confers resistance through ampicillin and after electroporation the cells expressing the transgene of interest are selected on a cytocidal concentration of drug neomycin sulfate (G418).
Figure 1B:
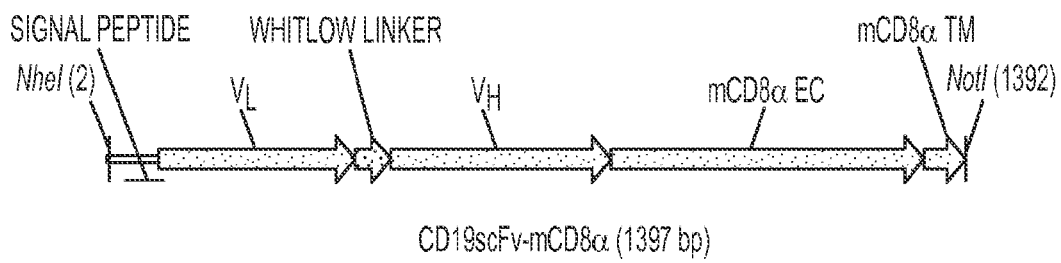
Figure 1C:
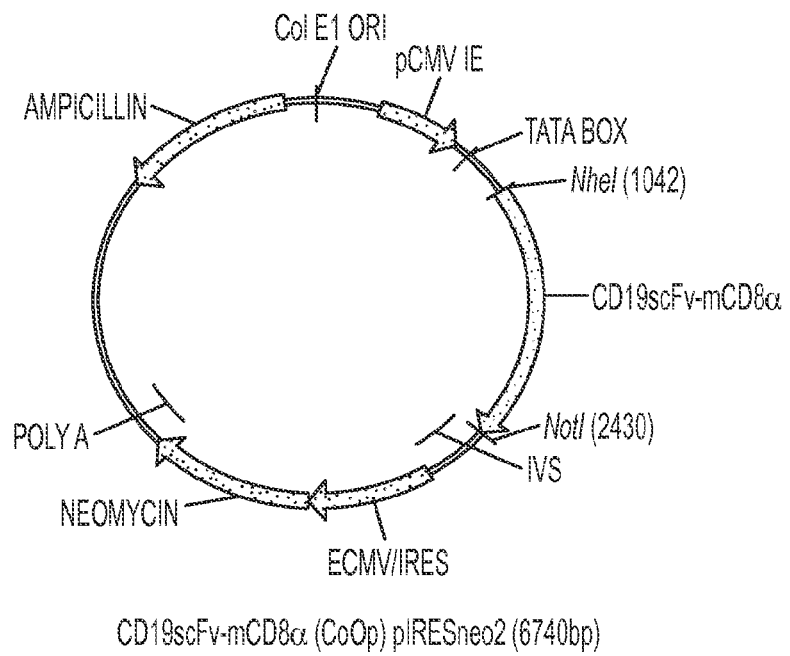

$V_L$ (amino terminus) and $V_H$ (carboxyl terminus) regions were derived from anti-human CD19-specific mAb clone FMC63 (Nicholson et al., 1997). The scFv was formed by joining the $V_L$ and $V_H$ with the 18 amino acid (AA) Whitlow peptide linker (GSTSGSGKPGSGEGSTKG; SEQ ID NO: 26) (Whitlow et al., 1993). This binding domain, denoted as CD19scFv, was then fused in frame with mouse CD8α extra-cellular domain (AA 28-196) and transmembrane domain (AA 197-217) (Swiss-Prot No. P01731 www.expasy.org) to create the fusion protein CD19scFvmCD8α. The cDNA representing the fusion protein was mouse codon optimized and synthesized by a commercial vendor (FIG. 1B, GENEART). The nucleotide sequence of CD19scFvmCD8α was verified and the cDNA was cloned into plasmid pIRESneo2 (Clontech cat no. 6938-1) to generate DNA vector CD19scFvmCD8αpIRESneo2 (FIG. 1C). Purified vector CD19scFvmCD8αpIRESneo2 DNA (endotoxin level<4 EU/mL) at a concentrations of 1 μg per $10^6$ of L cells and 5 μg per $10^6$ Jurkat and NS0 cells, were electro-transferred by a NUCLEOFECTOR® transfection device (model no. AAD-1001, Lonza) employing NUCLEOFECTOR® transfection kit R and program X-005 for L cells and human T cell NUCLEOFECTOR® transfection kit and program U-14 for Jurkat and NS0 cells. Electroporated cells were plated in 6-well culture plates (Corning) containing complete media (CM), incubated for 4 hours, and then added with drug neomycin sulfate (G418) as mentioned. Cells were cultured in an incubator (5% $CO_2$ and 37° C.) and at 24 to 48 hours, the transient expression of CD19scFvmCD8α was assessed by flow cytometry using PE-conjugated anti-mouse CD8α antibody (BD Biosciences). Drug-resistant clones of L cells were propagated to confluence and harvested by trypsinization using 0.05% Trypsin-EDTA (Gibco-Invitrogen). Cells with highest expression level of CD19scFvmCD8α were sorted on a BD FACSARIA® cell sorter (BD Biosciences) using anti-mouse CD8α-PE (BD Biosciences) as detection antibody. Sorted cells were numerically expanded further in the presence of neomycin sulfate (G418). Transgene expression was confirmed by flow cytometry. One L cell (clone no. 12) with the highest stable expression of transgene was chosen and expanded further for immunization purposes. Similarly, Jurkat and NS0 cells expressing CD19scFv were generated to screen hybridoma clones.

Animal Care, Immunization, Lymphocyte Collection.

All the experiments pertaining to the animal use were performed as per the recommendations of the U.T. MD Anderson Cancer Center Institutional Animal Care and Use Committee (IACUC approval no. 11-071-2533). Two BALB/c mice (NCI, Frederick) were immunized in the footpads, each with $5\times10^6$ L cells expressing CD19scFv-mCD8α (clone no. 12) suspended in 50 μL PBS. No adjuvant was used for immunization. The mice were restrained manually (for less than 2 minutes) for cell injection or anesthetized by isoflurane (2-5%) whenever required. Each mouse received a total of 6 injections at 3 day intervals. At the end of $5^{th}$ immunization, mice were anesthetized by isoflurane (2-5%) inhalation and then blood was drawn from the tail vein. Sera were used to evaluate the antibody titer in an indirect ELISA. On Day 18 a mouse with highest titer was chosen for lymphocyte collection and fusion. Mice were euthanized by $CO_2$ inhalation and then popliteal lymph nodes were dissected for collection of lymphocytes.

Generation of Hybridomas.

A schematic outlining the steps involved for development and isolation of a mAb with specificity for the CD19scFv region in CD19RCD28 CAR is shown in FIG. 7. In brief, lymphocytes were washed with RPMI 1640 and then fused with a myeloma partner SP2/0 (ATCC no. CRL1581) at a lymphocyte to myeloma ratio of 1:0.8. Hybridomas were obtained by standard polyethylene glycol (PEG-1450, Sigma-Aldrich) mediated fusion technology. Fused cells were grown in 96-well tissue-culture plates for 10 days in HAT selection media (Sigma-Aldrich) supplemented with 10% hybridoma cloning supplement (HCS) (GE/PAA Lab Inc.). Hybridoma clones were screened on day 10 to evaluate for the presence of antibody.

Screening Hybridoma Clones.

A solid phase ELISA was used to determine the titer for the immune sera and to screen for hybridoma clones producing mAb specific for CD19scFv. Monoclonal antibodies were purified by standard protein G or protein A columns. One hybridoma clone (no. 136.20.1) was selected for characterization.

Flow Cytometry.

For detecting surface expression of CAR, about $0.25\times10^6$ cells were suspended in 0.1 mL of FACS buffer (2% FBS in 1×PBS) and stained with antibodies conjugated to fluorochromes (Table 1). Following blocking for 30 minutes at 4° C. with 2% normal mouse sera (Jackson ImmunoResearch) in FACS buffer and washing twice with FACS buffer, the samples were incubated on ice with primary antibodies or conjugated antibodies for 30 minutes. Data were acquired on a FACSCALIBER™ cell analysis platform (BD Biosciences) using CELLQUEST™ software, version 3.3 (BD Biosciences). Dot plot analyses or MFI (median fluorescence intensity) was calculated by either FCS EXPRESS™ software version 3.00.007 (Thornhill) or FLOWJO® software (version 7.6). To determine the sensitivity of anti-CD19scFv mAb (clone no. 136.20.1), CD19-specific $CAR^+$ T cells were mixed with PBMC obtained from healthy donors ($CAR^{neg}$ cells) at varying cell ratios (1:10-1:10,000 $CAR^+$ T cell to PBMC). ALEXA FLUOR® 647 dye conjugated mAb (clone no. 136.20.1) was used to detect $CAR^+$ T cells by flow cytometry.

TABLE 1

Antibodies used for flow cytometry analysis

| Antibody | Amount (μL) | Cat no. | Vendor |
| --- | --- | --- | --- |
| Rat Anti-mouse CD8α | 1 | 553033 | Becton and Dickinson, San Jose, CA |
| Goat anti-mouse IgG Fcg fragment specific PE | 1 | 115-096-071 | Jackson ImmunoResearch, West Grove, PA |
| Goat F(Ab)2 anti-human IgGg R-PE | 2.5 | H10104 | Invitrogen, Carlsbad, CA |
| Anti-CD19+ CAR Fc specific (2D3) | 1 | NA | Cooper Lab, MDACC |
| Anti-CD19+ CAR Idiotype 136.20.1-ALEXA FLUOR ® 647 dye-ALEXA FLUOR ® 488 dye | 1 | NA | Cooper Lab, MDACC |
| Anti-CD3 PE | 1 | 555333 | Becton and Dickinson, San Jose, CA |
| Anti-CD4 APC | 2.5 | 555349 | Becton and Dickinson, San Jose, CA |
| Anti-CD4 PercP Cy5.5 | 2 | 341654 | Becton and Dickinson, San Jose, CA |
| Anti-CD8 PercP Cy5.5 | 2 | 341051 | Becton and Dickinson, San Jose, CA |
| Anti-CD8 Pacific blue | 1 | 558207 | Becton and Dickinson, San Jose, CA |

Binding Assay.

Binding activity of purified anti-CD19scFv mAb (clone no. 136.20.1) was determined by an indirect ELISA. In brief, wells of a 96-well plate (Thermo Scientific Nunc) were coated with 100 ng of one of the following mAbs: anti-human CD19 mAb (clone FMC63, Millipore), anti-human CD19 mAb (clone MHCD1900, Gibco-Invitrogen), anti-human CD20 mAb (clone no. 1F5.1D4.1 derived by us from clone 1F5, clone no. HB-9645, ATCC), or human IgG (Jackson ImmunoResearch), in 0.1 mL of coating buffer (100 mM $NaHCO_3$ pH 8.6). The plates were incubated at 37°

C. for 1 h and then washed three times with PBST (1×PBS with 0.05% tween-20). Blocking was achieved with 300 µL of 5% BSA in PBST. A dose curve was generated using different concentrations of purified anti-CD19scFv primary mAbs (2-30 µg/mL) and detected by secondary antibody goat anti-mouse IgG Fc HRP (Sigma-Aldrich). Absorbance was read at 450 nm using a microplate reader (Victor 2030, Perkin Elmer).

Western Blot.

Reactivity of anti-CD19ScFv mAb (clone no. 136.20.1) to SDS-denatured protein was tested by western blot analysis. Ten million CAR modified or unmodified control T cells were lysed using RIPA buffer (50 mM Tris, pH 7.5, 150 mM NaCl, 0.1% SDS, 0.5% Sodium Deoxycholate, 1% TritonX100, 1 mM PMSF) containing protease inhibitor tablets as per the manufacturer's instructions (Roche Applied Science). Protein concentration was determined by a BCA kit (Thermo Scientific Pierce). Ten micrograms of total protein obtained from each cell lysates were electrophoresed under denaturing condition on a 4-20% gradient gel (Biorad) followed by electroblotting onto a PVDF membrane using a Criterion blotter (Biorad). PVDF membrane was blocked using 5% skim milk in PBST, and then incubated with primary anti-CD19scFv mAb (clone no. 136.20.1). Binding was detected by goat anti-mouse IgG Fc HRP (Sigma-Aldrich) enhanced with ECL WESTFEMTO™ substrate (Thermo Scientific Pierce). Images of blots were acquired on a gel doc image system using versa doc QUANTITYONE™ software (Biorad).

Microscopy.

For confocal microscopy, genetically modified T cells expressing CD19RCD28 CAR were fixed in 4% paraformaldehyde (EMS Inc.) and stained with ALEXA FLUOR® 647 dye conjugated anti-CD19scFv mAb (clone 136.20.1) at 1:500 using a standard protocol. Labeled cells were added with PROLONG® gold anti-fade reagent with DAPI (Gibco-Invitrogen) and viewed under a confocal microscope (Leica Microsystems). For TEM, CAR$^+$ T cells were fixed in 1% glutaraldehyde (Sigma-Aldrich) followed by washing with PBS. The cells were then incubated in 20 mM glycine-PBS followed by washing with PBS-BSA buffer (20 mM phosphate, 150 mM NaCl, pH 7.4 containing 0.5% BSA and 0.1% gelatin). NANOGOLD® antibody conjugates were diluted 1:50 in PBS-BSA buffer and incubated with CD19-specific CAR$^+$ T cells for 15 min followed by washing with the same buffer to remove unbound conjugates. Finally, NANOGOLD® bound cells were fixed with 1% glutaraldehyde and stored at 4° C. until further use. Before sectioning, cells were subjected to an alcohol dehydration steps (5% to 100% graded alcohol separated in 5 steps) followed by embedding in epoxy resin. The resin embedded cells were then cut into sections (1 µM to 100 nm thickness) in an ultra-microtome (Leica Microsystem). Sections were drawn onto a formavar coated copper grid. Staining was done by 2% uranyl acetate and then air dried. Unstained samples underwent silver enhancement (Nanoprobes) so that surface bound NANOGOLD® particles could be visualized. High magnification images were acquired by a 1 k×1 k CCD camera attached to a JEM-1200 EX60KV electron microscope (JEOL).

Chromium Release Assay (CRA).

The functionality of anti-CD19scFv mAb was assessed in a CD19-specific CAR$^+$ T cell-mediated cytolysis in a standard 4 h chromium ($^{51}$Cr) release assay (CRA) employing parental CD19$^{neg}$ EL4, CD19$^+$ EL4, CD19$^+$ Daudiβ$_2$m, and CD19$^+$ NALM-6 as targets (Singh et al., 2008; Singh et al., 2011). Effector cells (ex vivo expanded CD19RCD28 CAR$^+$ T cells harvested on day 28) were incubated with various concentrations of purified mAb (clone 136.20.1) at 10-fold serial dilution (maximum dose at 250 µg/mL and minimum at 1.25 µg/mL) for 20 min at 4° C., followed by washing with RPMI 1640 to remove unbound antibodies. The antibody-bound effector cells were incubated with $^{51}$Cr labeled target cells in a clear v-bottom 96-well plate (Corning) at 37° C. Release of $^{51}$Cr was quantified in a micro-plate scintillation counter TopCount NXT (Perkin-Elmer). Specific lysis was calculated for effector to target cell (E:T) ratios in the presence and absence of anti-CD19scFv mAb. Data were reported as mean±standard deviation (SD).

Video Time Lapse Microscopy (VTLM).

CD19-specific T cells expressing CD19RCD28 CAR were washed in sterile 1×PBS and stained for 30 min at room temperature using ALEXA FLUOR® 647 dye-conjugated to anti-CD19ScFv mAb (clone no. 136.20.1) at 2 µg mAb per 100,000 cells and then washed three times with 1×PBS. The CAR$^+$ T cells were mixed together with EGFP$^+$ Daudiβ$_2$m at an effector to target ratio of 2:1. A cell pellet was made by brief centrifugation and then re-suspended in media RPMI 1640 and put in one of the chamber of a 35 mm culture dish (Nikon). This was kept in the specimen chamber of BIOSTATION® IM cell incubator and monitoring system (Nikon) and allowed to settle for 10 min. CCD camera focal planes were fixed and the effector to target cell dynamics were assessed for 2 to 12 hours using imaging software (IM-Q, v2.1.2.136, Nikon). As control, APC-conjugated goat anti-human IgG Fcγ chain specific F(ab')$_2$ fragment antibody (Jackson ImmunoResearch) was used to bind CAR$^+$ T cells and the co-culture was set up as described.

Indirect ELISA to Detect Antibody Titer and Screen Positive Hybridoma Clones.

The assay was performed by coating flat-bottom well of a 96-well MEDISORP™ plate (Thermo Scientific Nunc) with parental L cells or L cells transfected with CD19scFvmCD8α. Approximately 250,000 cells were coated per well in 50 µL of sodium phosphate buffer (pH 7.4). Plates were left overnight in laminar airflow hood for cell binding and drying and stored at −20° C. until use. To block non-specific binding, 2% BSA in PBST (1×PBS containing 0.05% Tween-20) was dispensed at 300 µL per well. Unbound cells were washed with PBST. Various dilutions of sera (1:100 to 1:3,000) or antibody supernatant (1:2-1:10) were allowed to bind with the coated cells/antigen for 1 h at room temperature (RT). After washing with PBST, secondary antibody anti-mouse IgG Fc HRP (Sigma-Aldrich) was added at 1:5,000 dilution and incubated for 45 min at room temperature. Detection of the bound antibody was performed after addition of 1×TMB/H$_2$O$_2$ substrate (Sigma-Aldrich). Absorbance was measured at 450 nm using a microplate reader (Victor 2030, Perkin Elmer). Cross reaction of immune sera and hybridoma supernatant with parental L cells was measured at OD$_{450}$ and used as background controls. For transfected cells, wells showing OD$_{450}$ values 3 times above background controls were marked positive. Random wells were viewed by microscopy before and after washing to ensure no loss of cells occurred during the process. The isotype of mAbs were determined using a mouse immunoglobulin isotyping kit (BD Biosciences). Positive clones were identified and expanded further in 1× HT (Sigma-Aldrich) supplement media. Sub-cloning was performed by standard limiting dilution method to obtain a monoclonal population. Monoclonal antibodies were purified using protein G or protein A columns (GE Life Science).

Antibody Purification and Conjugation.

One CD19scFv specific clone (no. 136.20.1) was grown and expanded further in vitro or injected in mice for ascites production (Harlan Inc.). Monoclonal antibodies from the culture supernatant or ascites were obtained by standard protein G or A (GE Life Science) purification using 0.1 M glycine (pH 2.7) as elution buffer. Affinity eluted and neutralized antibodies were dialyzed extensively against PBS and subjected to flow cytometry analysis for final validation and use in cell culture assays. Purified antibodies were conjugated to different fluorochromes viz., ALEXA FLUOR® 488 dye and ALEXA FLUOR® 647 dye (Molecular Probes-Invitrogen) using a commercially available kit that exploits the principle of conjugation through succinimidyl ester moiety to primary amines of proteins/immunoglobulins to form stable dye-protein conjugates. Fluorochrome-conjugated antibodies were subjected to gel filtration chromatography to remove unbound dye. For transmission electron microscope (TEM) studies, antibodies were conjugated to gold nanoparticles. In brief, antibodies were reduced by adding 1 mL of purified mAb (2 mg/mL) to 6 mg of mercaptoethylamine hydrochloride (MEA) (Thermoscientific-Pierce) and then purified on a gel filtration column MatrexGH25 (Millipore, Billerica, Mass.). Reduced antibodies were labeled with monomaleimido NANOGOLD® (Nanoprobes), as per the manufacturer's instructions, and purified on a gel filtration column Superdex-75 (Sigma-Aldrich) to remove unbound NANOGOLD®. The final concentration of the purified antibodies was measured by a BCA kit (Thermoscientific Pierce).

Immunohistochemistry.

CD19-specific CAR+ T cells were propagated as described. Cells were harvested, washed in 1×PBS and then fixed in formalin. Five micron paraffin-embedded sections were made and stained. In brief, sections were blocked initially with 3% hydrogen peroxide and whole goat sera blocking reagent for 5 minutes, followed by incubation with primary antibody anti-Id CAR idiotype for 30 minutes. Biotinylated goat anti-mouse IgG-HRP was used as secondary antibody at 1:500 for 30 minutes, followed by incubation with streptavidin-HRP for 15 minutes. Cells were localized with DAB (diaminobenzidine) for 5 minutes. Slides were counterstained with Mayer's hematoxylin for 5 minutes, dehydrated and mounted with a cover slip. Photographs were taken using a confocal microscope (Leica Microsystems).

Methodology to Derive Antibody Variable Region Sequence.

The antibody variable heavy chain ($V_H$) and light chain sequences ($V_L$) were derived after amplifying the $V_H$ and $V_L$ using sets of degenerate primers annealed to either variable heavy or light chain constant regions of monoclonal antibody (clone 136.20.1) cDNA. The PCR-amplified product was cloned into PCR4 TOPO vector (Invitrogen) and then sequenced. Consensus sequences were identified after aligning sequences obtained with T3 forward and T7 reverse primed pCR4 TOPO TA vector inserted with 136.20.1 $V_H$ or $V_L$ PCR product. Sequence alignment was performed in Vector NTI 11 (Invitrogen). CDR sequences of the monoclonal antibody were analyzed from the cDNA amplified sequences using IMGT software (on the world wide web at imgt.org/IMGT_vquest/vquest?livret=0&Option=mouseIg).

Example 2—CD19 CAR-Targeting Monoclonal Antibody—Results

Generating Anti-ScFv mAb Recognizing CD19RCD28 CAR.

BALB/c mice were immunized using L cells (derived from C3H/An mouse strain) genetically modified to express the scFv region in a CD19-specific CAR (FIG. 7). The scFv was derived from FMC63 (encoded in DNA plasmid CD19scFv-mCD8α) and stably expressed (>90% homogenous expression after single-cell sorting) on the surface of neomycin-resistant genetically modified L cells, which was used to immunize allogeneic mice. The murine CD8α transmembrane and extra-cellular region were used to display scFv on the surface and to detect expression (FIGS. 1B and 1C). Genetically modified L cells were injected in mice at 3 day intervals and high titer sera (OD values~5 times above background at 1:2,700 dilution) was obtained after five successive immunizations. Hybridomas were generated and ELISA was used to initially select 23 "high binders" ($OD_{450}$>1.5) and 15 "moderate binders" ($OD_{450}$~1.00-1.5) to advance to the second round of screening. Flow cytometry using Jurkat and NS0 cells genetically modified with CD19scFv-mCD8α was used to cull the number of candidate hybridomas to 12. One clone was selected (no. 136.20.1; Table 2) that could efficiently bind CD19RCD28 expressing cells by flow cytometry. The absence of adjuvant at the time of immunization did not affect the antibody affinity maturation process as the obtained mAb clones were predominantly of $IgG_{2a}$ sub-class. Immunization by genetically modified L cells provides an efficient method for eliciting desirable anti-idiotype immune response.

TABLE 2

Sequence of CD19scFv-specific mAb clone 136.20.1

| mAb | Heavy Chain Sequence | | | Light Chain Sequence | | |
|---|---|---|---|---|---|---|
| | CDR1 | CDR2 | CDR3 | CDR1 | CDR2 | CDR3 |
| | Amino acid sequence | | | Amino acid sequence | | |
| 136.20.1 | GFDFSRYW (SEQ ID NO: 2) | INLDSSTI (SEQ ID NO: 3) | ARRYDAMDY (SEQ ID NO: 4) | ESVDDYGISF (SEQ ID NO: 6) | AAP (SEQ ID NO: 7) | QQSKD (SEQ ID NO: 8) |
| | LKPREVKLVESGGGLVQPGGSLKLSCA ASG<u>FDFSRYW</u>MSWVRQAPGKGLEWIGE <u>INLDSSTI</u>NYPSLKDKFIISRDNAKN TLYLQMSKVRSEDTALYYC<u>ARRYDAMD Y</u>WGQGTSVTVSSAKTTAPSVYPLAPVC GDTTGSSVTLGCLVKASQ (SEQ ID NO: 1) | | | ASDIVLTQSPASLAVSLGQRATIS CRAS<u>ESVDDYGISF</u>MNWFQQKPGQ PPKLLIY<u>AAP</u>NQGSGVPARFSGSG SGTDFSLNIHPMEEDDTAMYFC<u>QQ </u><u>SKD</u>VRWRHQAGDQTG (SEQ ID NO: 5) | | |

Specificity of mAb (Clone No. 136.20.1) for CD19scFv.

Figures 2A, 2B:
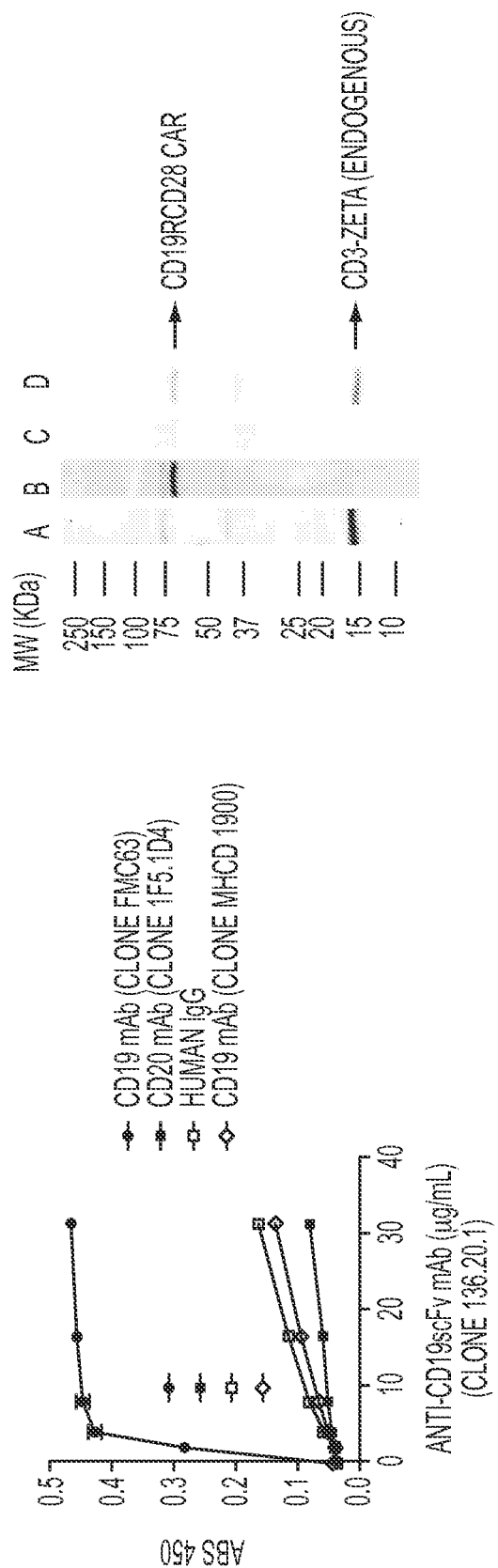
FIG. 2. Specificity of anti-CD19scFv mAb. (A) Solid phase ELISA shows specificity of mAb (clone no. 136.20.1) as it binds to parental monoclonal antibody (FMC63) with background binding to other antibodies (e.g., CD20-specific mAb or a different CD19-specific mAb). Purified human IgG served as a negative control. (B) Western blot shows clone 136.20.1 detects CAR protein in T cells genetically modified to express CD19RCD28. Lane A: Unmodified control T cells show endogenous CD3ζ (14 kDa) as detected by commercial CD3ζ-specific antibody and absence of CAR. Lane B: CAR$^+$ T cells show CAR-specific band at 75 kDa as detected by mAb (clone 136.20.1). Lane C: CAR$^+$ T cells show absence of CAR-specific band when the blot is treated with primary antibody after blocking (clone 136.20.1 was blocked with molar excess (1:5) of parental antibody FMC63). Lane D: CAR$^+$ T cells show the presence of CAR (~75 kDa) and endogenous CD3ζ (14 KDa) as detected by commercial CD3ζ-specific antibody.
Figure 3B:
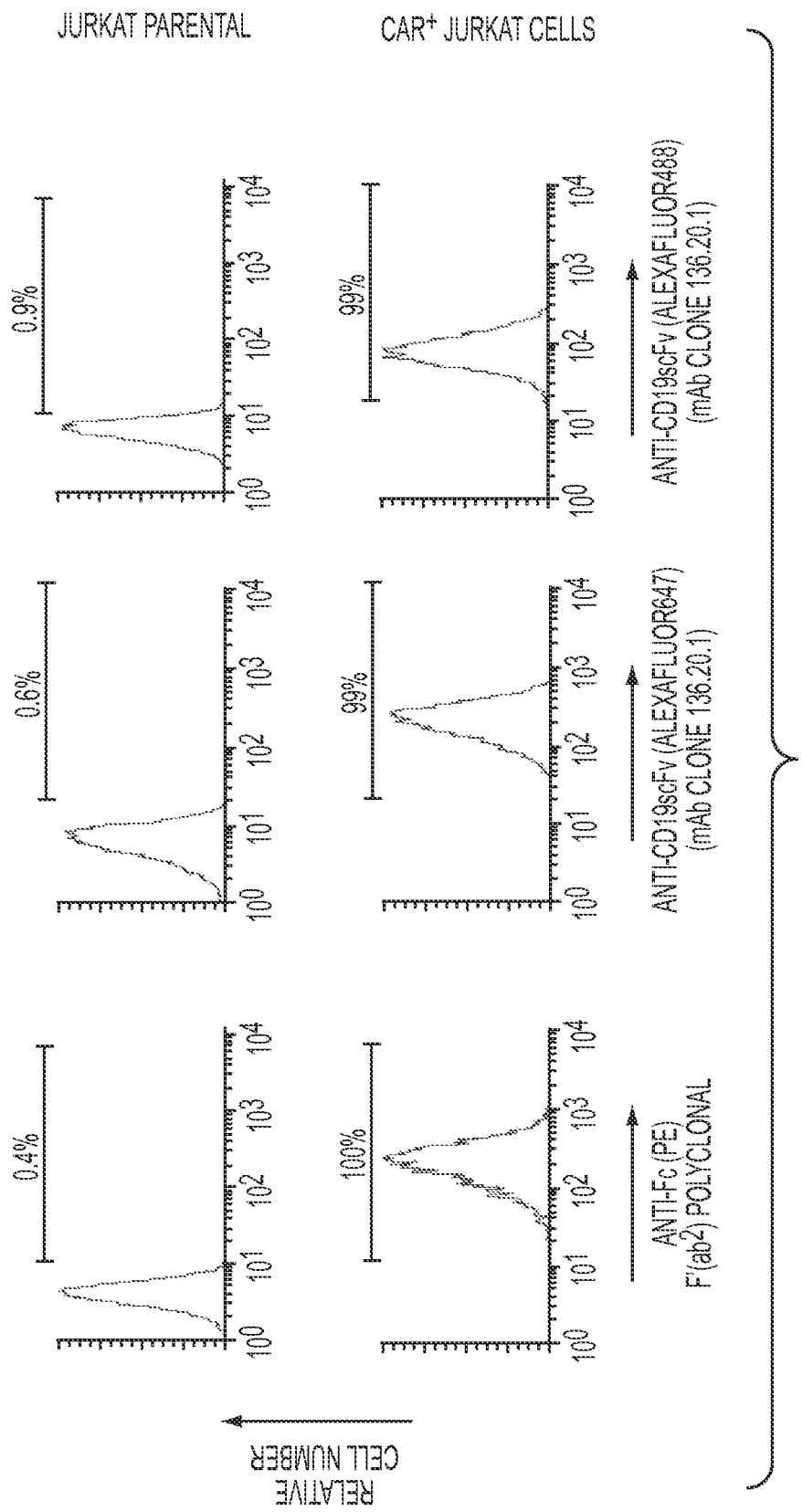

The specificity of mAb (clone no. 136.20.1) towards CD19scFv was initially evaluated by an indirect ELISA with wells coated with purified mAbs. Except for parental anti-human CD19 mAb (FMC63) all other antibodies exhibited negligible cross reactivity to CD19scFv specific mAb (FIG. 2A). Anti-CD19scFv binds to its parental mAb at concentrations as low as 2 µg/mL with binding saturated at 4 µg/mL. The specificity of this mAb towards clone FMC63 was confirmed as it did not cross react to another anti-human CD19 antibody (Invitrogen, clone MHCD 1900). Further, it did not bind to purified human IgG and CD20-specific mAb. The ability of mAb (clone no. 136.20.1) to detect CD19$^+$ CAR protein was verified by western blot using whole protein lysates obtained from ex vivo-propagated CD19-specific CAR$^+$ T cells. MAb (clone no. 136.20.1) detected a ~75 kDa protein in CD19RCD28 modified cell lysates run in reducing SDS-PAGE and electroblotted onto PVDF membrane (FIG. 2B, lane B). The specificity was verified in parallel by a commercially available CD3ζ antibody which detects the CD3ζ signaling domain in CD19RCD28-expressing CAR (FIG. 2B, lane D) and endogenous CD3ζ in unmodified control T cells (FIG. 2B, lane A). The ability of this mAb to detect the surface expression of CD19$^+$ CAR was verified by flow cytometry analysis using CD19RCD28-expressing primary T cells and Jurkat cells (FIGS. 3A and 3B, respectively). MAb (clone 136.20.1) detected expression of CD19scFv on the surface of genetically modified T cells (85%) as well as in Jurkat cells (99%) which matches with detection level of anti-Fc antibodies that binds to the CH$_2$—CH$_3$ stalk of the CAR. Indeed, the staining pattern was compared with commercial IgG-γ chain-specific antibodies (Fc-PE Invitrogen) that bind to the CH$_2$—CH$_3$ region of the CAR and by mAb clone no. 2D3 developed in-house which binds to the CH$_2$—CH$_3$ hinge region of the CAR (Fc-FITC) (Singh et al., 2008). A panel of CAR$^+$ T cells that target different TAAs (CD33, CD123, ROR1, HERV-K) were used to verify if clone no. 136.20.1 cross reacted with any of these CAR transgenes. Each CAR construct was expressed from the Sleeping Beauty vector backbone and contained different signaling endodomains in addition to the common IgG$_4$-derived hinge/CH$_2$—CH$_3$ linker. It did not cross react with any of other CARs tested other than those with specificity for CD19 (FIG. 8). No background binding to mock-electroporated control T cells was observed. Additional evidence supporting specificity of mAb (clone no. 136.20.1) are provided (FIGS. 9 and 10). In both cases CAR scaffold differs either by the presence of human CD4 transmembrane region or IgG$_1$ Fc stalk that connects the scFv with the signaling endodomains. Furthermore, the mAb has been used to detect CD19-specific CAR$^+$ T cells that employ an extracellular domain derived from CD8α (Kalos et al., 2011; Porter et al., 2011). These results demonstrate that, irrespective of extra-cellular scaffolding and transmembrane domains, the mAb (clone no. 136.20.1) detects CD19scFv within CAR expressing scFv derived from FMC63.

Figure 3C:
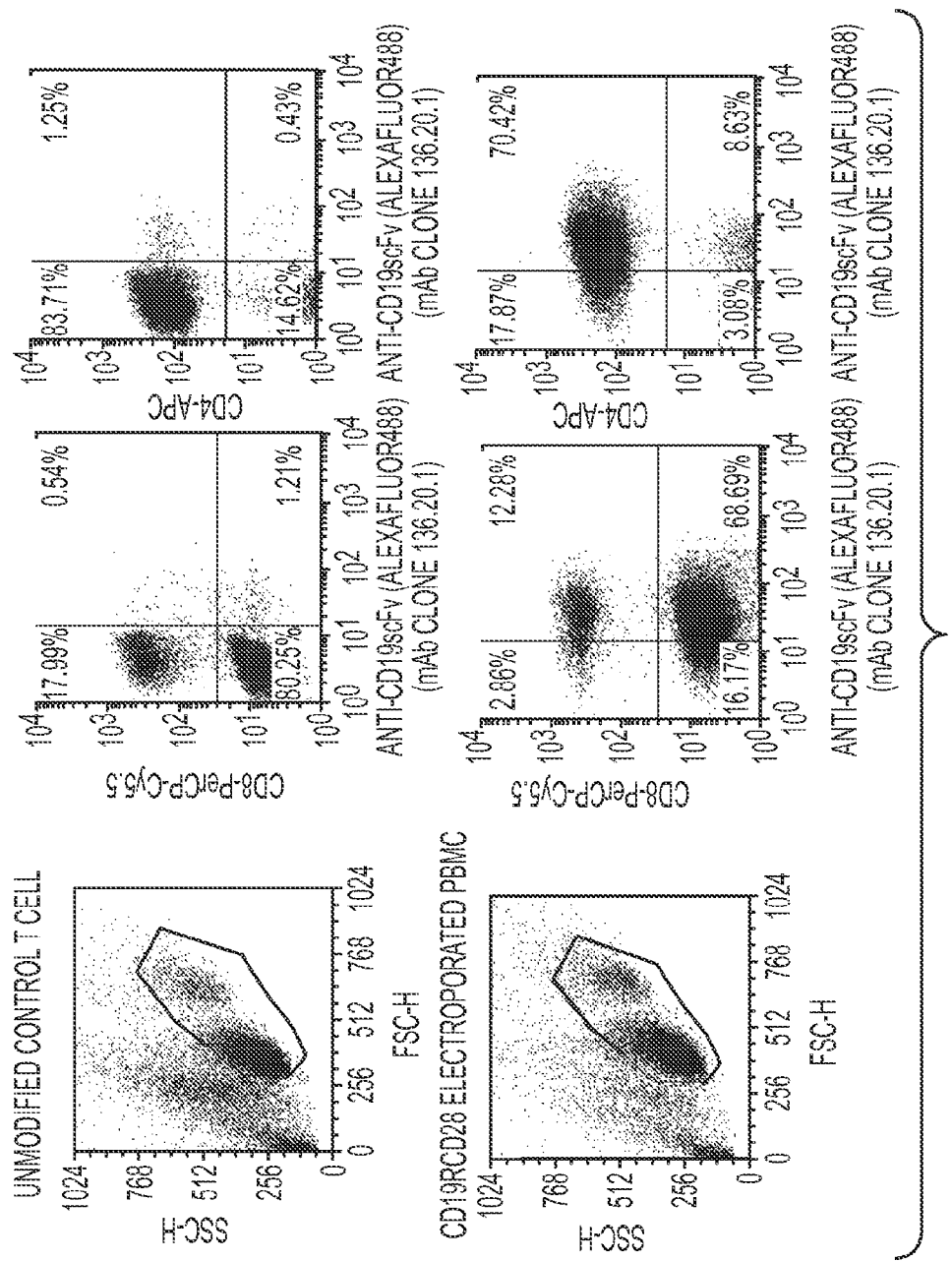
Figure 4:
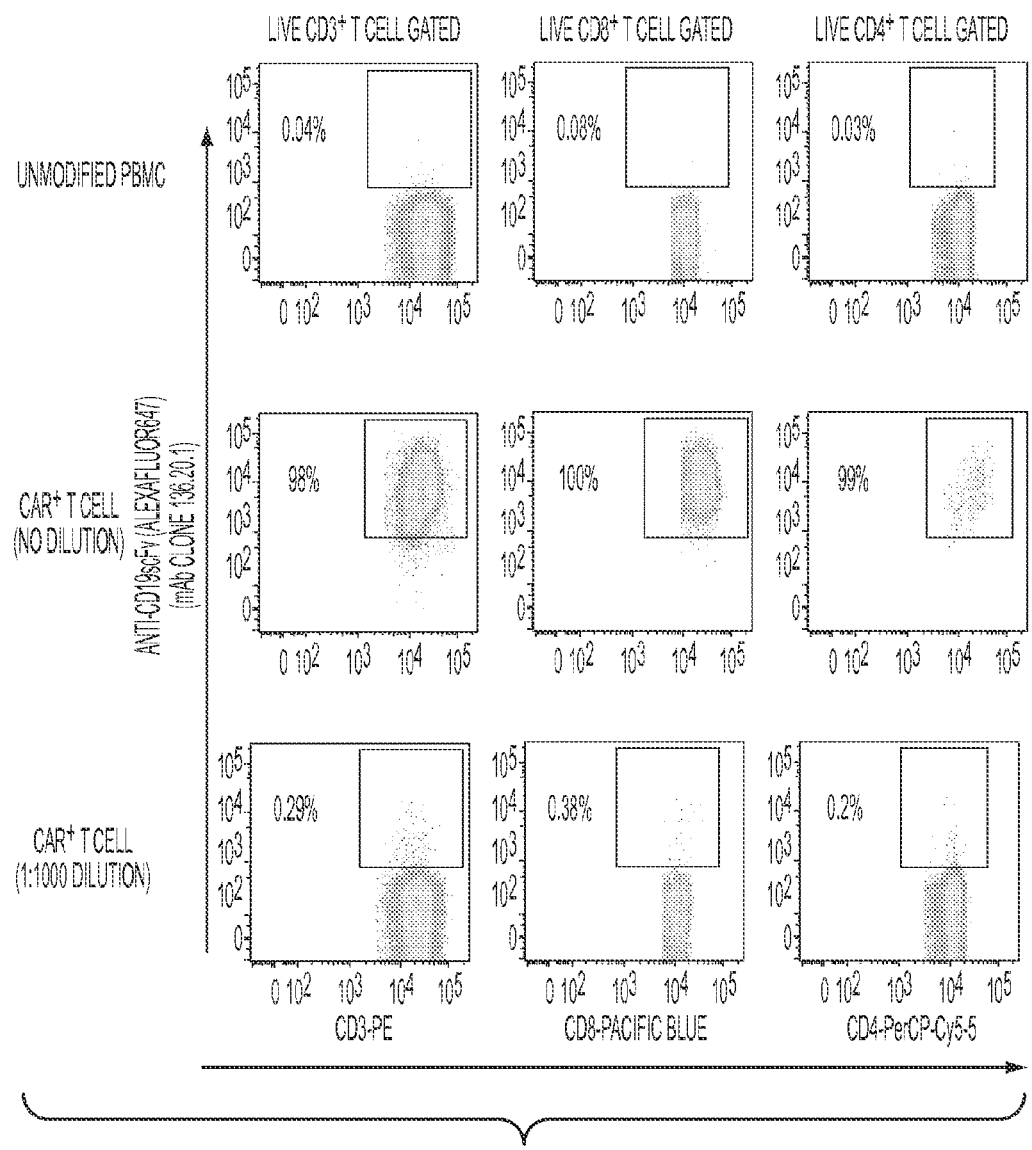

The anti-CD19scFV mAb (clone no. 136.20.1) could be used in multi-parameter flow cytometry analysis to characterize CAR$^+$ cells selectively propagated on K562-derived aAPC (Jena et al. 2013). CAR-modified T cells were numerically expanded in the presence of irradiated aAPC and cytokines (IL-2 and IL-21) for 4 weeks as previously reported (Singh et al., 2011). The anti-CD19scFV mAb (clone 136.20.1) could detect both CD4$^+$ and CD8$^+$ CAR$^+$ T cells (FIG. 3C). The inventors assessed the limit of detection using a spiking experiment. As shown in FIG. 4, the inventors were able to detect one CD19-specific CAR$^+$ T cell in 1,000 PBMC using anti-CD19scFV tagged to a ALEXA FLUOR® 647 dye. The assay was validated in PBMC obtained from two individual donors by an independent laboratory (Immune Monitoring Core lab) at MDACC (Representative data along with dilution schematic and gating strategy are provided in FIG. 9(i-iii). The anti-CD19scFV mAb could help in detecting the presence of CAR$^+$ T cells in patients after infusion (demonstrating the detection of CAR$^+$ T cells with central memory immunophenotype in PBMC).

Figure 5A:
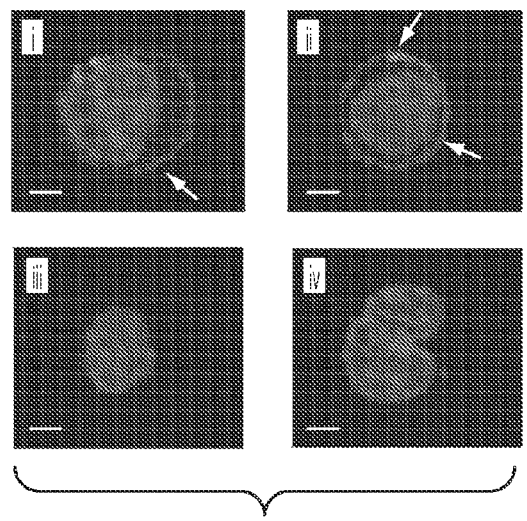
Figure 5B:
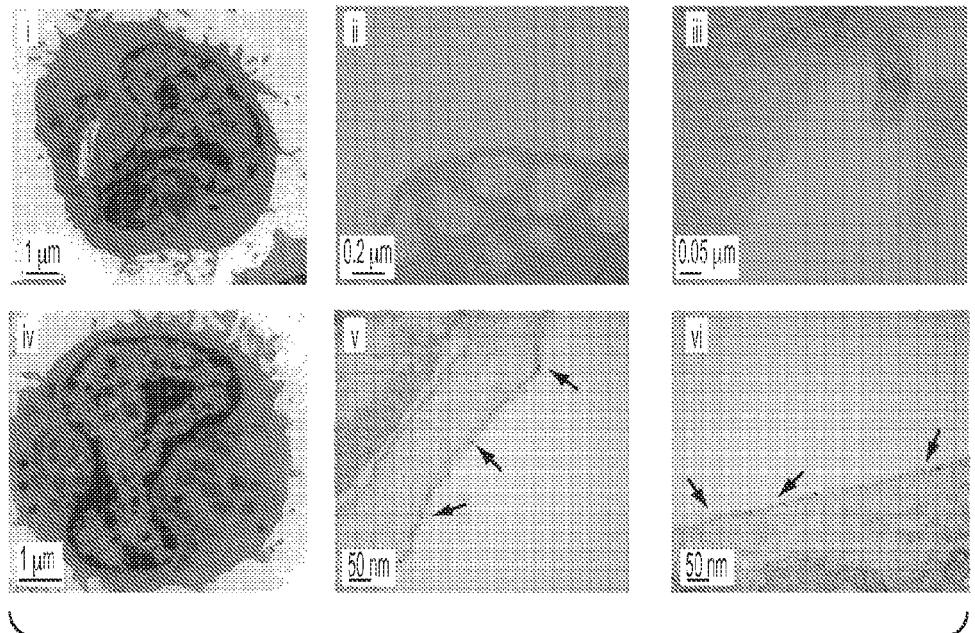

Persistence of adoptively transferred CAR$^+$ T cells in patients correlates with efficacy in eradicating tumor. The inventors desired that clone no. 136.20.1 be used in correlative studies pertaining to clinical trials that infuse CAR$^+$ T cells and thus wanted to check if this mAb could detect CAR$^+$ cells preserved in various harsh organic solvent fixatives. CARs could be detected by immunocytochemistry and TEM. At day 28 of culture CD19-specific CAR$^+$ T cells were harvested and fixed by paraformaldehyde. FIG. 5A shows that anti-CD19scFv mAb, when used at a concentration of 1:500, can establish surface localization of CARs in genetically modified T cells by immunocytochemistry. The inventors have also established the utility of this mAb in immunohistochemistry using CAR$^+$ T cells fixed in neutral buffer formalin (FIG. 10) and are currently working to detect CAR$^+$ T cells in bone marrow of patients infused with CD19-specific CAR$^+$ T cells. To detect CAR molecules on surface of genetically engineered T cells by electron microscopy, mAb (clone no. 136.20.1) was tagged to gold-labeled nanoparticles. Control unmodified T-cell sections are shown in FIG. 5B (i-iii). The size of the conjugated NANOGOLD® (1.4 nm) precluded detection within thick sections of CAR$^+$ T cells (FIG. 5B (iv)). Thus, the inventors performed a silver enhancement process and could view CARs as detected by clone no. 136.20.1 conjugated nanoparticles within 100 nm thin sections (FIG. 5B (v-vi)). The silver enhancement was performed on non-stained samples as uranyl acetate staining prevented distinguishing nanoparticles from other cellular granules. These studies establish the utility of clone no. 136.20.1 to detect CAR$^+$ T cells in fixed sections.

Anti-CD19scFv mAb can Block the Effector Function of CAR$^+$ T Cells.

The inventors evaluated functional properties of anti-CD19scFv mAb (clone no. 136.20.1) based on its ability to prevent lysis mediated by CD19-specific CAR$^+$ T cells. Previously, the inventors developed and validated an approach for ex vivo expansion of genetically modified CAR$^+$ T cells on artificial antigen presenting cells (K562 clone #4). CAR$^+$ T cells receive proliferative signals from the TAA (CD19) coordinated with co-stimulatory molecules (CD86, CD137L, membrane bound IL15) cloned onto the surface of K562 cells (FIG. 3C) (Singh et al., 2008; Manuri et al., 2009; Singh et al., 2011). The CD19-specific CAR$^+$ T cells used in this study were propagated on the same K562-derived aAPC. A standard 4 h CRA was performed using mouse T-cell lines EL4 (parental) and CD19$^+$ EL4 as the tumor target. The percentage specific lysis was calculated using CD19-specific CAR$^+$ T cells bound to CD19scFv mAb or CD19-specific CAR$^+$ T cells alone. FIG. 6A shows that anti-CD19ScFv mAb completely inhibits CAR-dependent killing (at 250 µg/mL) by blocking the ability of CAR to dock to the TAA. However, at 25 µg/mL the anti-Id inhibited killing at 30% maximum and there was little or no effect when the mAb concentration was reduced to 5 µg/mL (FIG. 6B). The inventors repeated the experiment in two other B-cell lines (Daudiβ$_2$m and NALM-6) to validate that inhibition of lysis could be achieved in alternate B-cell tumors. The application of anti-CD19scFv at 250 µg/mL reduced the cytolytic activity to 18% in Daudiβ$_2$m and 32% in NALM-6 (FIG. 11). However, the mechanism of lysis may not be same in all these tumor cell lines and hence the degree of inhibition differed. To investigate the inhibitory effect of anti-CD19scFv mAb in real time, the inventors used VTLM to serially monitor the killing process in a co-culture experiment involving Daudiβ$_2$m as a tumor target and CD19-specific CAR$^+$ T cells as effectors. As a control, the inventors used a Fc-specific F(ab')$_2$ fragment of an antibody that bound to the scaffolding of CD19RCD28. CAR$^+$ T cells continued to lyse tumor cells when the effector cells were bound by this control antibody (FIG. 6i-iii). In contrast, CAR$^+$ T cells were unable to kill target cells when bound by anti-CD19scFv mAb (FIG. 6iv-vi). Thus, blocking by clone no. 136.20.1 prevented triggering of T cells, which supports the claim that this mAb binds within the scFv domain of the CAR.

Example 3—A Novel CAR-Targeting Functional Monoclonal Antibody (2D3) Amenable for CAR-Mediated Gene Therapy Targeting tumor antigens through gene modified immune cells has increasingly been adopted by clinical oncologists, thanks to the ability of these cells to eradicate tumors that have been otherwise refractory to conventional therapies. The clinical trials conducted so far showed encouraging results. There is an increasing demand to place specific reagents so that isolation, activation, and functional characterization of these gene modified cells are possible. In this context, the inventors developed a Chimeric Antigen Receptor (CAR)-specific monoclonal antibody (2D3) that possesses unique ability to detect all chimeric antigen receptor (all CAR)-modified immune cells (FIG. 12). The 2D3 antibody employs the immunoglobulin heavy chain constant region to cross-link the T cell signaling endodomain with antigen binding domain of a CAR. This antibody has multiple functions, such as detection (FIG. 12), quantification, activation, and selective propagation (FIG. 13) of CAR modified cells, and hence will likely be an important reagent suitable for CAR-modified gene therapy.

A novel and promising form of cancer therapy genetically modifies a patient's own T cells in peripheral blood to target and kill their cancer using a chimeric antigen receptor (CAR) directed against a tumor associated antigen (TAA). Growing a therapeutic number of CAR$^+$ T cells to treat cancer patients requires an artificial antigen presenting cell (aAPC) to express the TAA that the CAR$^+$ T cell targets. Antigen-specific growth using a cell based system requires at least a month of intensive monitoring for outgrowth of unwanted cell types. Here, the inventors provide a system that decreases the high cost and time associated with manufacturing a different aAPC for each TAA and decreases the time and effort needed to develop, validate, and manufacture large numbers of CAR$^+$ T cells. An HLA-null K562 (HnK) was modified to surface express a chimeric antibody receptor that could bind to spacer domain present in all to all other CARs produced by the inventor's lab which are G4CAR. In another aspect, the specified spacer domain (Hinge-CH2-CH3) may also be used for CAR expression. When peripheral blood mononuclear cells (PBMC) are genetically modified to express a CAR containing this domain, those CAR' PBMC can be co-cultured with G4CAR$^+$ HnK (G4HnK) to specifically grow CAR$^+$ T cells independent of TAA. Utilizing G4HnKs to grow CAR$^+$ T cells generates a sufficient number of CAR$^+$ T cells for therapy in half the amount of time typically needed utilizing antigen-specific aAPC. The T cells consistently grow without competition to a pure population within 2 weeks (>80% CAR$^+$ T cells), and this level of infusion product purity is rarely achieved using current aAPC before one month of T cell co-culture with standard aAPC. Also unique to this system is the capacity to expand antigen non-specific CAR$^+$ T cells as a means of antibody-independent T cell growth without tissue targeting. This provides a novel method of expanding CAR modified T cells developed on a common backbone but targeted to alternate tumor antigens. In conclusion, the inventors have made a single aAPC cell line capable of expanding any CAR$^+$ T cell independent of a CAR-specific antigen.

TABLE 3

Sequence of All CAR mAb 2D3

| mAb | Heavy Chain Sequence | | | Light Chain Sequence | | |
|---|---|---|---|---|---|---|
|  | CDR1 | CDR2 | CDR3 | CDR1 | CDR2 | CDR3 |
|  | Amino acid sequence | | | Amino acid sequence | | |
| 2D3 | GYTFTSYW (SEQ ID NO: 10) | IYPGNSDT (SEQ ID NO: 11) | TRVNWDG YSTMDY (SEQ ID NO: 12) | QSLVHSN GNTY (SEQ ID NO: 14) | KVS (SEQ ID NO: 15) | CSQTTHV PYTF (SEQ ID NO: 16) |
|  | PREXKLEQSGTVLARPGASVKMSCKTS<u>GYT FTSYWMHWV</u>IQRPGQGLEWIG<u>AIYPGNSDT</u> NYNQKFKVKAKLTAVTSTSTAYMELSSLTD EDSAVYYC<u>TRVNWDGYSTMDY</u>WGQGTSVTV SSAKTTPPSVYASQRANSRP (SEQ ID NO: 9) | | | STLSLPVSLGDQASISCRSS<u>QSLVH SNGNTY</u>FHWYLQKPGQSPKLLIYK<u>V SNRFSGVPDRFSGSGSGTNFTLKIS RVEAEDLGVYFC<u>SQTTHVPYTF</u>GGG TELEIKRADAAPTVS (SEQ ID NO: 13) | | |

Example 4—Universal Artificial Antigen Presenting Cells to Selectively Propagate T Cells Expressing Chimeric Antigen Receptor Independent of Specificity Cells and Culture Conditions.

K562 cells (European Collection of Cell Cultures through Sigma-Aldrich, St. Louis, Mo.; Cat. No. 89121407), noted for expression of desired endogenous adhesion molecules and the absence of most HLA class I and all class II molecules, (Suhoski et al. 2007) were used to derive CD19$^+$ and CARL$^+$ K562 that served as aAPC. Immortalized tumor targets CD19$^{neg}$, GD2$^+$ EL-4 murine thymoma (Cat. No. TIB-40) and CD19$^+$, GD2$^{neg}$ NALM-6 (pre-B cell leukemia, Cat. No. CRL-1567) were purchased from American Type Culture Collection (ATCC, Manassas, Va.). Identity of cell lines was validated by the MDACC Cancer Center Support Grant Characterized Cell Line Core using short tandem repeat DNA fingerprinting. Peripheral blood was donated by consenting healthy volunteer adults at Gulf Coast Regional Blood Center (Houston, Tex.). Peripheral blood mononuclear cells (PBMC) were isolated using Ficoll-Paque Plus density centrifugation (GE Healthcare Biosciences, Piscataway Township, N.J.; Cat. No. 17-1440-02) before freezing in a mixture of 10% DMSO (Sigma, Allentown, Pa.; Cat. No. D2650), 50% heat-inactivated fetal bovine serum (FBS-Thermo Scientific Hyclone, Bridgewater, N.J., Cat. No. SH30070.03), and 40% RPMI 1640 (Thermo Scientific Hyclone; Cat. No. SH30096.01). All cells were cultured in a 37° C. humidified incubator with complete media (CM) prepared from RPMI 1640, 10% heatinactivated FBS, and 2 mM GlutaMAX supplement (Life Technologies, Grand Island, N.Y.; Cat. No. 35050061).

DNA Expression Plasmids.

Codon-optimized CD19RCD28mZ(CoOp)/pSBSO, (Singh et al. 2008) which codes for CAR between transposition sites mediated by SB transposase, (Davies et al. 2010) was used as the vector backbone for cloning of the following transgenes. The DNA plasmid 19G4CAR (also designated CD19RCD28 [Kowolik et al. 2006] FIG. 19A) codes for a 2$^{nd}$ generation CD19-specific CAR containing a modified IgG4 exodomain, CD28 transmembrane, and CD28/CD3ζ endodomain. The synthesis of DNA plasmid GD2G4CAR (FIG. 19B), specific to sphingolipid GD2, utilized the same 19G4CAR backbone. The GD2-specific scFv derived from murine mAb (clone 14G2a) (Alvarez-Rueda et al. 2011) was commercially synthesized (Geneart, Life Technologies) as codonoptimized cDNA with NheI and XmnI restriction enzyme (RE) sites flanking the scFv. The 19G4CAR plasmid backbone and GD2-specific scFv cDNA were excised using these REs and ligated to replace CD19-specific scFv with GD2-specific scFv. A DNA plasmid (FIG. 19C) coding for a control CAR that contains no scFv region, designated G4CAR, but does contain an Igκ-FLAG peptide sequence (METDTLLLWVLLLWVPGSTGDYKDEGTS; SEQ ID NO: 19), was derived from 19G4CAR using primer-directed PCR amplification from the beginning of the IgG4 domain hinge (primer 5'GGTACCTCTGGGGGGCAGGGCCTG-CATG3'; SEQ ID NO: 20) to the terminus of the CD3ζ domain (primer 5'GGGCCCAGCGCTGAGAGCAAG-TACGGCCCTCCC3'; SEQ ID NO: 21) and sequence verified. The G4CAR was ligated into the 19G4CAR backbone ApaI and KpnI RE sites. DNA plasmid coding for a CD19-specific CAR with no IgG4 (FIG. 19D), designated 19CAR, encodes from amino to carboxyl termini a GM-CSF (amino acid 1-22; NP_758452.1 (SEQ ID NO: 22)), CD19-specific scFv (245 amino acids), CD8α extracellular domain and hinge (amino acids 136-203; NP_001759 (SEQ ID NO: 23)) followed by the same CD28 transmembrane and CD28 and CD3ζ domains as other CARs. (Kowolik et al. 2006) The full length of this transgene was synthesized by GeneArt, cut with ClaI and SpeI REs, and ligated into the 19G4CAR backbone replacing the 19G4CAR codon, which had been excised using EcoRV and SpeI. The scFv sequence of CARL was derived from the cDNA library of the 2D3 hybridoma. (Singh et al. 2008) This was achieved by extracting RNA from 5×10$^6$ cells using the RNeasy Mini Kit (Qiagen, Gaithersburg, Md.; Cat No. 74104) according to manufacturer's protocol. A cDNA library was generated by reverse transcription using oligo-dT primers per the protocol provided in the Superscript III First Strand kit (Invitrogen; Cat No. 18080-051). PCR (using Amplitaq Gold) was performed on the cDNA using the degenerate primers for the FR1 region (Wang et al. 2000) to amplify the mouse VH and VL regions. The VH and VL amplified products were ligated into the TOPO TA vector and sequenced. The CARL construct for surface expression on aAPC was composed of GM-CSF leader peptide (amino acid 1-22; NP_758452.1 (SEQ ID NO: 22)) fused to the 2D3-derived scFv, and tethered by CD8α (amino acid 136-182; NP_001759.3 (SEQ ID NO: 23)) to the transmembrane and intracellular portions of CD28 (amino acid 56-123; NP_001230006.1 (SEQ ID NO: 24)) followed by CD3 (amino acid. 48-163; NP_000725.1 (SEQ ID NO: 25)) intracellular domain. Design of all transgenes utilized Vector NTI Advance™ 11 software (Invitrogen). All transgenes were human codon optimized before synthesis at GeneArt. The CARL construct was excised and ligated into a SB expression plasmid, designated Zeo-2A-CARL (FIG. 19E), to co-express Before freezing, the aAPC were routinely tested for the presence of transgenes, absence of mycoplasma, and absence of endotoxin.

Propagation of CAR+ T Cells (CART).

The designs of each CAR and antigen (CARL and CD19) as expressed on the respective T cell or aAPC are shown in FIG. 14A. The propagation of CART is depicted in FIG. 14B. Each CAR from FIG. 14A.II was co-cultured with aAPC from FIG. 14A.I. At the initiation of the experiment (defined as Day 0), thawed PBMC were washed twice, and maintained in CM for 3 to 4 hours before electroporation using the AMAXA® 2D NUCLEOFECTOR® transfection system under program U-14 with human T cell NUCLEO-FECTOR® transfection kit (Lonza Biosciences; Cat No. VPA-1002). After resting overnight in CM, viable PBMC (counted by exclusion of 0.1% Trypan Blue) were resuspended in CM and mixed at a 1:2 ratio (mononuclear cell to γ-irradiated aAPC) using thawed aAPC that were washed twice and counted. The co-culture contained 10$^6$ total cells/mL in CM and 50 IU/mL recombinant human IL-2 (Proleukin, Prometheus Labs, San Diego, Calif.). The live-cell counts were determined by Trypan Blue exclusion on Days 1, 7, 14, and 21 of co-culture. Flow cytometry for CD3, CD4, CD8, and human IgG (to assess CAR expression) occurred on Days 1, 7, 14, and 21, and for CD45RO, CD62L, and CD28 occurred on Days 14 and 21. Irradiated aAPC were re-added to co-cultures on Days 7 and 14 by re-stimulating mononuclear cells with γ-irradiated aAPC at 1:2 ratio. On Day 21 products of propagation were assessed for specific killing, and DNA and RNA were extracted. Each experiment was repeated at least 4 times using 5 donors.

Flow Cytometry.

FACSCALIBER™ cell analysis platform (BD Biosciences, Billerica, Mass.) was used to acquire samples prepared in FACS staining solution as previously described. (Deniger et al. 2013) After washing once in FACS staining solution, cells were stained for 30 minutes at 4° C. without blocking in FACS staining solution containing a 1:33 dilution of antibody. When anti-human Fc antibody was used, the anti-Fc stained sample was washed and re-stained for alternative surface markers before re-suspension in FACS buffer for flow cytometer analysis. Measurement of intracellular cytokine used the same protocol for cell surface staining followed by 20 min. fixation using BD CYTOFIX/CYTOPERM™ kit fixative (BD Biosciences; Cat No. 554714), followed by washing twice in perm/wash buffer containing 20% FBS and staining with a 1:33 dilution of antibody in perm/wash buffer. Antibody incubation lasted 30 minutes at 4° C. before samples were washed in perm/wash buffer and resuspended in FACS staining solution for acquisition. FLOWJO® software v 10.0.5 (Tree Star Inc., Ashland, Oreg.) was used for analysis of flow cytometry data.

Chromium Release Assay (CRA).

CRA was performed as previously described. (Singh et al. 2008) In brief, on Day 21 of T-cell co-culture on aAPC, the tumor targets (i) EL-4, (ii) NALM-6, and (iii) K562 were loaded with 51Cr for 3 hours, and, after washing, co-cultured with effector T cells for 6 hours at 37° C. using a ratio of 5 T cells to 1 target cell.

Abundance and Diversity of TCR Repertoire.

The direct TCR expression assay (DTEA), as previously reported, (Zhang et al. 2012) was used to measure the abundance of mRNA transcripts coding for 45 TCR α alleles, 46 TCR β alleles, 13 TCR γ alleles, and 5 TCR δ alleles from RNA obtained on Day 0 (T cells in PBMC before electroporation) and Day 21 (from T cells after electroporation/propagation). Day 0 samples were negatively sorted for CD56 (Miltenyi Biotec, Cambridge, Mass.; Cat. No. 130-050-401) and then positively sorted for CD3 (Miltenyi Biotec; Cat. No. 130-050-101). The resulting $CD3^+CD56^{neg}$ T cells (2 to $3\times10^6$ from each sample) were snap frozen as were $2\times10^6$ cells directly harvested at Day 21 of co-culture. RNA was extracted from thawed samples using the ALLprep DNA/RNA mini kit (Qiagen; Cat. No. 80204).

Statistics.

Statistical analysis was performed using Prism v6.0 (Graph Pad Software Inc.). Student's t-test (unpaired) was used to perform two sample comparisons. One- or two-way ANOVA F-test was used to perform group comparisons, and if found significant (p<0.05); a t-test (unpaired) was undertaken to assess and report differences. Spearman's nonparametric correlation was performed on housekeeping gene normalized DTEA transcript counts to assess the divergence of the TCR repertoire in T cells from an experimental group and autologous Day 0 PBMC. If the Spearman correlation coefficient was greater than or equal to 0.8 (ρ≥0.8) within the 95% confidence interval of the correlation coefficient, then the two TCR repertoires were considered to be highly correlated.

Results

Numeric Expansion of CAR+ T Cells Upon K562 Cells Expressing CARL or CD19.

Figures 15A, 15B, 15C:
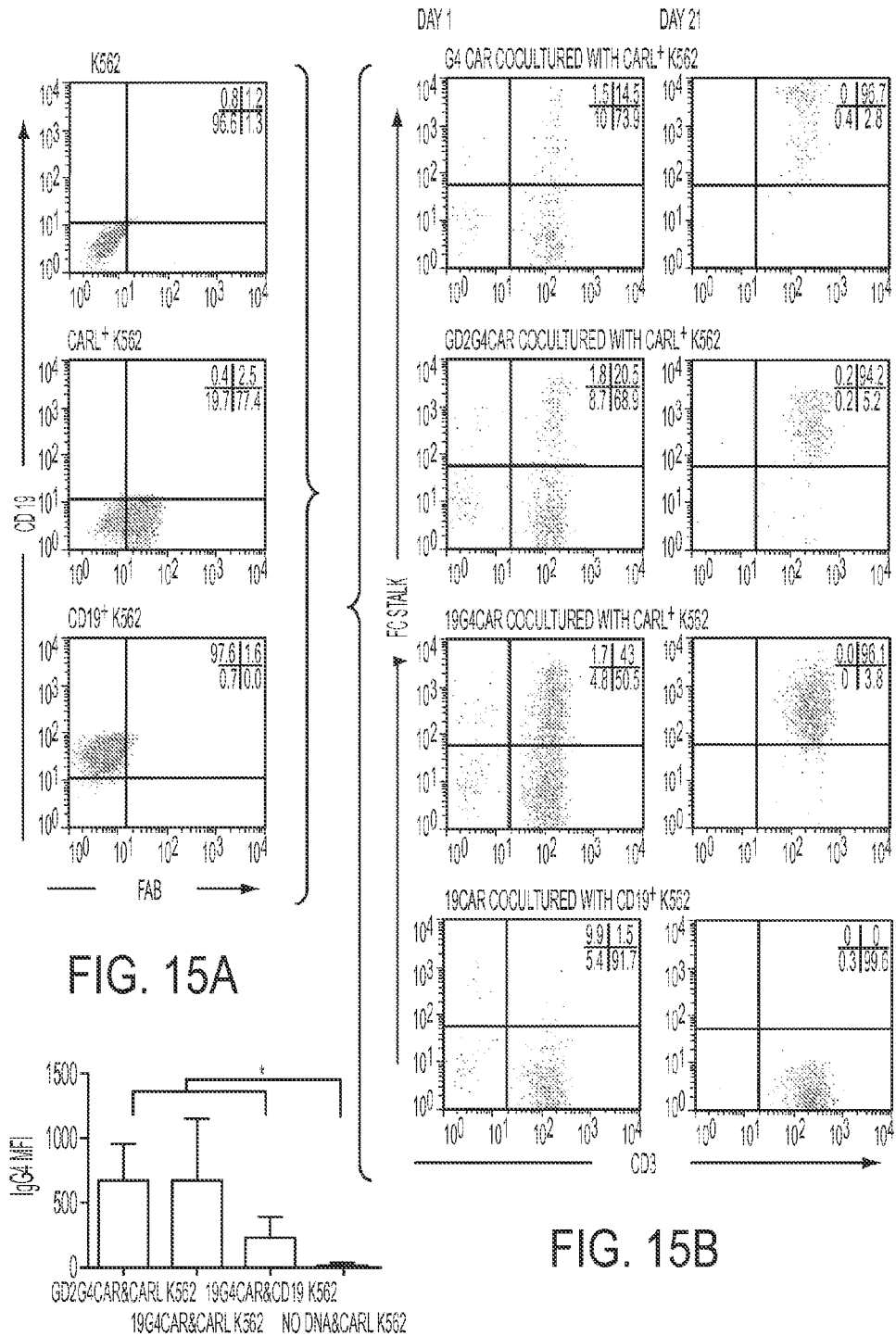
Figures 16A, 16B:
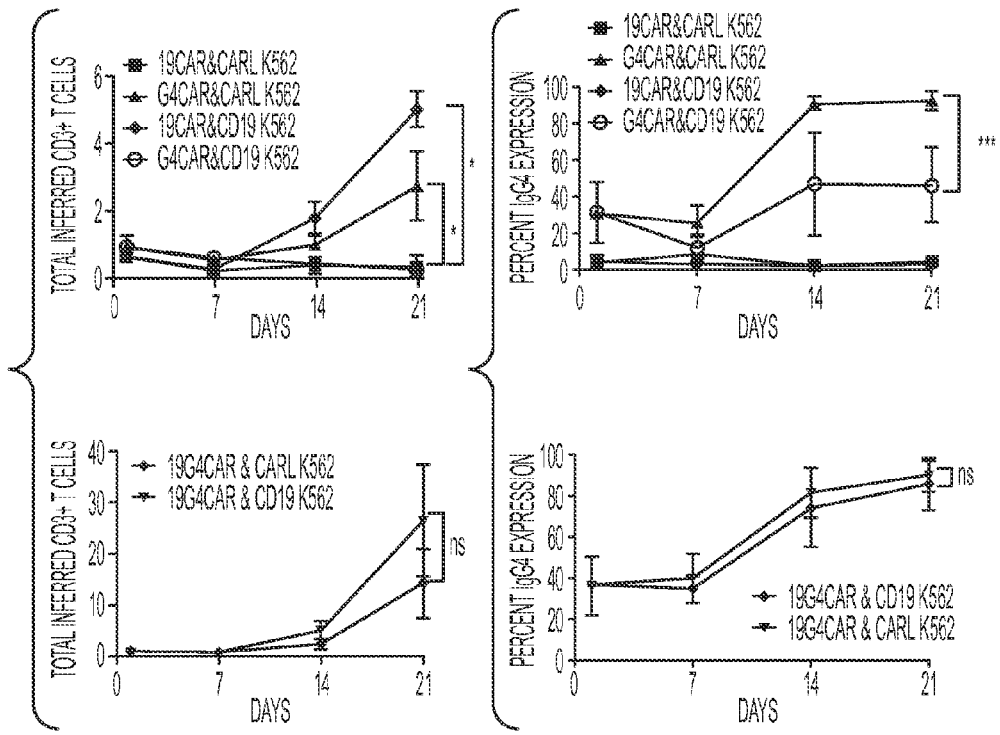
Figures 16C, 16D:
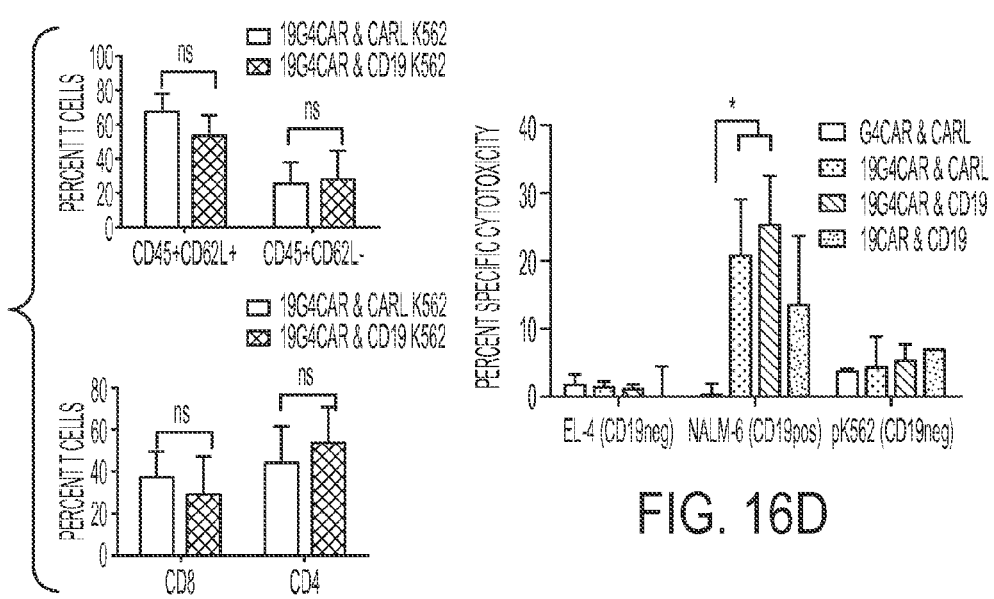

Mouse mAb clone 2D3 was obtained by repeated footpad injections of NSO cells expressing 19G4CAR into BALB/c mice and blocking studies defined the specificity of the mAb to the human IgG4 exodomain of 19G4CAR. (Singh et al. 2008) It was hypothesized that this mAb may be used to cross-link CAR and activate genetically modified T cells for sustained proliferation. Therefore, the scFv of 2D3 (designated CARL) was expressed on the cell surface to compare with human truncated CD19 TAA on K562 cells. The CARL and CD19 transgenes were cloned into DNA plasmids for co-expression with drug-selection genes between SB transposable elements. The SB transposon DNA plasmids for 2D3-derived scFv or CD19 were electro-transferred with SB11 transposase DNA plasmid into K562 cells in separate experiments. Genetically modified cells were propagated under drug selection from a single cell for homogeneous expression of CARL (as detected by antibody against mouse Fab) or CD19 (FIG. 15A). A comparison of the γ-irradiated K562-derived aAPC to selectively propagate CART was undertaken following electroporation (defined as Day 0) of the panel of CAR constructs (FIG. 14A.II) into PBMC using SB system. On Day 1, initial expression of CAR in T cells was evaluated by flow cytometry using antibody specific for human Fc (FIG. 15B). The expression of CARs and number of total viable T cells were measured weekly for 21 days of co-culture with CD19+K562 or CARL+K562 with the following immunoreceptors on T cells; (i) 19G4CAR with specificity for CD19 and containing the IgG4 exodomain, (ii) 19CAR with specificity for CD19 and absence of IgG4 exodomain, (iii) G4CAR without scFv, but containing an IgG4 exodomain, and (iv) GD2G4CAR with specificity for GD2 and containing the IgG4 exodomain. All CAR species contained the same transmembrane and intracellular domains (CD28/CD3ζ) as the 2nd generation 19G4CAR. (Singh et al. 2008) The co-cultures of CART with the two types of aAPC were found to have significantly different amounts of T cells by Day 21 depending on the choice of aAPC (p<0.05) using two-way ANOVA followed by unpaired t-tests. The 19CAR+ T cells proliferated upon co-culture with $CD19^+$ K562 and $G4CAR^+$ T cells proliferated upon co-culture with $CARL^+$ K562 in an exponential fashion, whereas 19CAR on $CARL^+$ K562 and G4CAR on $CD19^+$ K562 did not numerically expand (FIG. 16A top panel). These data indicate that, as expected, the CD19 TAA on aAPC selectively supports the outgrowth of CD19-specific CART. Furthermore, they demonstrate that CARL can activate T cells to proliferate that contain a CAR species with an IgG4 exodomain. Next, the ability of CD19+K562 and CARL+K562 were assessed for ability to sustain the proliferation of T cells expressing 19G4CAR to evaluate how two modes of crosslinking (FIG. 14C) can activate T cells. There were no significant differences in the accumulated number of viable T cells on Day 21 of co-culture based on the type of aAPC used (FIG. 16A bottom panel), the expression of CAR as a percent of the population (FIG. 16B bottom panel), or the mean fluorescence intensity (MFI). A trend (p=0.09) towards a difference in MFI of CAR expression resulting from aAPC employed to expand 19G4CAR was noted (FIG. 15C). There were no significant differences (FIGS. 16C & D) between the two aAPC types for propagating $19G4CAR^+$ T cells co-expressing cell-surface proteins associated with memory phenotype (p=0.82), 25 or other co-receptors (p=0.26), as well as the specific lysis by $19G4CAR^+$ T cells (p=0.16). Therefore, CD19-specific CAR+ T cells can be propagated in similar quantity and quality by K562-derived aAPC expressing CAR or CD19.

$CARL^+$ K562 can Numerically Expand $CAR^+$ T Cells Independent of Specificity.

Figure 17C:
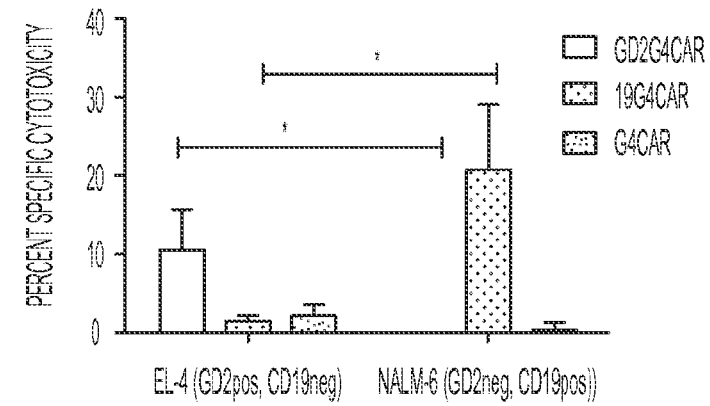

The 2D3-derived scFv on aAPC was evaluated for ability to propagate not just CD19-specific T cells, but $CAR^+$ T cells of alternative specificities. The CD19 and GD226 TAAs are not present on parental K562 cells to propagate T cells expressing GD2G4CAR, 19G4CAR, and G4CAR. Nonetheless, T cells bearing these three CARs numerically expanded on CARL+K562. The number of total viable T cells on Day 21 of co-culture with $CARL^+$ K562 cells did not significantly differ between 19G4CAR, G4CAR, and GD2G4CAR (p=0.16, FIG. 17A). Similarly, the percentage of each CAR expressed on T cells at Day 21 did not significantly differ among the three populations of genetically modified T cells (p=0.68, FIG. 17B). Finally, the electroporated and propagated T cells exhibited specific lysis of CD19 and GD2 TAAs recognized by CD19-specific and GD2-specific CARs. EL-4 cells, previously reported to express GD2 (Alvarez-Rueda et al. 2011) were specifically killed by $GD2G4CAR^+$ T cells and not with T cells expressing G4CAR or 19G4CAR. As anticipated, $CD19^+$ NALM-6 cells were targeted by T cells expressing 19G4CAR (FIG. 17C). In summary, genetically modified T cells can be selectively propagated by CARL⁺ K562 cells resulting in T cells that retain specificity for TAA and stable expression of CAR.

The Choice of aAPC does not Skew the TCR Repertoire for Numerically Expanded CART.

Each T cell in peripheral blood bears a distinct pair of $\alpha\beta$ or $\gamma\delta$ TCRs which can be analyzed using the direct TCR expression assay (DTEA) to determine the abundance of TCR chains. This assay was employed to determine whether CARL⁺ or CD19⁺ K562 influenced the distribution of TCR alleles after 21 days co-culture on aAPC. TCR variants were assayed on the nCounter Analysis System using a set of 111 TCR $\alpha$, $\beta$, $\gamma$, and $\delta$ transcripts. (Deniger et al. 2013; Zhang et al. 2012) By measuring the distribution of TCR alleles we could determine if the aAPC design preferentially supported the numeric expansion of some, but not all genetically modified T cells. The starting TCR distribution of T cells on Day 0 was ranked from the most to least frequent TCR usage and the rank order compared for T cells harvested on Day 21 of co-culture with aAPC (FIG. 18A). This revealed no apparent monoclonal or oligoclonal outgrowth of electroporated T cells propagated on CARL⁺ or CD19⁺ K562 cells. The ranks of TCR frequencies on Day 0 and Day 21 from each experiment were compared using Spearman's rank correlation test and found to significantly correlate (p<0.0001; Table 4). The statistical comparison of TCR abundance and type from Day 0 and 21 indicated that all correlation coefficients ($\rho$) had values greater than 0.8 within the 95% confidence interval of $\rho$ which is consistent with a strong correlation, indicating no change in TCR frequency. The measurement of TCR abundance demonstrates that CARL or TAA on aAPC do not skew the outgrowth of sub-populations of propagated T cells, but rather that both 2D3-derived scFv and CD19 on K562 cells can sustain the outgrowth of CAR⁺ T cells that maintain a polyclonal repertoire.

and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alvarez-Rueda N, Desselle A, Cochonneau D, et al. A monoclonal antibody to O-acetyl-GD2 ganglioside and not to GD2 shows potent antitumor activity without peripheral nervous system cross-reactivity. PloS One. 2011; 6(9):e25220.

Brentjens et al., Safety and persistence of adoptively transferred autologous CD19-targeted T cells in patients with relapsed or chemotherapy refractory B-cell leukemias. Blood, 118:4817-4828, 2011.

Brentjens et al., CD19-targeted cells rapidly induce molecular re et al. missions in adults with chemotherapy-refractory acute lymphoblastic leukemia Sci. Transl. Med., 5:177ra38, 2013.

Cooper et al., T-cell clones can be rendered specific for CD19: toward the selective augmentation of the graft-versus-B-lineage leukemia effect. Blood, 101:1637-1644, 2003.

Cooper et al., Good T cells for bad B cells. Blood, 119: 2700-2702, 2012.

TABLE 4

Comparison of TCR abundance harvested from T cells before versus after propagation on aAPC*.

| | | Day 21 | | | |
|---|---|---|---|---|---|
| | Day 0 | 19G4CAR & CARL⁺ K562 | G4CAR & CARL⁺ K562 | GD2G4CAR & CARL⁺ K562 | 19G4CAR & CD19⁺ K562 |
| Day 0 | | 0.748 (0.65-0.82) | 0.857 (0.80-0.90) | 0.867 (0.81-0.91) | 0.912 (0.87-0.94) |
| Day 21 19G4CAR & CARL⁺ K562 | 0.752 (0.65-0.83) | | 0.805 (0.72-0.86) | 0.706 (0.59-0.79) | 0.734 (0.63-0.81) |
| G4CAR & CARL⁺ K562 | 0.899 (0.85-0.93) | 0.71 (0.61-0.79) | | 0.816 (0.74-0.87) | 0.839 (0.77-0.89) |
| GD2G4CAR & CARL⁺ K562 | 0.825 (0.75-0.88) | 0.72 (0.61-0.80) | 0.801 (0.72-0.86) | | 0.881 (0.83-0.92) |
| 19G4CAR & CD19⁺ K562 | 0.916 (0.87-0.94) | 0.69 (0.57-0.78) | 0.887 (0.84-0.92) | 0.808 (0.73-0.87) | |

*Analysis DTEA data from two donors was normalized using housekeeping genes and assessed using Spearman correlation coefficient to compare distributions of TCR usage for two donors. The upper right of the table contains the correlation between experimental groups for one donor. The lower left of the table contains the second donor subjected to the same analysis. Each cell in the table contains the Spearman correlation coefficient ($\rho$) and within the brackets the 95% confidence interval. (A strong correlation is considered to be $\rho \geq 0.8$.)

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit Davies J K, Singh H, Huls H, et al. Combining CD19 redirection and alloanergization to generate tumor-specific human T cells for allogeneic cell therapy of B-cell malignancies. Can Res. May 15, 2010; 70(10):3915-3924.

Deniger D C, Switzer K, Mi T, et al. Bispecific T-cells expressing polyclonal repertoire of endogenous gammadelta T-cell receptors and introduced CD19-specific chimeric antigen receptor. Mol Ther. March 2013; 21(3): 638-647.

Hackett et al., A transposon and transposase system for human application. Mol. Ther., 18:674-683, 2010.

Hombach et al., Adoptive immunotherapy with genetically engineered T cells: modification of the IgG1 Fc 'spacer' domain in the extracellular moiety of chimeric antigen receptors avoids 'off-target' activation and unintended initiation of an innate immune response. Gene Ther., 17:1206-1213, 2010.

Huls et al., Clinical Application of Sleeping Beauty and Artificial Antigen Presenting Cells to Genetically Modify T Cells from Peripheral and Umbilical Cord Blood. J. Vis. Exp., doi:10.3791/50070, 2012.

Jena et al., Redirecting T-cell specificity by introducing a tumor-specific chimeric antigen receptor. Blood, 116: 1035-1044, 2010.

Jena et al. Chimeric Antigen Receptor (CAR)-specific monoclonal antibody to detect CD19-specific T cells in clinical trial. PLoS One, 8(3):e57838, 2013

June et al., Engineering lymphocyte subsets: tools, trials and tribulations. Nat. Rev. Immunol., 9:704-716, 2009.

Kalos et al., T cells with chimeric antigen receptors have potent antitumor effects and can establish memory in patients with advanced leukemia. Sci. Transl. Med., 3:95ra73, 2011.

Kochenderfer et al., Eradication of B-lineage cells and regression of lymphoma in a patient treated with autologous T cells genetically engineered to recognize CD19. Blood, 116:4099-4102, 2010.

Kochenderfer et al., B-cell depletion and remissions of malignancy along with cytokine-associated toxicity in a clinical trial of anti-CD19 chimeric-antigen-receptor-transduced T cells. Blood, 119:2709-2720, 2012.

Kowolik et al., CD28 costimulation provided through a CD19-specific chimeric antigen receptor enhances in vivo persistence and antitumor efficacy of adoptively transferred T cells. Cancer Res., 66:10995-11004, 2006.

Lamers et al. Immune responses to transgene and retroviral vector in patients treated with ex vivo-engineered T cells. Blood, 117:72-82, 2011.

Ma et al., Anti-prostate specific membrane antigen designer T cells for prostate cancer therapy. Prostate, 61:12-25, 2004.

Maiti et al. J Immunother. Sleeping beauty system to redirect T-cell specificity for human applications 36(2):112-23, 2013.

Manuri et al., piggyBac transposon/transposase system to generate CD19-specific T cells for the treatment of B-lineage malignancies. Hum. Gene Ther., 21:427-437, 2009.

Moeller et al., Adoptive transfer of gene-engineered CD4+ helper T cells induces potent primary and secondary tumor rejection. Blood, 106:2995-3003, 2005.

Morgan et al., Cancer regression in patients after transfer of genetically engineered lymphocytes. Science, 314:126-129, 2006.

Morgan, Adoptive cell therapy: genetic modification to redirect effector cell specificity. Cancer J., 16:336-341, 2010.

Nicholson et al. Construction and characterisation of a functional CD19 specific single chain Fv fragment for immunotherapy of B lineage leukaemia and lymphoma. Mol. Immunol., 34:1157-1165, 1997.

O'Connor et al., Adoptive T-cell therapy improves treatment of canine non-Hodgkin lymphoma post chemotherapy. Scientific Reports, 2, 2012.

Park et al., Adoptive transfer of chimeric antigen receptor re-directed cytolytic T lymphocyte clones in patients with neuroblastoma. Mol. Ther., 15:825-833, 2007.

Porter et al., Chimeric Antigen Receptor-Modified T Cells in Chronic Lymphoid Leukemia. New England Journal of Medicine, 365:725-733, 2011.

Pule et al., Virus-specific T cells engineered to coexpress tumor-specific receptors: persistence and antitumor activity in individuals with neuroblastoma. Nat. Med., 14:1264-1270, 2008.

Rabinovich et al. A role for the MHC class I-like Mill molecules in nutrient metabolism and wound healing. Immunol. Cell Biol. 86: 489-496, 2008

Rossig et al., Targeting of G(D2)-positive tumor cells by human T lymphocytes engineered to express chimeric T-cell receptor genes. Int. J. Cancer, 94:228-236, 2001.

Rossig et al., Epstein-Barr virus-specific human T lymphocytes expressing antitumor chimeric T-cell receptors: potential for improved immunotherapy. Blood, 99:2009-2016, 2002.

Savoldo et al., CD28 costimulation improves expansion and persistence of chimeric antigen receptor-modified T cells in lymphoma patients. J. Clin. Invest., 121:1822-1826, 2011.

Singh et al., Redirecting specificity of T-cell populations for CD19 using the Sleeping Beauty system. Cancer Res., 68:2961-2971, 2008.

Singh et al., Reprogramming CD19-specific T cells with IL-21 signaling can improve adoptive immunotherapy of B-lineage malignancies. Cancer Res., 71:3516-3527, 2011.

Till et al., Adoptive immunotherapy for indolent non-Hodgkin lymphoma and mantle cell lymphoma using genetically modified autologous CD20-specific T cells. Blood, 112:2261-2271, 2008.

Torikai et al., A foundation for universal T-cell based immunotherapy: T cells engineered to express a CD19-specific chimeric-antigen-receptor and eliminate expression of endogenous TCR. Blood, 119:5697-5705, 2012.

Vera et al., T lymphocytes redirected against the kappa light chain of human immunoglobulin efficiently kill mature B lymphocyte-derived malignant cells. Blood, 108:3890-3897, 2006.

Wang Z, Raifu M, Howard M, et al. Universal PCR amplification of mouse immunoglobulin gene variable regions: the design of degenerate primers and an assessment of the effect of DNA polymerase 3' to 5' exonuclease activity. *J Immuno Methods*. Jan. 13, 2000; 233(1-2):167-177.

Whitlow et al., An improved linker for single-chain Fv with reduced aggregation and enhanced proteolytic stability. Protein Engineering, 6:989-995, 1993.

Zhang M, Maiti S, Bernatchez C, et al. A new approach to simultaneously quantify both TCR alpha- and beta-chain diversity after adoptive immunotherapy. *Clin Can Res.* Sep. 1, 2012; 18(17):4733-4742.

Zheng et al., Protein L: a novel reagent for the detection of chimeric antigen receptor (CAR) expression by flow cytometry J. Transl. Med., 10:29, 2012.

The invention claimed is:

1. An isolated antibody or antibody fragment thereof, that specifically binds to a CD19-specific scFv (FMC63) chimeric antigen receptor (CAR) polypeptide, wherein the isolated antibody or antibody fragment comprises a set of complementarity determining regions (CDRs) HCDR1, HCDR2, HCDR3, LCDR1, LCDR2 and LCDR3, wherein
   (a) HCDR1 has the amino acid sequence of SEQ ID NO: 2;
   (b) HCDR2 has the amino acid sequence of SEQ ID NO: 3;
   (c) HCDR3 has the amino acid sequence of SEQ ID NO: 4;
   (d) LCDR1 has the amino acid sequence of SEQ ID NO: 6;
   (e) LCDR2 has the amino acid sequence of SEQ ID NO: 7; and
   (f) LCDR3 has the amino acid sequence of SEQ ID NO: 8.

2. An isolated antibody or antibody fragment thereof that specifically binds to a CD19-specific scFv (FMC63) chimeric antigen receptor (CAR) polypeptide, wherein the isolated antibody or antibody fragment comprises a heavy chain variable region (VH) having the amino acid sequence of SEQ ID NO: 1, and a light chain variable region (VL) having the amino acid sequence of SEQ ID NO: 5.

3. A pharmaceutical composition comprising the antibody or antibody fragment thereof of claim 1.

4. A pharmaceutical composition comprising the antibody or antibody fragment thereof of claim 2.

5. The isolated antibody or antibody fragment thereof of claim 1, wherein the antibody or antibody fragment thereof is conjugated to a toxin.

6. The isolated antibody or antibody fragment thereof of claim 2, wherein the antibody or antibody fragment thereof is conjugated to a toxin.

* * * * *

UNITED STATES PATENT AND TRADEMARK OFFICE
CERTIFICATE OF CORRECTION

PATENT NO. : 9,701,758 B2
APPLICATION NO. : 14/893223
DATED : July 11, 2017
INVENTOR(S) : Laurence J N Cooper et al.

Page 1 of 1

It is certified that error appears in the above-identified patent and that said Letters Patent is hereby corrected as shown below:

In the Specification

Column 1, Lines 9-13, delete the entire contents and replace with --This invention was made with government support under Grant Numbers CA016672, CA124782, CA120956, CA141303, CA116127 and CA148600 awarded by the National Institutes of Health. The Government has certain rights in the invention.-- therefor.

Signed and Sealed this
Twentieth Day of March, 2018

Andrei Iancu
*Director of the United States Patent and Trademark Office*

SEQUENCE LISTING

<160> NUMBER OF SEQ ID NOS: 26

<210> SEQ ID NO 1

```
<211> LENGTH: 153
<212> TYPE: PRT
<213> ORGANISM: Artificial Sequence
<220> FEATURE:
<223> OTHER INFORMATION: Antibody sequence

<400> SEQUENCE: 1

Leu Lys Pro Arg Glu Val Lys Leu Val Glu Ser Gly Gly Gly Leu Val
1               5                   10                  15

Gln Pro Gly Gly Ser Leu Lys Leu Ser Cys Ala Ala Ser Gly Phe Asp
            20                  25                  30

Phe Ser Arg Tyr Trp Met Ser Trp Val Arg Gln Ala Pro Gly Lys Gly
        35                  40                  45

Leu Glu Trp Ile Gly Glu Ile Asn Leu Asp Ser Ser Thr Ile Asn Tyr
    50                  55                  60

Thr Pro Ser Leu Lys Asp Lys Phe Ile Ile Ser Arg Asp Asn Ala Lys
65                  70                  75                  80

Asn Thr Leu Tyr Leu Gln Met Ser Lys Val Arg Ser Glu Asp Thr Ala
                85                  90                  95

Leu Tyr Tyr Cys Ala Arg Arg Tyr Asp Ala Met Asp Tyr Trp Gly Gln
            100                 105                 110

Gly Thr Ser Val Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Ala Ser Gln
145                 150

<210> SEQ ID NO 2
<211> LENGTH: 8
<212> TYPE: PRT
<213> ORGANISM: Artificial Sequence
<220> FEATURE:
<223> OTHER INFORMATION: Antibody polypeptide

<400> SEQUENCE: 2

Gly Phe Asp Phe Ser Arg Tyr Trp
1               5

<210> SEQ ID NO 3
<211> LENGTH: 8
<212> TYPE: PRT
<213> ORGANISM: Artificial Sequence
<220> FEATURE:
<223> OTHER INFORMATION: Antibody polypeptide

<400> SEQUENCE: 3

Ile Asn Leu Asp Ser Ser Thr Ile
1               5

<210> SEQ ID NO 4
<211> LENGTH: 9
<212> TYPE: PRT
<213> ORGANISM: Artificial Sequence
<220> FEATURE:
<223> OTHER INFORMATION: Antibody polypeptide

<400> SEQUENCE: 4

Ala Arg Arg Tyr Asp Ala Met Asp Tyr
1               5

<210> SEQ ID NO 5
```

<211> LENGTH: 111
<212> TYPE: PRT
<213> ORGANISM: Artificial Sequence
<220> FEATURE:
<223> OTHER INFORMATION: Antibody polypeptide

<400> SEQUENCE: 5

Ala Ser Asp Ile Val Leu Thr Gln Ser Pro Ala Ser Leu Ala Val Ser
1               5                   10                  15

Leu Gly Gln Arg Ala Thr Ile Ser Cys Arg Ala Ser Glu Ser Val Asp
            20                  25                  30

Asp Tyr Gly Ile Ser Phe Met Asn Trp Phe Gln Gln Lys Pro Gly Gln
        35                  40                  45

Pro Pro Lys Leu Leu Ile Tyr Ala Ala Pro Asn Gln Gly Ser Gly Val
    50                  55                  60

Pro Ala Arg Phe Ser Gly Ser Gly Ser Gly Thr Asp Phe Ser Leu Asn
65                  70                  75                  80

Ile His Pro Met Glu Glu Asp Asp Thr Ala Met Tyr Phe Cys Gln Gln
                85                  90                  95

Ser Lys Asp Val Arg Trp Arg His Gln Ala Gly Asp Gln Thr Gly
            100                 105                 110

<210> SEQ ID NO 6
<211> LENGTH: 10
<212> TYPE: PRT
<213> ORGANISM: Artificial Sequence
<220> FEATURE:
<223> OTHER INFORMATION: Antibody polypeptide

<400> SEQUENCE: 6

Glu Ser Val Asp Asp Tyr Gly Ile Ser Phe
1               5                   10

<210> SEQ ID NO 7
<211> LENGTH: 3
<212> TYPE: PRT
<213> ORGANISM: Artificial Sequence
<220> FEATURE:
<223> OTHER INFORMATION: Antibody polypeptide

<400> SEQUENCE: 7

Ala Ala Pro
1

<210> SEQ ID NO 8
<211> LENGTH: 5
<212> TYPE: PRT
<213> ORGANISM: Artificial Sequence
<220> FEATURE:
<223> OTHER INFORMATION: Antibody polypeptide

<400> SEQUENCE: 8

Gln Gln Ser Lys Asp
1               5

<210> SEQ ID NO 9
<211> LENGTH: 140
<212> TYPE: PRT
<213> ORGANISM: Artificial Sequence
<220> FEATURE:
<223> OTHER INFORMATION: Antibody polypeptide
<220> FEATURE:
<221> NAME/KEY: misc_feature
<222> LOCATION: (4)..(4)
<223> OTHER INFORMATION: Xaa can be any naturally occurring amino acid

```
<400> SEQUENCE: 9

Pro Arg Glu Xaa Lys Leu Glu Gln Ser Gly Thr Val Leu Ala Arg Pro
1               5                   10                  15

Gly Ala Ser Val Lys Met Ser Cys Lys Thr Ser Gly Tyr Thr Phe Thr
            20                  25                  30

Ser Tyr Trp Met His Trp Val Ile Gln Arg Pro Gly Gln Gly Leu Glu
        35                  40                  45

Trp Ile Gly Ala Ile Tyr Pro Gly Asn Ser Asp Thr Asn Tyr Asn Gln
    50                  55                  60

Lys Phe Lys Val Lys Ala Lys Leu Thr Ala Val Thr Ser Thr Ser Thr
65                  70                  75                  80

Ala Tyr Met Glu Leu Ser Ser Leu Thr Asp Glu Asp Ser Ala Val Tyr
                85                  90                  95

Tyr Cys Thr Arg Val Asn Trp Asp Gly Tyr Ser Thr Met Asp Tyr Trp
            100                 105                 110

Gly Gln Gly Thr Ser Val Thr Val Ser Ser Ala Lys Thr Thr Pro Pro
        115                 120                 125

Ser Val Tyr Ala Ser Gln Arg Ala Asn Ser Arg Pro
        130                 135             140

<210> SEQ ID NO 10
<211> LENGTH: 8
<212> TYPE: PRT
<213> ORGANISM: Artificial Sequence
<220> FEATURE:
<223> OTHER INFORMATION: Antibody polypeptide

<400> SEQUENCE: 10

Gly Tyr Thr Phe Thr Ser Tyr Trp
1               5

<210> SEQ ID NO 11
<211> LENGTH: 8
<212> TYPE: PRT
<213> ORGANISM: Artificial Sequence
<220> FEATURE:
<223> OTHER INFORMATION: Antibody polypeptide

<400> SEQUENCE: 11

Ile Tyr Pro Gly Asn Ser Asp Thr
1               5

<210> SEQ ID NO 12
<211> LENGTH: 13
<212> TYPE: PRT
<213> ORGANISM: Artificial Sequence
<220> FEATURE:
<223> OTHER INFORMATION: Antibody polypeptide

<400> SEQUENCE: 12

Thr Arg Val Asn Trp Asp Gly Tyr Ser Thr Met Asp Tyr
1               5                   10

<210> SEQ ID NO 13
<211> LENGTH: 115
<212> TYPE: PRT
<213> ORGANISM: Artificial Sequence
<220> FEATURE:
<223> OTHER INFORMATION: Antibody polypeptide

<400> SEQUENCE: 13
```

```
Ser Thr Leu Ser Leu Pro Val Ser Leu Gly Asp Gln Ala Ser Ile Ser
1               5                   10                  15

Cys Arg Ser Ser Gln Ser Leu Val His Ser Asn Gly Asn Thr Tyr Phe
            20                  25                  30

His Trp Tyr Leu Gln Lys Pro Gly Gln Ser Pro Lys Leu Leu Ile Tyr
        35                  40                  45

Lys Val Ser Asn Arg Phe Ser Gly Val Pro Asp Arg Phe Ser Gly Ser
    50                  55                  60

Gly Ser Gly Thr Asn Phe Thr Leu Lys Ile Ser Arg Val Glu Ala Glu
65                  70                  75                  80

Asp Leu Gly Val Tyr Phe Cys Ser Gln Thr Thr His Val Pro Tyr Thr
                85                  90                  95

Phe Gly Gly Gly Thr Glu Leu Glu Ile Lys Arg Ala Asp Ala Ala Pro
            100                 105                 110

Thr Val Ser
        115

<210> SEQ ID NO 14
<211> LENGTH: 11
<212> TYPE: PRT
<213> ORGANISM: Artificial Sequence
<220> FEATURE:
<223> OTHER INFORMATION: Antibody polypeptide

<400> SEQUENCE: 14

Gln Ser Leu Val His Ser Asn Gly Asn Thr Tyr
1               5                   10

<210> SEQ ID NO 15
<211> LENGTH: 3
<212> TYPE: PRT
<213> ORGANISM: Artificial Sequence
<220> FEATURE:
<223> OTHER INFORMATION: Antibody polypeptide

<400> SEQUENCE: 15

Lys Val Ser
1

<210> SEQ ID NO 16
<211> LENGTH: 11
<212> TYPE: PRT
<213> ORGANISM: Artificial Sequence
<220> FEATURE:
<223> OTHER INFORMATION: Antibody polypeptide

<400> SEQUENCE: 16

Cys Ser Gln Thr Thr His Val Pro Tyr Thr Phe
1               5                   10

<210> SEQ ID NO 17
<211> LENGTH: 711
<212> TYPE: PRT
<213> ORGANISM: Artificial Sequence
<220> FEATURE:
<223> OTHER INFORMATION: Fusion protein

<400> SEQUENCE: 17

Met Leu Leu Leu Val Thr Ser Leu Leu Leu Cys Glu Leu Pro His
1               5                   10                  15

Pro Ala Phe Leu Leu Ile Pro Asp Ile Gln Met Thr Gln Gln Thr Thr
            20                  25                  30
```

Ser Ser Leu Ser Ala Ser Leu Gly Asp Arg Val Thr Ile Ser Cys Arg
            35                  40                  45

Ala Ser Gln Asp Ile Ser Lys Tyr Leu Asn Trp Tyr Gln Gln Lys
 50                  55                  60

Pro Asp Gly Thr Val Lys Leu Leu Ile Tyr His Thr Ser Arg Leu
 65                  70                  75                  80

His Ser Gly Val Pro Ser Arg Phe Ser Gly Ser Gly Ser Gly Thr
                85                  90                  95

Asp Tyr Ser Leu Thr Ile Ser Asn Leu Glu Gln Glu Asp Ile Ala Thr
            100                 105                 110

Tyr Tyr Phe Cys Gln Gln Gly Asn Thr Leu Pro Tyr Thr Phe Gly Gly
            115                 120                 125

Gly Thr Lys Leu Glu Ile Ile Thr Gly Ser Thr Ser Gly Ser Gly Lys
    130                 135                 140

Pro Gly Ser Gly Glu Gly Ser Thr Lys Gly Glu Val Lys Leu Gln
 145                 150                 155                 160

Glu Ser Gly Pro Gly Leu Val Ala Pro Ser Gln Ser Leu Ser Val Thr
                165                 170                 175

Thr Cys Thr Val Ser Gly Val Ser Leu Pro Asp Tyr Gly Val Ser Trp
            180                 185                 190

Ile Arg Gln Pro Pro Arg Lys Gly Leu Glu Trp Leu Gly Val Ile
            195                 200                 205

Trp Gly Ser Glu Thr Thr Tyr Tyr Asn Ser Ser Ala Leu Lys Ser Arg
    210                 215                 220

Leu Thr Ile Ile Lys Asp Asn Ser Lys Ser Gln Val Phe Leu Lys Lys
225                 230                 235                 240

Met Asn Ser Leu Gln Thr Asp Asp Thr Ala Ile Tyr Tyr Cys Ala Lys
            245                 250                 255

His Tyr Tyr Tyr Gly Gly Ser Tyr Ala Met Asp Tyr Trp Gly Gln
            260                 265                 270

Gly Thr Ser Val Thr Val Ser Ser Glu Glu Ser Lys Tyr Gly Pro Pro
    275                 280                 285

Cys Pro Pro Cys Pro Ala Pro Glu Phe Leu Gly Gly Pro Ser Ser Val
 290                 295                 300

Phe Leu Phe Pro Pro Lys Pro Lys Asp Thr Leu Met Ile Ser Arg Thr
305                 310                 315                 320

Pro Glu Val Val Thr Cys Val Val Asp Val Ser Gln Glu Asp Pro
            325                 330                 335

Glu Val Gln Phe Asn Trp Tyr Val Asp Gly Val Glu Val His Asn
            340                 345                 350

Ala Lys Thr Lys Pro Arg Glu Glu Gln Phe Asn Ser Thr Tyr Arg
            355                 360                 365

Val Val Ser Val Leu Thr Val Leu His Gln Asp Trp Leu Asn Gly Lys
    370                 375                 380

Glu Tyr Tyr Lys Cys Lys Val Ser Asn Lys Gly Leu Pro Ser Ser Ile
385                 390                 395                 400

Glu Lys Thr Ile Ser Lys Ala Ala Lys Gly Gln Pro Arg Glu Pro Gln
            405                 410                 415

Val Tyr Thr Leu Pro Pro Ser Gln Glu Met Thr Thr Lys Asn Gln
            420                 425                 430

Val Ser Leu Thr Cys Leu Val Lys Gly Phe Tyr Pro Ser Asp Ile Ala
            435                 440                 445

Val Val Glu Trp Glu Ser Asn Gly Gln Pro Glu Asn Asn Tyr Lys Thr

```
            450                 455                 460
Thr Pro Pro Val Leu Asp Asp Ser Gly Ser Phe Phe Leu Tyr Ser
465                 470                 475                 480

Arg Leu Thr Val Asp Lys Ser Arg Trp Gln Glu Gly Asn Val Phe
            485                 490                 495

Ser Cys Ser Val Met His Glu Ala Leu His Asn His Tyr Thr Gln Lys
                500                 505                 510

Lys Ser Leu Ser Leu Ser Leu Gly Lys Met Phe Trp Val Leu Val Val
            515                 520                 525

Val Gly Gly Val Leu Leu Ala Cys Tyr Ser Leu Leu Val Thr Val Ala
        530                 535                 540

Phe Ile Ile Phe Trp Val Arg Ser Lys Arg Ser Arg Gly Gly His
545                 550                 555                 560

Ser Asp Tyr Met Asn Met Thr Pro Arg Arg Pro Gly Pro Thr Arg Arg
                565                 570                 575

Lys His Tyr Gln Pro Tyr Ala Pro Pro Arg Asp Phe Ala Ala Tyr Arg
            580                 585                 590

Ser Arg Val Lys Lys Phe Ser Arg Ser Ala Asp Ala Pro Ala Tyr Gln
        595                 600                 605

Gln Gly Gln Asn Gln Leu Tyr Asn Glu Leu Asn Leu Gly Arg Arg
610                 615                 620

Glu Glu Tyr Asp Val Leu Asp Lys Arg Arg Gly Arg Asp Pro Glu
625                 630                 635                 640

Met Gly Gly Lys Pro Arg Arg Lys Asn Pro Gln Glu Gly Leu Tyr Asn
                645                 650                 655

Glu Leu Gln Gln Lys Asp Lys Met Ala Glu Ala Tyr Ser Glu Ile Gly
            660                 665                 670

Met Lys Gly Glu Arg Arg Arg Gly Gly Lys Gly His Asp Gly Leu Tyr
            675                 680                 685

Gln Gly Leu Ser Thr Ala Thr Lys Asp Thr Tyr Asp Ala Ala Leu His
            690                 695                 700

Met Gln Ala Leu Pro Pro Arg
705                 710

<210> SEQ ID NO 18
<211> LENGTH: 229
<212> TYPE: PRT
<213> ORGANISM: Artificial Sequence
<220> FEATURE:
<223> OTHER INFORMATION: Fusion protein

<400> SEQUENCE: 18

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
```

100                 105                 110
Ser Ile Glu Lys Thr Ile Ser Lys Ala Lys Gly Gln Pro Arg Glu Pro
                115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 19
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 19

Met Glu Thr Asp Thr Leu Leu Leu Trp Val Leu Leu Leu Trp Val Pro
1               5                   10                  15

Gly Ser Thr Gly Asp Tyr Lys Asp Glu Gly Thr Ser
            20                  25

<210> SEQ ID NO 20
<211> LENGTH: 28
<212> TYPE: DNA
<213> ORGANISM: Artificial Sequence
<220> FEATURE:
<223> OTHER INFORMATION: Synthetic primer

<400> SEQUENCE: 20
ggtacctctg gggggcaggg cctgcatg                                          28

<210> SEQ ID NO 21
<211> LENGTH: 33
<212> TYPE: DNA
<213> ORGANISM: Artificial Sequence
<220> FEATURE:
<223> OTHER INFORMATION: Synthetic primer

<400> SEQUENCE: 21
gggcccagcg ctgagagcaa gtacggccct ccc                                    33

<210> SEQ ID NO 22
<211> LENGTH: 233
<212> TYPE: PRT
<213> ORGANISM: Homo sapiens

<400> SEQUENCE: 22

Met Leu Leu Leu Val Thr Ser Leu Leu Leu Cys Glu Leu Pro His Pro
1               5                   10                  15

Ala Phe Leu Leu Ile Pro Glu Lys Ser Asp Leu Arg Thr Val Ala Pro
            20                  25                  30

-continued

```
Ala Ser Ser Leu Asn Val Arg Phe Asp Ser Arg Thr Met Asn Leu Ser
         35                  40                  45

Trp Asp Cys Gln Glu Asn Thr Thr Phe Ser Lys Cys Phe Leu Thr Asp
 50                  55                  60

Lys Lys Asn Arg Val Val Glu Pro Arg Leu Ser Asn Asn Glu Cys Ser
 65                  70                  75                  80

Cys Thr Phe Arg Glu Ile Cys Leu His Glu Gly Val Thr Phe Glu Val
                 85                  90                  95

His Val Asn Thr Ser Gln Arg Gly Phe Gln Gln Lys Leu Leu Tyr Pro
            100                 105                 110

Asn Ser Gly Arg Glu Gly Thr Ala Ala Gln Asn Phe Ser Cys Phe Ile
        115                 120                 125

Tyr Asn Ala Asp Leu Met Asn Cys Thr Trp Ala Arg Gly Pro Thr Ala
130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
        195                 200                 205

Leu Leu Asp Thr Lys Lys Ile Gly Ser Leu Gly Tyr Ser Gly Cys Ser
210                 215                 220

Arg Gln Phe His Arg Ser Lys Thr Asn
225                 230

<210> SEQ ID NO 23
<211> LENGTH: 235
<212> TYPE: PRT
<213> ORGANISM: Homo sapiens

<400> SEQUENCE: 23

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
         35                  40                  45

Asn Pro Thr Ser Gly Cys Ser Trp Leu Phe Gln Pro Arg Gly Ala Ala
 50                  55                  60

Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                 85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
```

```
                165                 170                 175

Leu Asp Phe Ala Cys Asp Ile Tyr Ile Trp Ala Pro Leu Ala Gly Thr
            180                 185                 190

Cys Gly Val Leu Leu Ser Leu Val Ile Thr Leu Tyr Cys Asn His
            195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 24
<211> LENGTH: 123
<212> TYPE: PRT
<213> ORGANISM: Homo sapiens

<400> SEQUENCE: 24

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Trp Lys His Leu Cys Pro Ser Pro Leu
            35                  40                  45

Phe Pro Gly Pro Ser Lys Pro Phe Trp Val Leu Val Val Val Gly Gly
        50                  55                  60

Val Leu Ala Cys Tyr Ser Leu Leu Val Thr Val Ala Phe Ile Ile Phe
65                  70                  75                  80

Trp Val Arg Ser Lys Arg Ser Arg Leu Leu His Ser Asp Tyr Met Asn
                85                  90                  95

Met Thr Pro Arg Arg Pro Gly Pro Thr Arg Lys His Tyr Gln Pro Tyr
            100                 105                 110

Ala Pro Pro Arg Asp Phe Ala Ala Tyr Arg Ser
        115                 120

<210> SEQ ID NO 25
<211> LENGTH: 163
<212> TYPE: PRT
<213> ORGANISM: Homo sapiens

<400> SEQUENCE: 25

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
```

-continued

```
                130                 135                 140
Ser Thr Ala Thr Lys Asp Thr Tyr Asp Ala Leu His Met Gln Ala Leu
145                 150                 155                 160

Pro Pro Arg

<210> SEQ ID NO 26
<211> LENGTH: 18
<212> TYPE: PRT
<213> ORGANISM: Artificial sequence
<220> FEATURE:
<223> OTHER INFORMATION: Synthetic peptide

<400> SEQUENCE: 26

Gly Ser Thr Ser Gly Ser Gly Lys Pro Gly Ser Gly Glu Gly Ser Thr
1               5                   10                  15

Lys Gly
```